US012617799B2

(12) United States Patent
Raheja et al.

(10) Patent No.: US 12,617,799 B2
(45) Date of Patent: May 5, 2026

(54) PYRAZOLOPYRIMIDINONE COMPOUNDS

(71) Applicant: Orphagen Pharmaceuticals, Inc., San Diego, CA (US)

(72) Inventors: Neil Raheja, San Diego, CA (US); Paul Crowe, San Diego, CA (US); Haiyan Tao, San Diego, CA (US); Scott Thacher, San Diego, CA (US)

(73) Assignee: ORPHAGEN PHARMACEUTICALS, INC., San Diego, CA (US)

( * ) Notice: Subject to any disclaimer, the term of this patent is extended or adjusted under 35 U.S.C. 154(b) by 394 days.

(21) Appl. No.: 18/552,297

(22) PCT Filed: Mar. 25, 2022

(86) PCT No.: PCT/US2022/021890

§ 371 (c)(1), (2) Date: Sep. 25, 2023

(87) PCT Pub. No.: WO2022/204481

PCT Pub. Date: Sep. 29, 2022

(65) Prior Publication Data

US 2024/0208982 A1 Jun. 27, 2024

Related U.S. Application Data

(60) Provisional application No. 63/166,739, filed on Mar. 26, 2021.

(51) Int. Cl.

| | |
|---|---|
| ***C07D 487/04*** | (2006.01) |
| ***A61K 31/519*** | (2006.01) |
| ***A61P 35/00*** | (2006.01) |

(52) U.S. Cl.

CPC .......... *C07D 487/04* (2013.01); *A61K 31/519* (2013.01); *A61P 35/00* (2018.01)

(58) Field of Classification Search

CPC ..... C07D 487/04; A61K 31/519; A61P 35/00; A61P 5/00

See application file for complete search history.

(56) References Cited

FOREIGN PATENT DOCUMENTS

| | | | |
|---|---|---|---|
| CN | 112409331 | A | 2/2021 |
| WO | WO-2005042712 | A2 | 5/2005 |
| WO | WO-2008133866 | A1 | 11/2008 |
| WO | WO-2015155306 | A1 | 10/2015 |
| WO | WO-2018045071 | A1 | 3/2018 |
| WO | WO-2019074979 | A1 | 4/2019 |
| WO | WO-2019165204 | A1 | 8/2019 |
| WO | WO-2020097609 | A1 | 5/2020 |
| WO | WO-2022204481 | A1 | 9/2022 |

OTHER PUBLICATIONS

Schimmer, Bernard P. et al. Minireview: steroidogenic factor 1: its roles in differentiation, development, and disease. Molecular endocrinology 24(7):1322-1337 (2010).

Berge et al. Pharmaceutical Salts. Journal of Pharmaceutical Sciences 66(1):1-19 (Jan. 1977).

PCT/US2022/021890 International Search Report and Written Opinion dated May 31, 2022.

*Primary Examiner* — San Ming R Hui

(74) *Attorney, Agent, or Firm* — WILSON SONSINI GOODRICH & ROSATI

(57) ABSTRACT

Provided herein are pyrazolopyrimidinone compounds and pharmaceutical compositions comprising said compounds.

20 Claims, No Drawings

PYRAZOLOPYRIMIDINONE COMPOUNDS

CROSS-REFERENCE

This application claims benefit of U.S. Provisional Patent Application No. 63/166,739, filed on Mar. 26, 2021 which is incorporated herein by reference in its entirety.

BACKGROUND

Steroidogenic factor 1 (SF-1, NR5A1) is a transcriptional regulator of genes involved in the development and function of steroidogenic tissues. SF-1 modulators provide an opportunity for new therapeutic compounds that regulate the growth and function of SF-1-dependent tissues.

BRIEF SUMMARY OF THE INVENTION

This disclosure provides, for example, pyrazolopyrimidine compounds, their use as medicinal agents for the treatment of cancer, processes for their preparation, and pharmaceutical compositions that include disclosed compounds as at least one active ingredient. The disclosure also provides for the use of compounds described herein as medicaments and/or in the manufacture of medicaments for the treatment of cancer, endocrine diseases, and endometriosis.

In one aspect is a compound of Formula (I):

Formula (I)

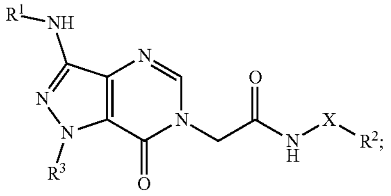

wherein:

X is a bond or $C_1$-$C_6$alkylene;

$R^1$ is selected from $C_{3-8}$cycloalkyl, $C_{2-9}$heterocycloalkyl, —$CH_2C_{6-10}$aryl, $C_{6-10}$aryl, and $C_{1-9}$heteroaryl, wherein $C_{3-8}$cycloalkyl, $C_{2-9}$heterocycloalkyl, —$CH_2C_{6-10}$aryl, $C_{6-10}$aryl and $C_{1-9}$heteroaryl are optionally substituted with one, two, three, four, or five $R^4$;

$R^2$ is selected from $C_{3-8}$cycloalkyl, $C_{2-9}$heterocycloalkyl, $C_{6-10}$aryl and $C_{1-9}$heteroaryl, wherein $C_{3-8}$cycloalkyl, $C_{2-9}$heterocycloalkyl, $C_{6-10}$aryl and $C_{1-9}$heteroaryl are optionally substituted with one, two, three, four, or five $R^5$;

$R^3$ is hydrogen, $C_1$-$C_6$alkyl, $C_1$-$C_6$haloalkyl, or $C_{3-8}$cycloalkyl;

each $R^4$ and each $R^5$ are each independently selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^6$, —$SR^6$, —$C(O)OR^6$, —$OC(O)N(R^6)(R^7)$, —$N(R^8)C(O)N(R^6)(R^7)$, —$N(R^8)C(O)R^9$, —$N(R^8)C(O)OR^9$, —$N(R^8)S(O)_2R^9$, —$C(O)R^9$, —$OC(O)R^9$, —$C(O)N(R^6)(R^7)$, —$C(O)C(O)N(R^6)(R^7)$, —$S(O)R^9$, —$S(O)_2R^9$, and —$S(O)_2N(R^6)(R^7)$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$C(O)OR^{10}$, —$OC(O)N(R^{10})(R^{11})$, —$N(R^{12})C(O)N(R^{10})(R^{11})$, —$N(R^{12})C(O)R^{13}$, —$N(R^{12})C(O)OR^{13}$, —$N(R^{12})S(O)_2R^{13}$, —$C(O)R^{13}$, —$OC(O)R^{13}$, —$C(O)N(R^{10})(R^{11})$, —$C(O)C(O)N(R^{10})(R^{11})$, —$S(O)R^{13}$, —$S(O)_2R^{13}$, and —$S(O)_2N(R^{10})(R^{11})$;

each $R^6$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^7$ is independently selected from hydrogen, $C_{1-6}$alkyl, and $C_{1-6}$haloalkyl;

each $R^8$ is independently selected from hydrogen, $C_{1-6}$alkyl, and $C_{1-6}$haloalkyl;

each $R^9$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl; and each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

or a pharmaceutically acceptable salt or solvate thereof.

In another embodiment is a compound of Formula (I), or a pharmaceutically acceptable salt thereof, wherein $R^1$ is selected from $C_{6-10}$aryl and $C_{1-9}$heteroaryl, wherein $C_{6-10}$aryl and $C_{1-9}$heteroaryl are optionally substituted with one, two, three, four, or five $R^4$. In another embodiment is a compound of Formula (I), or a pharmaceutically acceptable salt thereof, wherein $R^1$ is $C_{6-10}$aryl optionally substituted with one, two, three, four, or five $R^4$. In another embodiment is a compound of Formula (I), or a pharmaceutically acceptable salt thereof, wherein $R^1$ is phenyl optionally substituted with one, two, three, four, or five $R^4$. In another embodiment is a compound of Formula (I), or a pharmaceutically acceptable salt thereof, wherein $R^1$ is phenyl optionally substituted with one, two, or three $R^4$. In another embodiment is a compound of Formula (I), or a pharmaceutically acceptable salt thereof, wherein $R^1$ is $C_{1-9}$heteroaryl optionally substituted with one, two, three, four, or five $R^4$. In another embodiment is a compound of Formula (I), or a pharmaceutically acceptable salt thereof, wherein $R^1$ is pyridyl optionally substituted with one, two, three, four, or five $R^4$. In another embodiment is a compound of Formula (I), or a pharmaceutically acceptable salt thereof, wherein each $R^4$ is independently selected from halogen, —CN, $C_{1-6}$alkyl, $C_{1-6}$haloalkyl, —$OR^6$, —C(O)$OR^6$, —C(O)$R^9$, —C(O)N($R^6$)($R^7$), —S(O)$_2R^9$, and —S(O)$_2$N($R^6$)($R^7$). In another embodiment is a compound of Formula (I), or a pharmaceutically acceptable salt thereof, wherein each $R^4$ is independently selected from halogen, $C_{1-6}$alkyl, $C_{1-6}$haloalkyl, and —$OR^6$. In another embodiment is a compound of Formula (I), or a pharmaceutically acceptable salt thereof, wherein $R^2$ is $C_{3-8}$cycloalkyl optionally substituted with one, two, three, four, or five $R^5$. In another embodiment is a compound of Formula (I), or a pharmaceutically acceptable salt thereof, wherein $R^2$ is cyclohexyl optionally substituted with one, two, three, four, or five $R^5$. In another embodiment is a compound of Formula (I), or a pharmaceutically acceptable salt thereof, wherein $R^2$ is cyclohexyl optionally substituted with one, two, or three $R^5$. In another embodiment is a compound of Formula (I), or a pharmaceutically acceptable salt thereof, wherein $R^2$ is $C_{6-10}$aryl optionally substituted with one, two, three, four, or five $R^5$. In another embodiment is a compound of Formula (I), or a pharmaceutically acceptable salt thereof, wherein $R^2$ is phenyl optionally substituted with one, two, three, four, or five $R^5$. In another embodiment is a compound of Formula (I), or a pharmaceutically acceptable salt thereof, wherein $R^2$ is phenyl optionally substituted with one, two, or three $R^5$. In another embodiment is a compound of Formula (I), or a pharmaceutically acceptable salt thereof, wherein $R^2$ is $C_{2-9}$heterocycloalkyl optionally substituted with one, two, three, four, or five $R^5$. In another embodiment is a compound of Formula (I), or a pharmaceutically acceptable salt thereof, wherein $R^2$ is tetrahydropyranyl optionally substituted with one, two, or three $R^5$. In another embodiment is a compound of Formula (I), or a pharmaceutically acceptable salt thereof, wherein each $R^5$ is independently selected from halogen, —CN, $C_{1-6}$haloalkyl, —$OR^6$, —C(O)$OR^6$, —C(O)$R^9$, —C(O)N($R^6$)($R^7$), —S(O)$_2R^9$, —S(O)$_2$N($R^6$)($R^7$), and $C_{1-6}$alkyl optionally substituted with one, two, or three groups selected from —$OR^{10}$, —C(O)$OR^{10}$, —C(O)$R^{13}$, —C(O)N($R^{10}$)($R^{11}$), —S(O)$_2R^{13}$, and —S(O)$_2$N($R^{10}$)($R^{11}$). In another embodiment is a compound of Formula (I), or a pharmaceutically acceptable salt thereof, wherein each $R^5$ is independently selected from halogen, $C_{1-6}$haloalkyl, —$OR^6$, and $C_{1-6}$alkyl optionally substituted with one group selected from —$OR^{10}$, —C(O)$OR^{10}$, —C(O)N($R^{10}$)($R^{11}$), —S(O)$_2R^{13}$, and —S(O)$_2$N($R^{10}$)($R^{11}$). In another embodiment is a compound of Formula (I), or a pharmaceutically acceptable salt thereof, wherein each $R^5$ is independently selected from halogen, —$OR^6$, and $C_{1-6}$alkyl optionally substituted with one group selected from —$OR^{10}$, —C(O)$OR^{10}$, —C(O)N($R^{10}$)($R^{11}$), and —S(O)$_2R^{13}$. In another embodiment is a compound of Formula (I), or a pharmaceutically acceptable salt thereof, wherein each $R^6$ is independently selected from hydrogen and $C_{1-6}$alkyl optionally substituted with one, two, or three groups selected from halogen and hydroxy. In another embodiment is a compound of Formula (I), or a pharmaceutically acceptable salt thereof, wherein each $R^{10}$ is independently selected hydrogen, $C_{1-6}$alkyl, and $C_{1-6}$haloalkyl. In another embodiment is a compound of Formula (I), or a pharmaceutically acceptable salt thereof, wherein $R^3$ is $C_1$-$C_6$alkyl. In another embodiment is a compound of Formula (I), or a pharmaceutically acceptable salt thereof, wherein $R^3$ is hydrogen. In another embodiment is a compound of Formula (I), or a pharmaceutically acceptable salt thereof, wherein X is a bond. In another embodiment is a compound of Formula (I), or a pharmaceutically acceptable salt thereof, wherein X is $C_1$-$C_6$alkylene.

In another embodiment is a pharmaceutical composition comprising a compound of Formula (I) described herein, or a pharmaceutically acceptable salt thereof, and at least one pharmaceutically acceptable excipient.

In another embodiment is a method of treating cancer in a mammal in need thereof, comprising administering to the mammal a therapeutically effective amount of a compound of Formula (I) described herein, or a pharmaceutically acceptable salt thereof. In another embodiment is a method of treating cancer in a mammal in need thereof, comprising administering to the mammal a therapeutically effective amount of a compound of Formula (I) described herein, or a pharmaceutically acceptable salt thereof, wherein the cancer is selected from adrenocortical carcinoma, ovarian cancer, head and neck cancer, endometrial cancer, hormone-dependent prostate cancer, non-small cell lung carcinoma (NSCLC), melanoma, pituitary gonadotroph adenomas, and sex cord stromal tumors. In another embodiment is a method of treating cancer in a mammal in need thereof, comprising administering to the mammal a therapeutically effective amount of a compound of Formula (I) described herein, or a pharmaceutically acceptable salt thereof, wherein the cancer is adrenocortical carcinoma.

In another embodiment is a method of treating an endocrine disease in a mammal in need thereof, comprising administering to the mammal a therapeutically effective amount of a compound of Formula (I) described herein, or a pharmaceutically acceptable salt thereof. In another embodiment is a method of treating an endocrine disease in a mammal in need thereof, comprising administering to the mammal a therapeutically effective amount of a compound of Formula (I) described herein, or a pharmaceutically acceptable salt thereof, wherein the endocrine disease is selected from endogenous Cushing's syndrome, congenital adrenal hyperplasia, and polycystic ovary syndrome.

In another embodiment is a method of treating endometriosis in a mammal in need thereof, comprising administering to the mammal a therapeutically effective amount of a compound of Formula (I) described herein, or a pharmaceutically acceptable salt thereof.

DETAILED DESCRIPTION OF THE INVENTION

Steroidogenic factor 1 (SF-1, NR5A1) is a transcriptional regulator of genes involved in the development and function of steroidogenic tissues. Postnatally, SF-1 is expressed in the adrenal cortex and the gonads, in the pituitary gonadotrophs, in the ventromedial nucleus of the hypothalamus (VMH), and in the spleen vasculature.

Targeted deletion of the SF-1 gene in mice results in adrenal and gonadal agenesis and postnatal lethality due to severe adrenal insufficiency. In humans, partial loss-of-function mutations in SF-1 are associated with disorders of sexual development and severe adrenal insufficiency.

SF-1 plays an important role in steroid hormones synthesis by regulating the transcription of steroidogenic genes including StAR, Cyp11a1, Cyp17, CYP21, Cyp11b1, Cyp11b2 and 3β-Hsd. The transcriptional activity of SF-1 can be stimulated by the binding of adrenocorticotropic hormone (ACTH) to the melanocortin 2 receptor (MC2R) in the adrenal cortex.

The SF-1 protein has a modular domain structure comprised of an N-terminal zinc finger DNA-binding domain (DBD), a ligand-binding domain (LBD), a C-terminal AF-2 activation domain, and an intervening hinge region. SF-1 also contains a 30-amino acid extension of the DBD that mediates binding to a specific DNA recognition motif Unlike most other nuclear receptor transcription factors, SF-1 interacts with its DNA recognition motif as a monomer. SF-1 activity is modulated by phosphoinositides and other phospholipids that bind to a large hydrophobic pocket within the SF-1 LBD.

SF-1 is highly expressed in ectopic endometrial lesions, by at least 1,000-fold at the mRNA level and about 5-fold at the protein level, when compared to normal endometrium. Further, SF-1 expression is closely correlated with aromatase expression in endometriotic tissue, suggesting that SF-1 is an important regulatory factor for nitracrine estrogen biosynthesis.

Genomic, clinical, and pathologic studies implicate SF-1 as a key transcription factor in the pathogenesis of adrenocortical cancer (ACC). Higher levels of tumor SF-1 expression are correlated with higher risk of death in adult ACC. In pediatric ACC, SF-1 is overexpressed at the protein and/or chromosomal level in approximately 90% of cases. SF-1 is also highly expressed in sex cord-stromal tumors such (e.g. Sertoli cell tumors) and is ectopically expressed in a subset of ovarian serous carcinomas, head and neck cancers, and widely in endometriosis.

Postnatal deletion of SF-1 in the VMH leads to high fat diet induced obesity due to impaired thermogenesis and blunted leptin signaling suggesting that SF-1 is an important regulator of energy metabolism.

In addition, SF-1 antagonists may block pituitary gonadotroph release or suppress the production of adrenal steroids, including cortisol or the adrenal androgens. Potential indications include hormone-dependent prostate cancer, endogenous Cushing's syndrome, congenital adrenal hyperplasia, and polycystic ovary syndrome among other diseases of endocrine dysfunction.

SF-1 antagonists may be a promising avenue for new therapeutic compounds.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

"Amino" refers to the —$NH_2$ radical.

"Cyano" refers to the —CN radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Alkyl" or "alkylene" refers to a straight or branched hydrocarbon chain radical consisting solely of carbon and hydrogen atoms, containing no unsaturation, having from one to eighteen carbon atoms (e.g., $C_1$-$C_{18}$ alkyl). In certain embodiments, an alkyl comprises three to eighteen carbon atoms (e.g., $C_3$-$C_{18}$ alkyl). In certain embodiments, an alkyl comprises one to fifteen carbon atoms (e.g., $C_1$-$C_{15}$ alkyl). In certain embodiments, an alkyl comprises one to twelve carbon atoms (e.g., $C_1$-$C_{12}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)-$R^f$, —$N(R^a)_2$, —C(O)$R^a$, —C(O)$OR^a$, —C(O)N$(R^a)_2$, —N($R^a$)C(O)$OR^f$, —OC(O)—N$R^aR^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N$(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to eighteen carbon atoms. In certain embodiments, an alkenyl comprises three to eighteen carbon atoms. In certain embodiments, an alkenyl comprises three to twelve carbon atoms. In certain embodiments, an alkenyl comprises six to twelve carbon atoms. In certain embodiments, an alkenyl comprises six to ten carbon atoms. In certain embodiments, an alkenyl comprises eight to ten carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)-$R^f$, —$N(R^a)_2$, —C(O)$R^a$, —C(O)O$R^a$, —C(O)$N(R^a)_2$, —$N(R^a)$C(O)O$R^f$, —OC(O)—N$R^aR^f$, —$N(R^a)$C(O)$R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to eighteen carbon atoms. In certain embodiments, an alkynyl comprises three to eighteen carbon atoms. In certain embodiments, an alkynyl comprises three to twelve carbon atoms. In certain embodiments, an alkynyl comprises six to twelve carbon atoms. In certain embodiments, an alkynyl comprises six to ten carbon atoms. In certain embodiments, an alkynyl comprises eight to ten carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)-$R^f$, —$N(R^a)_2$, —C(O)$R^a$, —C(O)O$R^a$, —C(O)$N(R^a)_2$, —$N(R^a)$C(O)O$R^f$, —OC(O)—N$R^aR^f$, —$N(R^a)$C(O)$R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, -$R^b$-O$R^a$, -$R^b$-OC(O)-$R^a$, -$R^b$-OC(O)—O$R^a$, -$R^b$-OC(O)—$N(R^a)_2$, -$R^b$-$N(R^a)_2$, -$R^b$-C(O)$R^a$, -$R^b$-C(O)O$R^a$, -$R^b$-C(O)$N(R^a)_2$, -$R^b$-O-$R^c$—C(O)$N(R^a)_2$, -$R^b$-$N(R^a)$C(O)O$R^a$, -$R^b$-$N(R^a)$C(O)$R^a$, -$R^b$-$N(R^a)S(O)_tR^a$ (where t is 1 or 2), -$R^b$-S(O)O$R^a$ (where t is 1 or 2), -$R^b$-$S(O)_tR^a$ (where t is 1 or 2), and -$R^b$-$S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula -$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula -$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula -$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term “cycloalkyl” is meant to include cycloalkyl radicals that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)—OR^a$, $-R^b-OC(O)—N(R^a)_2$, $-R^b-N(R^a)_2$, $-R^b-C(O)R^a$, $—R^b-C(O)OR^a$, $-R^b-C(O)N(R^a)_2$, $-R^b-O-R^c—C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2), and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

“Halo” or “halogen” refers to bromo, chloro, fluoro or iodo substituents.

“Haloalkyl” refers to an alkyl radical, as defined above, that is substituted by one or more halo radicals, as defined above.

“Haloalkoxy” refers to an alkoxy radical, as defined above, that is substituted by one or more halo radicals, as defined above.

“Fluoroalkyl” refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

“Heterocycloalkyl” refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term “heterocycloalkyl” is meant to include heterocycloalkyl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)—OR^a$, $-R^b-OC(O)—N(R^a)_2$, $-R^b-N(R^a)_2$, $-R^b-C(O)R^a$, $-R^b-C(O)OR^a$, $-R^b-C(O)N(R^a)_2$, $-R^b-O-R^c—C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)OR^a$ (where t is 1 or 2), $-R^b-S(O)R^a$ (where t is 1 or 2), and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

“Heteroaryl” refers to a radical derived from a 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term “heteroaryl” is meant to include heteroaryl radicals as defined above which are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)—OR^a$, $-R^b-OC(O)—N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2), and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

“N-heteroaryl” refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

“C-heteroaryl” refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

“Heteroaryloxy” refers to radical bonded through an oxygen atom of the formula —O-heteroaryl, where heteroaryl is as defined above.

“Heteroarylalkyl” refers to a radical of the formula $-R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

“Heteroarylalkoxy” refers to a radical bonded through an oxygen atom of the formula —O-R-heteroaryl, where R is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain.

The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fuimarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic

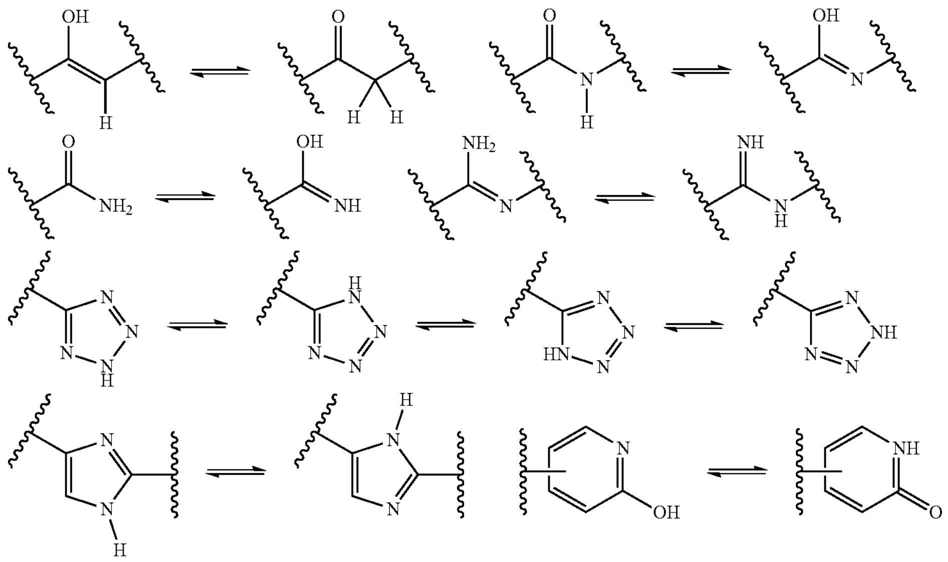

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I) described herein are SF-1 modulators. In some embodiments, the compounds of Formula (I) described herein are SF-1 antagonists. In some embodiments, the compounds of Formula (I) described herein, and compositions comprising these compounds, are SF-1 antagonists useful for the treatment of cancer.

In some embodiments is a compound of Formula (I):

Formula (I)

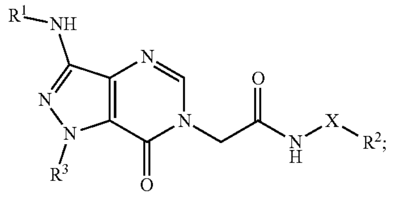

wherein:

X is a bond or $C_1$-$C_6$alkylene;

$R^1$ is selected from $C_{3-8}$cycloalkyl, $C_{2-9}$heterocycloalkyl, —$CH_2C_{6-10}$aryl, $C_{6-10}$aryl, and $C_{1-9}$heteroaryl, wherein $C_{3-8}$cycloalkyl, $C_{2-9}$heterocycloalkyl, —$CH_2C_{6-10}$aryl, $C_{6-10}$aryl and $C_{1-9}$heteroaryl are optionally substituted with one, two, three, four, or five $R^4$;

$R^2$ is selected from $C_{3-8}$cycloalkyl, $C_{2-9}$heterocycloalkyl, $C_{6-10}$aryl and $C_{1-9}$heteroaryl, wherein $C_{3-8}$cycloalkyl, $C_{2-9}$heterocycloalkyl, $C_{6-10}$aryl and $C_{1-9}$heteroaryl are optionally substituted with one, two, three, four, or five $R^5$;

$R^3$ is hydrogen, $C_1$-$C_6$alkyl, $C_1$-$C_6$haloalkyl, or $C_{3-8}$cycloalkyl;

each $R^4$ and each $R^5$ are each independently selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^6$, —$SR^6$, —$C(O)OR^6$, —$OC(O)N(R^6)(R^7)$, —$N(R^8)C(O)N(R^6)(R^7)$, —$N(R^8)C(O)R^9$, —$N(R^8)C(O)OR^9$, —$N(R^8)S(O)_2R^9$, —$C(O)R^9$, —$OC(O)R^9$, —$C(O)N(R^6)(R^7)$, —$C(O)C(O)N(R^6)(R^7)$, —$S(O)R^9$, —$S(O)_2R^9$, and —$S(O)_2N(R^6)(R^7)$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$C(O)OR^{10}$, —$OC(O)N(R^{10})(R^{11})$, —$N(R^{12})C(O)N(R^{10})(R^{11})$, —$N(R^{12})C(O)R^{13}$, —$N(R^{12})C(O)OR^{13}$, —$N(R^{12})S(O)_2R^{13}$, —$C(O)R^{13}$, —$OC(O)R^{13}$, —$C(O)N(R^{10})(R^{11})$, —$C(O)C(O)N(R^{10})(R^{11})$, —$S(O)R^{13}$, —$S(O)_2R^{13}$, and —$S(O)_2N(R^{10})(R^{11})$;

each $R^6$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^7$ is independently selected from hydrogen, $C_{1-6}$alkyl, and $C_{1-6}$haloalkyl;

each $R^8$ is independently selected from hydrogen, $C_{1-6}$alkyl, and $C_{1-6}$haloalkyl;

each $R^9$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl; and each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

or a pharmaceutically acceptable salt or solvate thereof.

In another embodiment is a compound of Formula (I), or a pharmaceutically acceptable salt thereof, wherein $R^1$ is $C_{6-10}$aryl optionally substituted with one, two, three, four, or five $R^4$. In another embodiment is a compound of Formula (I), or a pharmaceutically acceptable salt thereof, wherein $R^1$ is phenyl optionally substituted with one, two, three, four, or five $R^4$. In another embodiment is a compound of Formula (I), or a pharmaceutically acceptable salt thereof, wherein $R^1$ is phenyl optionally substituted with one, two, or three $R^4$. In another embodiment is a compound of Formula (I), or a pharmaceutically acceptable salt thereof, wherein $R^1$ is phenyl optionally substituted with one, two, or three $R^4$, wherein each $R^4$ is independently selected from halogen, —CN, $C_{1-6}$alkyl, $C_{1-6}$haloalkyl, —$OR^6$, —$C(O)OR^6$, —$C(O)R^9$, —$C(O)N(R^6)(R^7)$, —$S(O)_2R^9$, and —$S(O)_2N(R^6)(R^7)$. In another embodiment is a compound of Formula (I), or a pharmaceutically acceptable salt thereof, wherein $R^1$ is phenyl optionally substituted with one or two $R^4$, wherein each $R^4$ is independently selected from halogen, —CN, $C_{1-6}$alkyl, $C_{1-6}$haloalkyl, —$OR^6$, —$C(O)OR^6$, —$C(O)R^9$, —$C(O)N(R^6)(R^7)$, —$S(O)_2R^9$, and —$S(O)_2N(R^6)(R^7)$. In another embodiment is a compound of Formula (I), or a pharmaceutically acceptable salt thereof, wherein $R^1$ is phenyl optionally substituted with one $R^4$, wherein $R^4$ is selected from halogen, —CN, $C_{1-6}$alkyl, $C_{1-6}$haloalkyl, —$OR^6$, —$C(O)OR^6$, —$C(O)R^9$, —$C(O)N(R^6)(R^7)$, —$S(O)_2R^9$, and —$S(O)_2N(R^6)(R^7)$. In another embodiment is a compound of Formula (I), or a pharmaceutically acceptable salt thereof, wherein $R^1$ is phenyl optionally substituted with one, two, or three $R^4$, wherein each $R^4$ is independently selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is phenyl optionally substituted with one or two $R^4$, wherein each $R^4$ is independently selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is phenyl substituted with one or two $R^4$, wherein each $R^4$ is independently selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is phenyl optionally substituted with one $R^4$, wherein $R^4$ is selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is phenyl substituted with one $R^4$, wherein $R^4$ is selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is phenyl substituted with one $R^4$, wherein $R^4$ is $C_{1-6}$haloalkyl. In another embodiment is a compound of Formula (I), or a pharmaceutically acceptable salt thereof, wherein $R^1$ is phenyl substituted with one $R^4$, wherein $R^4$ is halogen. In another embodiment is a compound of Formula (I), or a pharmaceutically acceptable salt thereof, wherein $R^1$ is phenyl substituted with one $R^4$, wherein $R^4$ is $C_{1-6}$alkyl. In another embodiment is a compound of Formula (I), or a pharmaceutically acceptable salt thereof, wherein $R^1$ is phenyl substituted with one $R^4$, wherein $R^4$ is —$OR^6$.

In another embodiment is a compound of Formula (I), or a pharmaceutically acceptable salt thereof, wherein $R^1$ is unsubstituted phenyl.

In another embodiment is a compound of Formula (I), or a pharmaceutically acceptable salt thereof, wherein $R^1$ is $C_{1-9}$heteroaryl optionally substituted with one, two, or three $R^4$. In another embodiment is a compound of Formula (I), or a pharmaceutically acceptable salt thereof, wherein $R^1$ is $C_{1-9}$heteroaryl optionally substituted with one, two, or three $R^4$, wherein each $R^4$ is independently selected from halogen, —CN, $C_{1-6}$alkyl, $C_{1-6}$haloalkyl, —$OR^6$, —$C(O)OR^6$, —$C(O)R^9$, —$C(O)N(R^6)(R^7)$, —$S(O)_2R^9$, and —$S(O)_2N(R^6)(R^7)$. In another embodiment is a compound of Formula (I), or a pharmaceutically acceptable salt thereof, wherein $R^1$ is $C_{1-9}$heteroaryl optionally substituted with one or two $R^4$, wherein each $R^4$ is independently selected from halogen, —CN, $C_{1-6}$alkyl, $C_{1-6}$haloalkyl, —$OR^6$, —$C(O)OR^6$, —$C(O)R^9$, —$C(O)N(R^6)(R^7)$, —$S(O)_2R^9$, and —$S(O)_2N(R^6)(R^7)$. In another embodiment is a compound of Formula (I), or a pharmaceutically acceptable salt thereof, wherein $R^1$ is $C_{1-9}$heteroaryl optionally substituted with one $R^4$, wherein $R^4$ is selected from halogen, —CN, $C_{1-6}$alkyl, $C_{1-6}$haloalkyl, —$OR^6$, —$C(O)OR^6$, —$C(O)R^9$, —$C(O)N(R^6)(R^7)$, —$S(O)_2 R^9$, and —$S(O)_2N(R^6)(R^7)$. In another embodiment is a compound of Formula (I), or a pharmaceutically acceptable salt thereof, wherein $R^1$ is $C_{1-9}$heteroaryl optionally substituted with one, two, or three $R^4$, wherein each $R^4$ is independently selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is $C_{1-9}$heteroaryl optionally substituted with one or two $R^4$, wherein each $R^4$ is independently selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is $C_{1-9}$heteroaryl substituted with one or two $R^4$, wherein each $R^4$ is independently selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is $C_{1-9}$heteroaryl optionally substituted with one $R^4$, wherein $R^4$ is selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is $C_{1-9}$heteroaryl substituted with one $R^4$, wherein $R^4$ is selected from halogen, $C_{1-6}$alkyl, $C_{1-6}$haloalkyl, and —$OR^6$. In another embodiment is a compound of Formula (I), or a pharmaceutically acceptable salt thereof, wherein $R^1$ is $C_{1-9}$heteroaryl substituted with one $R^4$, wherein $R^4$ is $C_{1-6}$haloalkyl. In another embodiment is a compound of Formula (I), or a pharmaceutically acceptable salt thereof, wherein $R^1$ is $C_{1-9}$heteroaryl substituted with one $R^4$, wherein $R^4$ is halogen. In another embodiment is a compound of Formula (I), or a pharmaceutically acceptable salt thereof, wherein $R^1$ is $C_{1-9}$heteroaryl substituted with one $R^4$, wherein $R^4$ is $C_{1-6}$alkyl. In another embodiment is a compound of Formula (I), or a pharmaceutically acceptable salt thereof, wherein $R^1$ is $C_{1-9}$heteroaryl substituted with one $R^4$, wherein $R^4$ is —$OR^6$. In some embodiments of a compound of Formula (I) described herein wherein $R^1$ is $C_{1-9}$heteroaryl, the $C_{1-9}$heteroaryl is pyridyl.

In another embodiment is a compound of Formula (I), or a pharmaceutically acceptable salt thereof, wherein $R^1$ is unsubstituted $C_{1-9}$heteroaryl. In another embodiment is a compound of Formula (I), or a pharmaceutically acceptable salt thereof, wherein $R^1$ is unsubstituted pyridyl.

In another embodiment is a compound of Formula (I), or a pharmaceutically acceptable salt thereof, wherein $R^1$ is —$CH_2C_{6-10}$aryl optionally substituted with one, two, or three $R^4$. In another embodiment is a compound of Formula (I), or a pharmaceutically acceptable salt thereof, wherein $R^1$ is benzyl optionally substituted with one, two, or three $R^4$. In another embodiment is a compound of Formula (I), or a pharmaceutically acceptable salt thereof, wherein $R^1$ is unsubstituted benzyl.

In another embodiment is a compound of Formula (I), or a pharmaceutically acceptable salt thereof, wherein $R^1$ is $C_{2-9}$heterocycloalkyl optionally substituted with one, two, or three $R^4$. In another embodiment is a compound of Formula (I), or a pharmaceutically acceptable salt thereof, wherein $R^1$ is unsubstituted $C_{2-9}$heterocycloalkyl.

In another embodiment is a compound of Formula (I), or a pharmaceutically acceptable salt thereof, wherein $R^1$ is $C_{3-8}$cycloalkyl optionally substituted with one, two, or three $R^4$. In another embodiment is a compound of Formula (I), or a pharmaceutically acceptable salt thereof, wherein $R^1$ is unsubstituted $C_{3-8}$cycloalkyl.

In another embodiment is a compound of Formula (I), or a pharmaceutically acceptable salt thereof, wherein $R^2$ is $C_{3-8}$cycloalkyl optionally substituted with one, two, three, four, or five $R^5$. In another embodiment is a compound of Formula (I), or a pharmaceutically acceptable salt thereof, wherein $R^2$ is cyclohexyl optionally substituted with one, two, three, four, or five $R^5$. In another embodiment is a compound of Formula (I), or a pharmaceutically acceptable salt thereof, wherein $R^2$ is cyclohexyl optionally substituted with one, two, or three $R^5$. In another embodiment is a compound of Formula (I), or a pharmaceutically acceptable salt thereof, wherein $R^2$ is cyclohexyl optionally substituted with one, two, or three $R^5$ and each $R^5$ is independently selected from halogen, —CN, $C_{1-6}$haloalkyl, —$OR^6$, —$C(O)OR^6$, —$C(O)R^9$, —$C(O)N(R^6)(R^7)$, —$S(O)_2R^9$, —$S(O)_2N(R^6)(R^7)$, and $C_{1-6}$alkyl optionally substituted with one, two, or three groups selected from —$OR^{10}$, —$C(O)OR^{10}$, —$C(O)R^{13}$, —$C(O)N(R^{10})(R^{11})$, —$S(O)_2R^{13}$, and —$S(O)_2N(R^{10})(R^{11})$. In another embodiment is a compound of Formula (I), or a pharmaceutically acceptable salt thereof, wherein $R^2$ is cyclohexyl optionally substituted with one, two, or three $R^5$ and each $R^5$ is independently selected from halogen, $C_{1-6}$haloalkyl, —$OR^6$, and $C_{1-6}$alkyl optionally substituted with one group selected from —$OR^{10}$, —$C(O)OR^{10}$, —$C(O)N(R^{10})(R^{11})$, —$S(O)_2R^{13}$, and —$S(O)_2$ $N(R^{10})(R^{11})$. In another embodiment is a compound of Formula (I), or a pharmaceutically acceptable salt thereof, wherein $R^2$ is cyclohexyl optionally substituted with one, two, or three $R^5$ and each $R^5$ is independently selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is cyclohexyl optionally substituted with one or two $R^5$ and each $R^5$ is independently selected from halogen, —$OR^6$, and $C_{1-6}$alkyl optionally substituted with one group selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is cyclohexyl optionally substituted with one $R^5$ and $R^5$ is selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is cyclohexyl substituted with one $R^5$ and $R^5$ is selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is cyclohexyl substituted with one $R^5$ and $R^5$ is —$OR^6$. In another embodiment is a compound of Formula (I), or a pharmaceutically acceptable salt thereof, wherein $R^2$ is cyclohexyl substituted with one $R^5$, $R^5$ is —$OR^6$, and $R^6$ is selected from hydrogen and $C_{1-6}$alkyl optionally substituted with one, two, or three groups selected from halogen and hydroxy. In another embodiment is a compound of Formula (I), or a pharmaceutically acceptable salt thereof, wherein $R^2$ is cyclohexyl substituted with one $R^5$, $R^5$ is —$OR^6$, and $R^6$ is hydrogen. In another embodiment is a compound of Formula (I), or a pharmaceutically acceptable salt thereof, wherein $R^2$ is cyclohexyl substituted with one $R^5$, $R^5$ is —$OR^6$, and $R^6$ is $C_{1-6}$alkyl substituted with one, two, or three halogen. In another embodiment is a compound of Formula (I), or a pharmaceutically acceptable salt thereof, wherein $R^2$ is cyclohexyl substituted with one $R^5$, $R^5$ is —$OR^6$, and $R^6$ is $C_{1-6}$alkyl substituted with one hydroxy. In another embodiment is a compound of Formula (I), or a pharmaceutically acceptable salt thereof, wherein $R^2$ is cyclohexyl substituted with one $R^5$, $R^5$ is —$OR^6$, and $R^6$ is unsubstituted $C_{1-6}$alkyl. In another embodiment is a compound of Formula (I), or a pharmaceutically acceptable salt thereof, wherein $R^2$ is cyclohexyl substituted with one $R^5$ and $R^5$ is $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is cyclohexyl substituted with one $R^5$, $R^5$ is $C_{1-6}$alkyl optionally substituted with one group selected from —$OR^{10}$, —$C(O)OR^{10}$, and —$C(O)N(R^{10})(R^{11})$, and $R^{10}$ is selected from hydrogen, $C_{1-6}$alkyl, and $C_{1-6}$haloalkyl. In another embodiment is a compound of Formula (I), or a pharmaceutically acceptable salt thereof, wherein $R^2$ is cyclohexyl substituted with one $R^5$, $R^5$ is $C_{1-6}$alkyl substituted with —$OR^{10}$, and $R^{10}$ is hydrogen. In another embodiment is a compound of Formula (I), or a pharmaceutically acceptable salt thereof, wherein $R^2$ is cyclohexyl substituted with one $R^5$, $R^5$ is $C_{1-6}$alkyl substituted with —$OR^{10}$, and $R^{10}$ is $C_{1-6}$alkyl. In another embodiment is a compound of Formula (I), or a pharmaceutically acceptable salt thereof, wherein $R^2$ is cyclohexyl substituted with one $R^5$, $R^5$ is $C_{1-6}$alkyl substituted with —$C(O)OR^{10}$, and $R^{10}$ is hydrogen. In another embodiment is a compound of Formula (I), or a pharmaceutically acceptable salt thereof, wherein $R^2$ is cyclohexyl substituted with one $R^5$, $R^5$ is $C_{1-6}$alkyl substituted with —$C(O)OR^{10}$, and $R^{10}$ is $C_{1-6}$alkyl. In another embodiment is a compound of Formula (I), or a pharmaceutically acceptable salt thereof, wherein $R^2$ is unsubstituted cyclohexyl.

In another embodiment is a compound of Formula (I), or a pharmaceutically acceptable salt thereof, wherein $R^2$ is $C_{6-10}$aryl optionally substituted with one, two, three, four, or five $R^5$. In another embodiment is a compound of Formula (I), or a pharmaceutically acceptable salt thereof, wherein $R^2$ is phenyl optionally substituted with one, two, three, four, or five $R^5$. In another embodiment is a compound of Formula (I), or a pharmaceutically acceptable salt thereof, wherein $R^2$ is phenyl optionally substituted with one, two, or three $R^5$. In another embodiment is a compound of Formula (I), or a pharmaceutically acceptable salt thereof, wherein $R^2$ is phenyl optionally substituted with one, two, or three $R^5$ and each $R^5$ is independently selected from halogen, —CN, $C_{1-6}$haloalkyl, —$OR^6$, —$C(O)OR^6$, —$C(O)R^9$, —$C(O)N(R^6)(R^7)$, —$S(O)_2R^9$, —$S(O)_2N(R^6)(R^7)$, and $C_{1-6}$alkyl optionally substituted with one, two, or three groups selected from —$OR^{10}$, —$C(O)OR^{10}$, —$C(O)R^3$, —$C(O)N(R^{10})(R^{11})$, —$S(O)_2R^3$, and —$S(O)_2N(R^{10})(R^{11})$. In another embodiment is a compound of Formula (I), or a pharmaceutically acceptable salt thereof, wherein $R^2$ is phenyl optionally substituted with one, two, or three $R^5$ and each $R^5$ is independently selected from halogen, $C_{1-6}$haloalkyl, —$OR^6$, and $C_{1-6}$alkyl optionally substituted with one group selected from —$OR^{10}$, —$C(O)OR^{10}$, —$C(O)N(R^{10})(R^{11})$, —$S(O)_2R^{13}$, and —$S(O)_2N(R^{10})(R^{11})$. In another embodiment is a compound of Formula (I), or a pharmaceutically acceptable salt thereof, wherein $R^2$ is phenyl optionally substituted with one, two, or three $R^5$ and each $R^5$ is independently selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is phenyl optionally substituted with one or two $R^5$ and each $R^5$ is independently selected from halogen, —$OR^6$, and $C_{1-6}$alkyl optionally substituted with one group selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is phenyl optionally substituted with one $R^5$ and $R^5$ is selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is phenyl substituted with one $R^5$ and $R^5$ is selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is phenyl substituted with one $R^5$ and $R^5$ is —$OR^6$. In another embodiment is a compound of Formula (I), or a pharmaceutically acceptable salt thereof, wherein $R^2$ is phenyl substituted with one $R^5$, $R^5$ is —$OR^6$, and $R^6$ is selected from hydrogen and $C_{1-6}$alkyl optionally substituted with one, two, or three groups selected from halogen and hydroxy. In another embodiment is a compound of Formula (I), or a pharmaceutically acceptable salt thereof, wherein $R^2$ is phenyl substituted with one $R^5$, $R^5$ is —$OR^6$, and $R^6$ is hydrogen. In another embodiment is a compound of Formula (I), or a pharmaceutically acceptable salt thereof, wherein $R^2$ is phenyl substituted with one $R^5$, $R^5$ is —$OR^6$, and $R^6$ is $C_{1-6}$alkyl substituted with one, two, or three halogen. In another embodiment is a compound of Formula (I), or a pharmaceutically acceptable salt thereof, wherein $R^2$ is phenyl substituted with one $R^5$, $R^5$ is —$OR^6$, and $R^6$ is $C_{1-6}$alkyl substituted with one hydroxy. In another embodiment is a compound of Formula (I), or a pharmaceutically acceptable salt thereof, wherein $R^2$ is phenyl substituted with one $R^5$, $R^5$ is —$OR^6$, and $R^6$ is unsubstituted $C_{1-6}$alkyl. In another embodiment is a compound of Formula (I), or a pharmaceutically acceptable salt thereof, wherein $R^2$ is phenyl substituted with one $R^5$ and $R^5$ is $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is phenyl substituted with one $R^5$, $R^5$ is $C_{1-6}$alkyl optionally substituted with one group selected from —$OR^{10}$, —$C(O)OR^{10}$, and —$C(O)N(R^{10})(R^{11})$, and $R^{10}$ is selected from hydrogen, $C_{1-6}$alkyl, and $C_{1-6}$haloalkyl. In another embodiment is a compound of Formula (I), or a pharmaceutically acceptable salt thereof, wherein $R^2$ is phenyl substituted with one $R^5$, $R^5$ is $C_{1-6}$alkyl substituted with —$OR^{10}$, and $R^{10}$ is hydrogen. In another embodiment is a compound of Formula (I), or a pharmaceutically acceptable salt thereof, wherein $R^2$ is phenyl substituted with one $R^5$, $R^5$ is $C_{1-6}$alkyl substituted with —$OR^{10}$, and $R^{10}$ is $C_{1-6}$alkyl. In another embodiment is a compound of Formula (I), or a pharmaceutically acceptable salt thereof, wherein $R^2$ is phenyl substituted with one $R^5$, $R^5$ is $C_{1-6}$alkyl substituted with —$C(O)OR^{10}$, and $R^{10}$ is hydrogen. In another embodiment is a compound of Formula (I), or a pharmaceutically acceptable salt thereof, wherein $R^2$ is phenyl substituted with one $R^5$, $R^5$ is $C_{1-6}$alkyl substituted with —$C(O)OR^{10}$, and $R^{10}$ is $C_{1-6}$alkyl. In another embodiment is a compound of Formula (I), or a pharmaceutically acceptable salt thereof, wherein $R^2$ is unsubstituted phenyl.

In another embodiment is a compound of Formula (I), or a pharmaceutically acceptable salt thereof, wherein $R^2$ is $C_{2-9}$heterocycloalkyl optionally substituted with one, two, three, four, or five $R^5$. In another embodiment is a compound of Formula (I), or a pharmaceutically acceptable salt thereof, wherein $R^2$ is $C_{2-9}$heterocycloalkyl optionally substituted with one, two, three, four, or five $R^5$. In another embodiment is a compound of Formula (I), or a pharmaceutically acceptable salt thereof, wherein $R^2$ is $C_{2-9}$heterocycloalkyl optionally substituted with one, two, or three $R^5$. In another embodiment is a compound of Formula (I), or a pharmaceutically acceptable salt thereof, wherein $R^2$ is $C_{2-9}$heterocycloalkyl optionally substituted with one, two, or three $R^5$ and each $R^5$ is independently selected from halogen, —CN, $C_{1-6}$haloalkyl, —$OR^6$, —$C(O)OR^6$, —$C(O)R^9$, —$C(O)N(R^6)(R^7)$, —$S(O)_2R^9$, —$S(O)_2N(R^6)(R^7)$, and $C_{1-6}$alkyl optionally substituted with one, two, or three groups selected from —$OR^{10}$, —$C(O)OR^{10}$, —$C(O)R^{13}$, —$C(O)N(R^{10})(R^{11})$, —$S(O)_2R^{13}$, and —$S(O)_2N(R^{10})(R^{11})$. In another embodiment is a compound of Formula (I), or a pharmaceutically acceptable salt thereof, wherein $R^2$ is $C_{2-9}$heterocycloalkyl optionally substituted with one, two, or three $R^5$ and each $R^5$ is independently selected from halogen, $C_{1-6}$haloalkyl, —$OR^6$, and $C_{1-6}$alkyl optionally substituted with one group selected from —$OR^{10}$, —$C(O)OR^{10}$, —$C(O)N(R^{10})(R^{11})$, —$S(O)_2R^{13}$, and —$S(O)_2N(R^{10})(R^{11})$. In another embodiment is a compound of Formula (I), or a pharmaceutically acceptable salt thereof, wherein $R^2$ is $C_{2-9}$heterocycloalkyl optionally substituted with one, two, or three $R^5$ and each $R^5$ is independently selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{2-9}$heterocycloalkyl optionally substituted with one or two $R^5$ and each $R^5$ is independently selected from halogen, —$OR^6$, and $C_{1-6}$alkyl optionally substituted with one group selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{2-9}$heterocycloalkyl optionally substituted with one $R^5$ and $R^5$ is selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{2-9}$heterocycloalkyl substituted with one $R^5$ and $R^5$ is selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{2-9}$heterocycloalkyl substituted with one $R^5$ and $R^5$ is —$OR^6$. In another embodiment is a compound of Formula (I), or a pharmaceutically acceptable salt thereof, wherein $R^2$ is $C_{2-9}$heterocycloalkyl substituted with one $R^5$, $R^5$ is —$OR^6$, and $R^6$ is selected from hydrogen and $C_{1-6}$alkyl optionally substituted with one, two, or three groups selected from halogen and hydroxy. In another embodiment is a compound of Formula (I), or a pharmaceutically acceptable salt thereof, wherein $R^2$ is $C_{2-9}$heterocycloalkyl substituted with one $R^5$, $R^5$ is —$OR^6$, and $R^6$ is hydrogen. In another embodiment is a compound of Formula (I), or a pharmaceutically acceptable salt thereof, wherein $R^2$ is $C_{2-9}$heterocycloalkyl substituted with one $R^5$, $R^5$ is —$OR^6$, and $R^6$ is $C_{1-6}$alkyl substituted with one, two, or three halogen. In another embodiment is a compound of Formula (I), or a pharmaceutically acceptable salt thereof, wherein $R^2$ is $C_{2-9}$heterocycloalkyl substituted with one $R^5$, $R^5$ is —$OR^6$, and $R^6$ is $C_{1-6}$alkyl substituted with one hydroxy. In another embodiment is a compound of Formula (I), or a pharmaceutically acceptable salt thereof, wherein $R^2$ is $C_{2-9}$heterocycloalkyl substituted with one $R^5$, $R^5$ is —$OR^6$, and $R^6$ is unsubstituted $C_{1-6}$alkyl. In another embodiment is a compound of Formula (I), or a pharmaceutically acceptable salt thereof, wherein $R^2$ is $C_{2-9}$heterocycloalkyl substituted with one $R^5$ and $R^5$ is $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{2-9}$heterocycloalkyl substituted with one $R^5$, $R^5$ is $C_{1-6}$alkyl optionally substituted with one group selected from —$OR^{10}$, —$C(O)OR^{10}$, and —$C(O)N(R^{10})(R^{11})$, and $R^{10}$ is selected from hydrogen, $C_{1-6}$alkyl, and $C_{1-6}$haloalkyl. In another embodiment is a compound of Formula (I), or a pharmaceutically acceptable salt thereof, wherein $R^2$ is $C_{2-9}$heterocycloalkyl substituted with one $R^5$, $R^5$ is $C_{1-6}$alkyl substituted with —$OR^{10}$, and $R^{10}$ is hydrogen. In another embodiment is a compound of Formula (I), or a pharmaceutically acceptable salt thereof, wherein $R^2$ is $C_{2-9}$heterocycloalkyl substituted with one $R^5$, $R^5$ is $C_{1-6}$alkyl substituted with —$OR^{10}$, and $R^{10}$ is $C_{1-6}$alkyl. In another embodiment is a compound of Formula (I), or a pharmaceutically acceptable salt thereof, wherein $R^2$ is $C_{2-9}$heterocycloalkyl substituted with one $R^5$, $R^5$ is $C_{1-6}$alkyl substituted with —$C(O)OR^{10}$, and $R^{10}$ is hydrogen. In another embodiment is a compound of Formula (I), or a pharmaceutically acceptable salt thereof, wherein $R^2$ is $C_{2-9}$heterocycloalkyl substituted with one $R^5$, $R^5$ is $C_{1-6}$alkyl substituted with —$C(O)OR^{10}$, and $R^{10}$ is $C_{1-6}$alkyl. In another embodiment is a compound of Formula (I), or a pharmaceutically acceptable salt thereof, wherein $R^2$ is unsubstituted $C_{2-9}$heterocycloalkyl. In some embodiments of a compound of Formula (I) described herein wherein $R^2$ is $C_{2-9}$heterocycloalkyl, the $C_{2-9}$heterocycloalkyl is tetrahydropyranyl.

In another embodiment is a compound of Formula (I), or a pharmaceutically acceptable salt thereof, wherein $R^2$ is $C_{1-9}$heteroaryl optionally substituted with one, two, or three $R^5$. In another embodiment is a compound of Formula (I), or a pharmaceutically acceptable salt thereof, wherein $R^2$ is $C_{1-9}$heteroaryl optionally substituted with one, two, or three $R^5$ and each $R^5$ is independently selected from halogen, —CN, $C_{1-6}$haloalkyl, —$OR^6$, —$C(O)OR^6$, —$C(O)R^9$, —$C(O)N(R^6)(R^7)$, —$S(O)_2R^9$, —$S(O)_2N(R^6)(R^7)$, and $C_{1-6}$alkyl optionally substituted with one, two, or three groups selected from —$OR^{10}$, —$C(O)OR^{10}$, —$C(O)R^{13}$, —$C(O)N(R^{10})(R^{11})$, —$S(O)_2R^{13}$, and —$S(O)_2N(R^{10})(R^{11})$. In another embodiment is a compound of Formula (I), or a pharmaceutically acceptable salt thereof, wherein $R^2$ is $C_{1-9}$heteroaryl optionally substituted with one, two, or three $R^5$ and each $R^5$ is independently selected from halogen, $C_{1-6}$haloalkyl, —$OR^6$, and $C_{1-6}$alkyl optionally substituted with one group selected from —$OR^{10}$, —$C(O)OR^{10}$, —$C(O)N(R^{10})(R^{11})$, —$S(O)_2R^{13}$, and —$S(O)_2N(R^{10})(R^{11})$. In another embodiment is a compound of Formula (I), or a pharmaceutically acceptable salt thereof, wherein $R^2$ is $C_{1-9}$heteroaryl optionally substituted with one, two, or three $R^5$ and each $R^5$ is independently selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{1-9}$heteroaryl optionally substituted with one or two $R^5$ and each $R^5$ is independently selected from halogen, —$OR^6$, and $C_{1-6}$alkyl optionally substituted with one group selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{1-9}$heteroaryl optionally substituted with one $R^5$ and $R^5$ is selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{1-9}$heteroaryl substituted with one $R^5$ and $R^5$ is selected from halogen, —$OR^6$, and $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{1-9}$heteroaryl substituted with one $R^5$ and $R^5$ is —$OR^6$. In another embodiment is a compound of Formula (I), or a pharmaceutically acceptable salt thereof, wherein $R^2$ is $C_{1-9}$heteroaryl substituted with one $R^5$, $R^5$ is —$OR^6$, and $R^6$ is selected from hydrogen and $C_{1-6}$alkyl optionally substituted with one, two, or three groups selected from halogen and hydroxy. In another embodiment is a compound of Formula (I), or a pharmaceutically acceptable salt thereof, wherein $R^2$ is $C_{1-9}$heteroaryl substituted with one $R^5$, $R^5$ is —$OR^6$, and $R^6$ is hydrogen. In another embodiment is a compound of Formula (I), or a pharmaceutically acceptable salt thereof, wherein $R^2$ is $C_{1-9}$heteroaryl substituted with one $R^5$, $R^5$ is —$OR^6$, and $R^6$ is $C_{1-6}$alkyl substituted with one, two, or three halogen. In another embodiment is a compound of Formula (I), or a pharmaceutically acceptable salt thereof, wherein $R^2$ is $C_{1-9}$heteroaryl substituted with one $R^5$, $R^5$ is —$OR^6$, and $R^6$ is $C_{1-6}$alkyl substituted with one hydroxy. In another embodiment is a compound of Formula (I), or a pharmaceutically acceptable salt thereof, wherein $R^2$ is $C_{1-9}$heteroaryl substituted with one $R^5$, $R^5$ is —$OR^6$, and $R^6$ is unsubstituted $C_{1-6}$alkyl. In another embodiment is a compound of Formula (I), or a pharmaceutically acceptable salt thereof, wherein $R^2$ is $C_{1-9}$heteroaryl substituted with one $R^5$ and $R^5$ is $C_{1-6}$alkyl optionally substituted with one group selected from —$OR^{10}$, —$C(O)OR^{10}$, —$C(O)N(R^{10})(R^{11})$, and —$S(O)_2R^{13}$. In another embodiment is a compound of Formula (I), or a pharmaceutically acceptable salt thereof, wherein $R^2$ is $C_{1-9}$heteroaryl substituted with one $R^5$, $R^5$ is $C_{1-6}$alkyl optionally substituted with one group selected from —$OR^{10}$, —$C(O)OR^{10}$, and —$C(O)N(R^{10})(R^{11})$, and $R^{10}$ is selected from hydrogen, $C_{1-6}$alkyl, and $C_{1-6}$haloalkyl. In another embodiment is a compound of Formula (I), or a pharmaceutically acceptable salt thereof, wherein $R^2$ is $C_{1-9}$heteroaryl substituted with one $R^5$, R is $C_{1-6}$alkyl substituted with —$OR^{10}$, and $R^{10}$ is hydrogen. In another embodiment is a compound of Formula (I), or a pharmaceutically acceptable salt thereof, wherein $R^2$ is $C_{1-9}$heteroaryl substituted with one $R^5$, R is $C_{1-6}$alkyl substituted with —$OR^{10}$, and $R^{10}$ is $C_{1-6}$alkyl. In another embodiment is a compound of Formula (I), or a pharmaceutically acceptable salt thereof, wherein $R^2$ is $C_{1-9}$heteroaryl substituted with one $R^5$, R is $C_{1-6}$alkyl substituted with —$C(O)OR^{10}$, and $R^{10}$ is hydrogen. In another embodiment is a compound of Formula (I), or a pharmaceutically acceptable salt thereof, wherein $R^2$ is $C_{1-9}$heteroaryl substituted with one $R^5$, $R^5$ is $C_{1-6}$alkyl substituted with —$C(O)OR^{10}$, and $R^{10}$ is $C_{1-6}$alkyl. In another embodiment is a compound of Formula (I), or a pharmaceutically acceptable salt thereof, wherein $R^2$ is unsubstituted $C_{1-9}$heteroaryl.

In another embodiment is a compound of Formula (I), or a pharmaceutically acceptable salt thereof, wherein each $R^{10}$ is independently selected hydrogen, $C_{1-6}$alkyl, and $C_{1-6}$haloalkyl.

In another embodiment is a compound of Formula (I), or a pharmaceutically acceptable salt thereof, wherein $R^3$ is hydrogen. In another embodiment is a compound of Formula (I), or a pharmaceutically acceptable salt thereof, wherein $R^3$ is $C_1$-$C_6$alkyl. In another embodiment is a compound of Formula (I), or a pharmaceutically acceptable salt thereof, wherein $R^3$ is $C_1$-$C_6$haloalkyl. In another embodiment is a compound of Formula (I), or a pharmaceutically acceptable salt thereof, wherein $R^3$ is $C_{3-8}$cycloalkyl.

In another embodiment is a compound of Formula (I), or a pharmaceutically acceptable salt thereof, wherein X is a bond. In another embodiment is a compound of Formula (I), or a pharmaceutically acceptable salt thereof, wherein X is $C_1$-$C_6$alkylene. In another embodiment is a compound of Formula (I), or a pharmaceutically acceptable salt thereof, wherein X is —$C(CH_3)_2$—. In another embodiment is a compound of Formula (I), or a pharmaceutically acceptable salt thereof, wherein X is —$C(H)(CH_3)$—. In another embodiment is a compound of Formula (I), or a pharmaceutically acceptable salt thereof, wherein X is —$CH_2$—.

Further embodiments provided herein include combinations of one or more of the particular embodiments set forth above.

In some embodiments is a compound selected from:

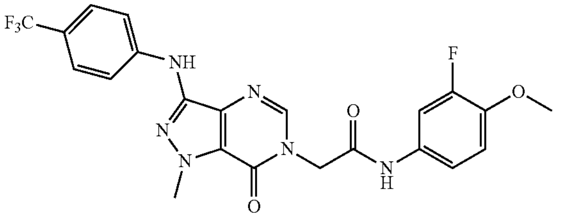
,

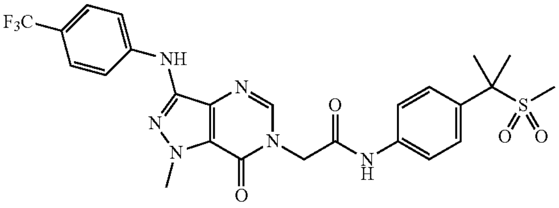
,

-continued

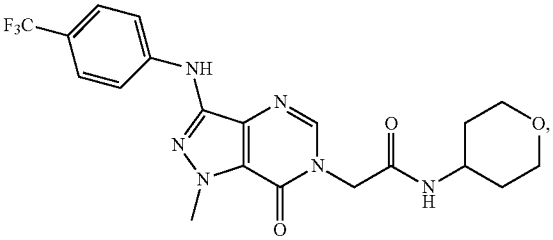
,

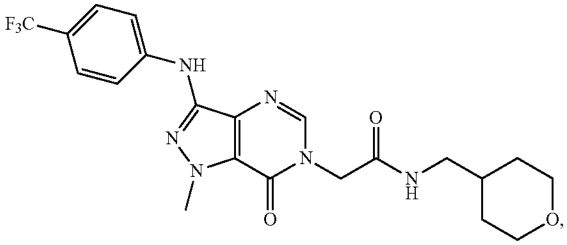
,

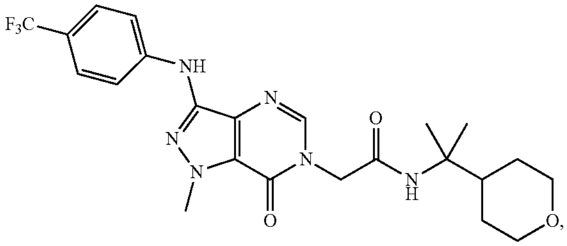
,

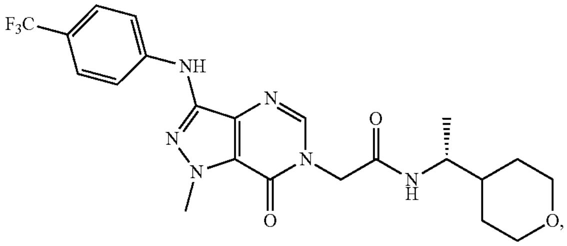
,

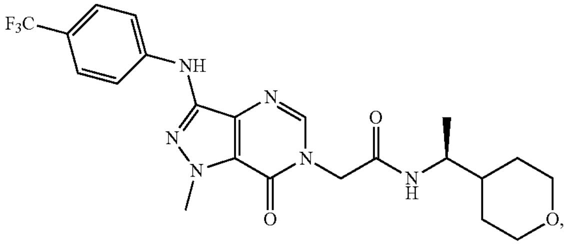
,

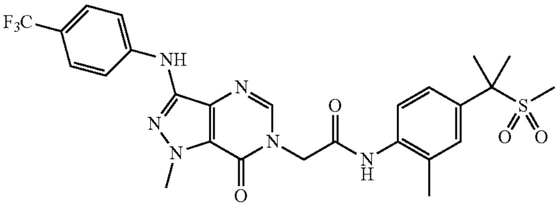
,

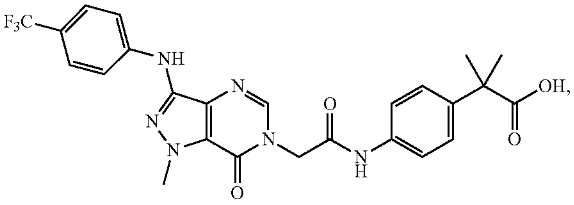
,

-continued
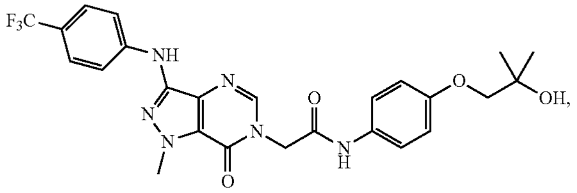
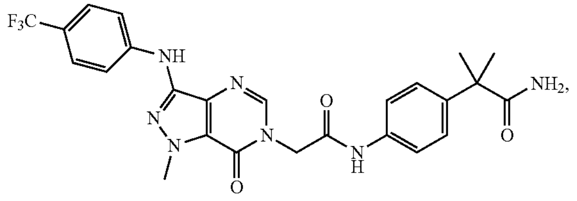
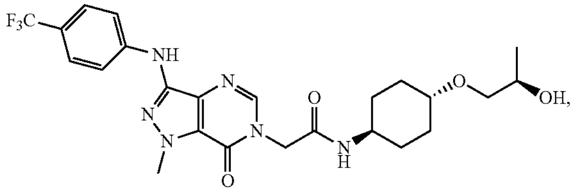
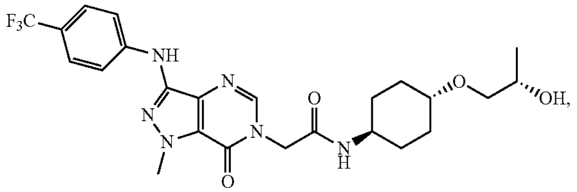
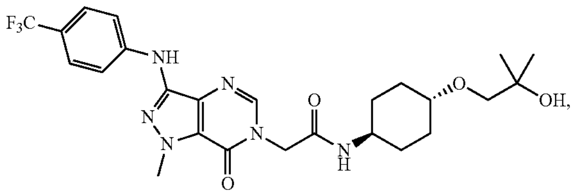
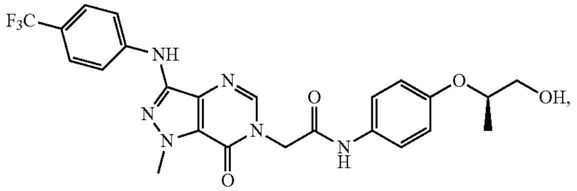
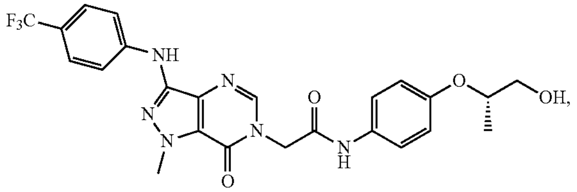
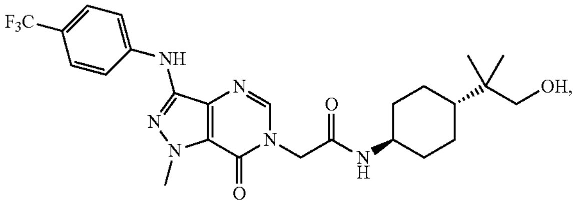
-continued
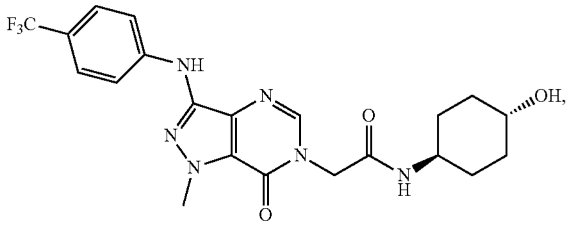
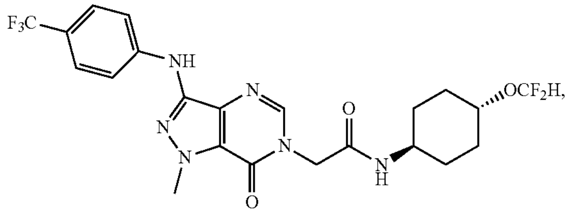
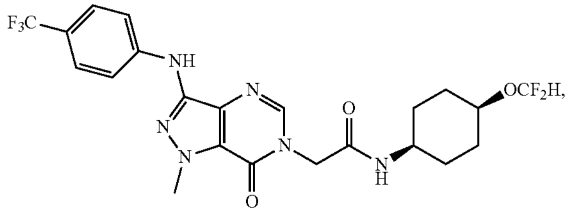
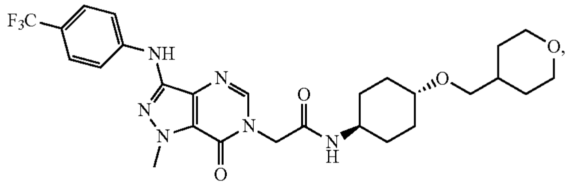
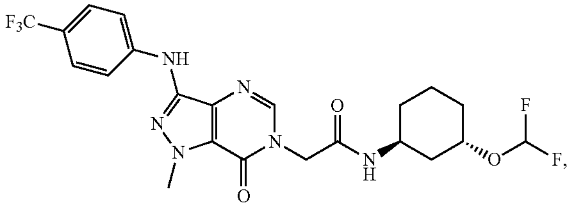
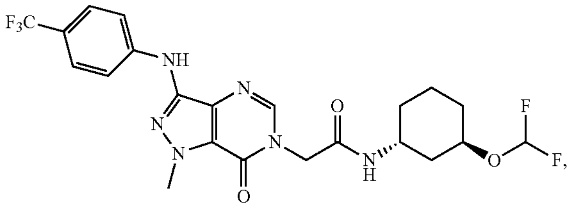
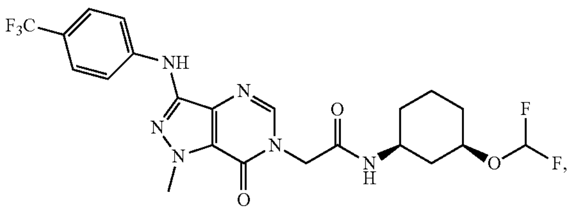
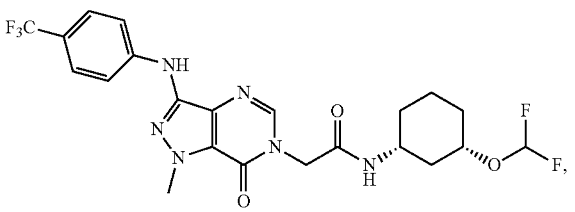

-continued

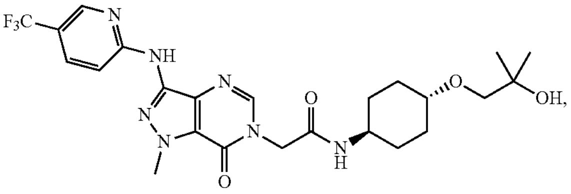

,

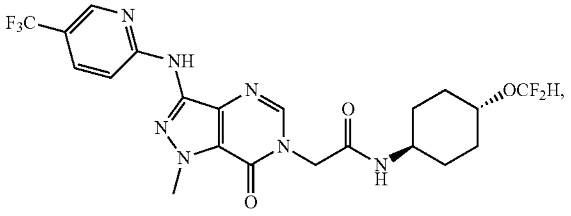

,

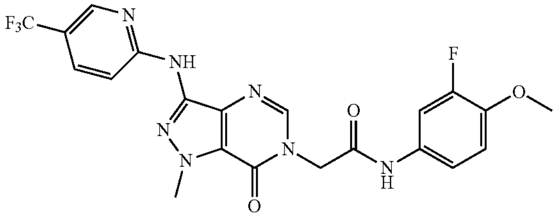

,

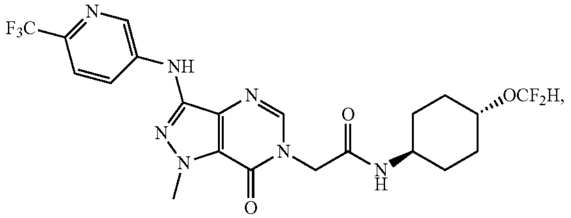

,

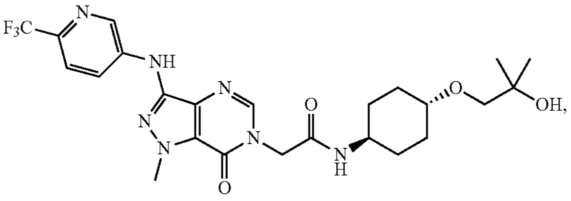

,

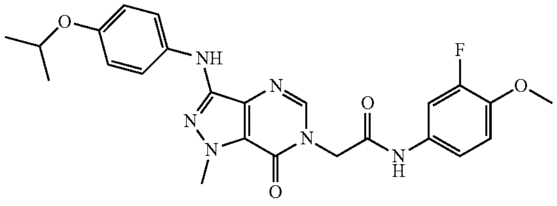

,

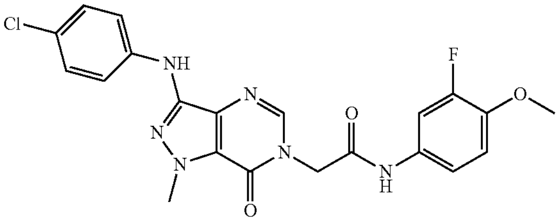

,

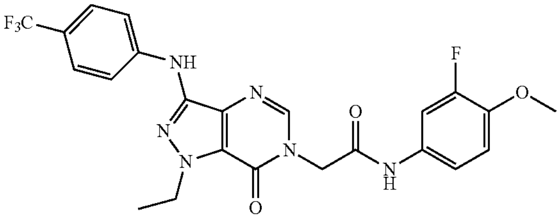

,

-continued

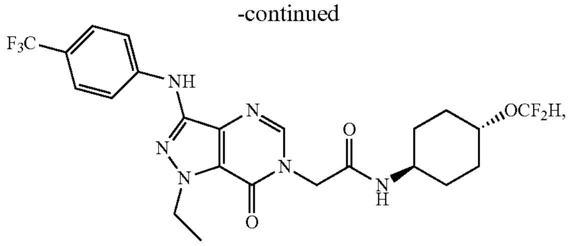

,

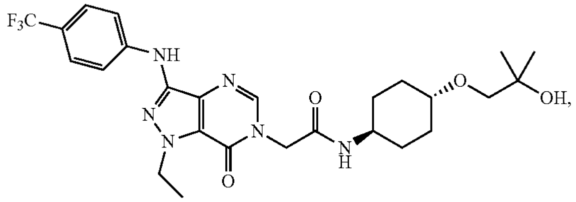

,

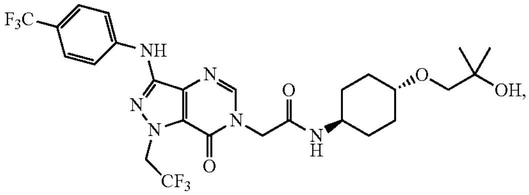

and

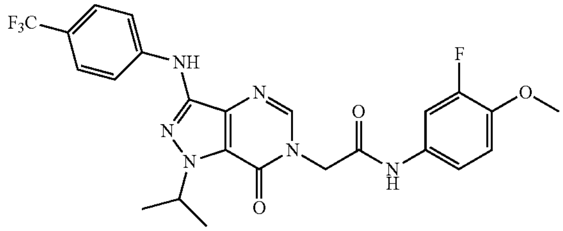

;

or a pharmaceutically acceptable salt thereof.

Preparation of Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, WI, including Sigma Chemical and Fluka), Apin Chemicals Ltd. (Milton Park, UK), Ark Pharm, Inc. (Libertyville, IL), Avocado Research (Lancashire, U.K.), BDH Inc. (Toronto, Canada), Bionet (Cornwall, U.K.), Chemservice Inc. (West Chester, PA), Combi-blocks (San Diego, CA), Crescent Chemical Co. (Hauppauge, NY), eMolecules (San Diego, CA), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Matrix Scientific, (Columbia, SC), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Ryan Scientific, Inc. (Mount Pleasant, SC), Spectrum Chemicals (Gardena, CA), Sundia Meditech, (Shanghai, China), TCI America (Portland, OR), Trans World Chemicals, Inc. (Rockville, MD), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}p$, $^{35}S$, $^{18}F$, and $^{36}Cl$, respectively. Compounds described herein, and pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the compound of Formula (I) as described herein is administered as a pure chemical. In some embodiments, the compound of Formula (I) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, PA (2005)).

Accordingly, provided herein is a pharmaceutical composition comprising at least one compound of Formula (I) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof.

In certain embodiments, the compound of Formula (I) as described herein is substantially pure, in that it contains less than about 5%, or less than about 1%, or less than about 0.1%, of other organic small molecules, such as contaminating intermediates or by-products that are created, for example, in one or more of the steps of a synthesis method.

In certain embodiments, the compound of Formula (I) described herein is formulated for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (optionally, cottonseed, groundnut, corn, germ, olive, castor and sesame oils), glycerol, tetrahydrofuryl alcohol, polyethylene glycols and fatty acid esters of sorbitan, cyclodextrins, and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Methods

In some embodiments is a method of treating cancer in a patient in need thereof, comprising administering to the patient a therapeutically effective amount of a compound of Formula (I) described herein, or a pharmaceutically acceptable salt thereof. In some embodiments is a method of treating cancer in a patient in need thereof, comprising administering to the patient a therapeutically effective amount of a compound of Formula (I) described herein, or a pharmaceutically acceptable salt thereof, wherein the cancer is selected from adrenocortical carcinoma, ovarian cancer, head and neck cancer, endometrial cancer, hormone-dependent prostate cancer, non-small cell lung carcinoma (NSCLC), melanoma, pituitary gonadotroph adenomas, and sex cord stromal tumors. In some embodiments is a method of treating adrenocortical carcinoma in a patient in need thereof, comprising administering to the patient a therapeutically effective amount of a compound of Formula (I) described herein, or a pharmaceutically acceptable salt thereof. In some embodiments is a method of treating ovarian cancer in a patient in need thereof, comprising administering to the patient a therapeutically effective amount of a compound of Formula (I) described herein, or a pharmaceutically acceptable salt thereof. In some embodiments is a method of treating head and neck cancer in a patient in need thereof, comprising administering to the patient a therapeutically effective amount of a compound of Formula (I) described herein, or a pharmaceutically acceptable salt thereof. In some embodiments is a method of treating endometrial cancer in a patient in need thereof, comprising administering to the patient a therapeutically effective amount of a compound of Formula (I) described herein, or a pharmaceutically acceptable salt thereof. In some embodiments is a method of treating hormone-dependent prostate cancer in a patient in need thereof, comprising administering to the patient a therapeutically effective amount of a compound of Formula (I) described herein, or a pharmaceutically acceptable salt thereof. In some embodiments is a method of treating non-small cell lung carcinoma (NSCLC) in a patient in need thereof, comprising administering to the patient a therapeutically effective amount of a compound of Formula (I) described herein, or a pharmaceutically acceptable salt thereof. In some embodiments is a method of treating melanoma in a patient in need thereof, comprising administering to the patient a therapeutically effective amount of a compound of Formula (I) described herein, or a pharmaceutically acceptable salt thereof. In some embodiments is a method of treating pituitary gonadotroph adenomas in a patient in need thereof, comprising administering to the patient a therapeutically effective amount of a compound of Formula (I) described herein, or a pharmaceutically acceptable salt thereof. In some embodiments is a method of treating sex cord stromal tumors in a patient in need thereof, comprising administering to the patient a therapeutically effective amount of a compound of Formula (I) described herein, or a pharmaceutically acceptable salt thereof. In some embodiments the sex cord stromal tumor is a Leydig cell tumor.

In some embodiments is a method of treating an endocrine disease in a mammal in need thereof, comprising administering to the mammal a therapeutically effective amount of a compound of Formula (I) described herein, or a pharmaceutically acceptable salt thereof. In another embodiment is a method of treating an endocrine disease in a mammal in need thereof, comprising administering to the mammal a therapeutically effective amount of a compound of Formula (I) described herein, or a pharmaceutically acceptable salt thereof, wherein the endocrine disease is selected from endogenous Cushing's syndrome, congenital adrenal hyperplasia, and polycystic ovary syndrome. In some embodiments is a method of treating endogenous Cushing's syndrome in a patient in need thereof, comprising administering to the patient a therapeutically effective amount of a compound of Formula (I) described herein, or a pharmaceutically acceptable salt thereof. In some embodiments is a method of treating congenital adrenal hyperplasia in a patient in need thereof, comprising administering to the patient a therapeutically effective amount of a compound of Formula (I) described herein, or a pharmaceutically acceptable salt thereof. In some embodiments is a method of treating polycystic ovary syndrome in a patient in need thereof, comprising administering to the patient a therapeutically effective amount of a compound of Formula (I) described herein, or a pharmaceutically acceptable salt thereof.

In some embodiments is a method of treating endometriomas or endometriosis in a patient in need thereof, comprising administering to the patient a therapeutically effective amount of a compound of Formula (I) described herein, or a pharmaceutically acceptable salt thereof.

In certain embodiments, a disclosed compound utilized by one or more of the foregoing methods is one of the generic, subgeneric, or specific compounds described herein, such as a compound of Formula (I).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration include subcutaneous injections, intravenous, or intramuscular injections or infusion techniques.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
DCC dichloroethane ($ClCH_2CH_2Cl$)
DCM N,N'-dicyclohexylcarbodiimide
DIPEA N,N-diisopropylethylamine
DMAP 4-(N,N-dimethylamino)pyridine
DMF dimethylformamide
DMA N,N-dimethylacetamide
DMSO dimethylsulfoxide
equiv equivalent(s)
EDCI 1-(3-dimethylaminopropyl)-3-ethylcarbodiimide
Et ethyl
EtOH ethanol
EtOAc ethyl acetate
HF hydrofluoric acid
HMDS bis(trimethylsilyl)amine
HPLC high performance liquid chromatography
Me methyl
MeOH methanol
MMTr 4-methoxytrityl
MMTrCl 4-methoxytrityl chloride
MS mass spectroscopy
NMM N-methylmorpholine
NMR nuclear magnetic resonance
TBHP tert-butyl hydroperoxide
TEA triethylamine
TFA trifluoroacetic acid
THF tetrahydrofuran
TLC thin layer chromatography
TBDMSCl tert-butyldimethylsilyl chloride
TMSCl trimethylsilyl chloride
TMSOTf trimethylsilyl trifluoromethanesulfonate

Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: Synthesis of 2-(1-methyl-7-oxo-3-((4-(trifluoromethyl)phenyl)amino)-1,7-dihydro-6H-pyrazolo[4,3-d]pyrimidin-6-yl)acetic acid (10)

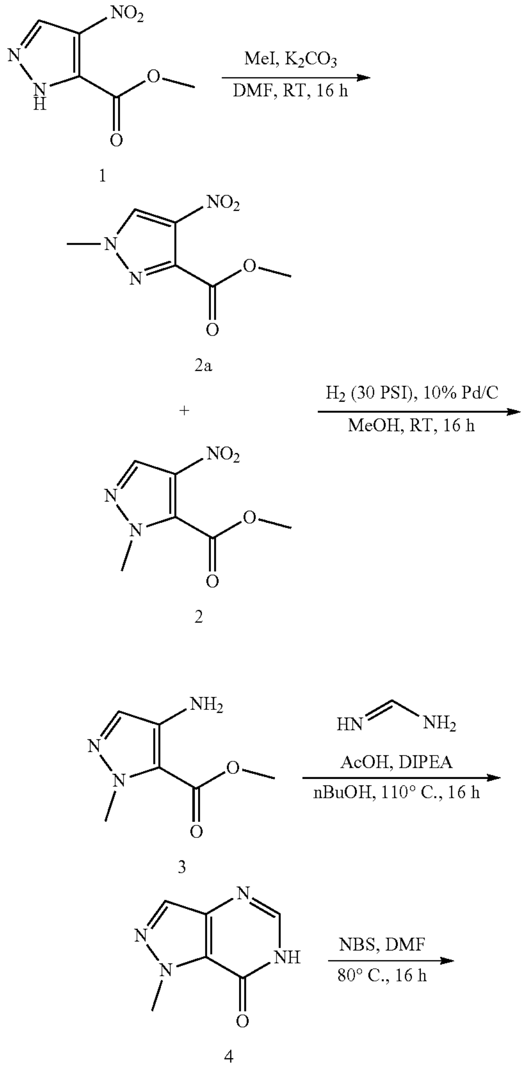

1

2a

+

2

3

4

-continued

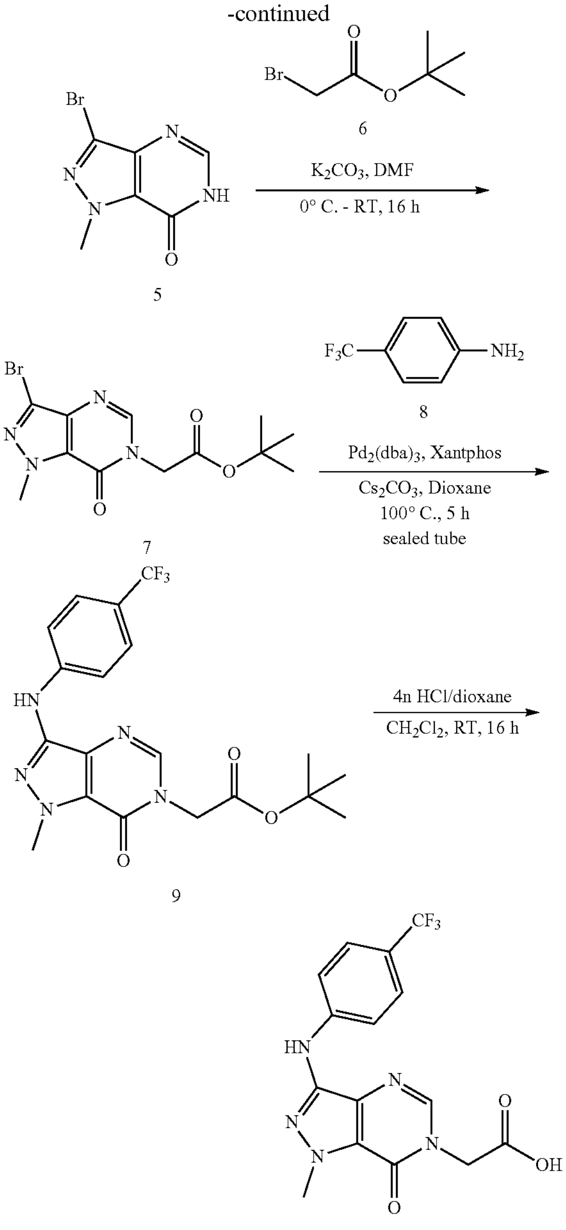

5 6 7 8 9 10

To a stirred solution of methyl 4-nitro-1H-pyrazole-5-carboxylate (1) (50 g, 292.2 mmol) in DMF (500 mL) were added $K_2CO_3$ (80.6 g, 584.4 mmol) followed by methyl iodide (20.0 mL, 321.4 mmol) at RT and reaction mixture was stirred for 16 h at same temperature. The mixture was quenched with water and extracted with EtOAc. Organic layer was dried over anhydrous $Na_2SO_4$, filtered and concentrated to obtain the crude. The crude was purified through silica gel column to afford methyl 1-methyl-4-nitro-1H-pyrazole-5-carboxylate (2) (15.0 g, 27%) as a colorless liquid. $^1$H NMR (400 MHz, $CDCl_3$): δ 8.01 (s, 1H), 4.03 (s, 6H); MS (ESI) m/z 186.17 $[M+H]^+$.

To a stirred solution of methyl 4-nitro-1H-pyrazole-5-carboxylate (2) (2×7.5 g, 40.54 mmol) in MeOH (75 mL) was added 10% Pd/C (3 g) and the reaction mixture was stirred at RT under hydrogen (balloon pressure) atmosphere for 16 h. Reaction mixture was filtered through celite pad and the filtrate was concentrated to obtain methyl 4-amino-1H-pyrazole-5-carboxylate (3) (12.2 g, 97%). $^1$H NMR (400 MHz, DMSO): δ 7.00 (s, 1H), 4.98 (brs, 2H), 3.89 (s, 3H), 3.79 (s, 3H); MS (ESI) m/z 156.07 $[M+H]^+$.

To a stirred solution of methyl 4-amino-1H-pyrazole-5-carboxylate (3) (12.2 g, 78.70 mmol) in n-butanol (122 mL) were added DIPEA (72.5 mL, 393.50 mmol), formamidine acetate (4) (9.80 g, 94.45 mmol) at RT and then the reaction was stirred at 110° C. for 16 h. The reaction mixture was cooled to RT and precipitated solid was filtered off. The solid compound was triturated with diethyl ether to afford 1-methyl-1,6-dihydro-7H-pyrazolo[4,3-d]pyrimidin-7-one (5) (10.0 g, 84%) as an off-white solid. $^1$H NMR (400 MHz, DMSO-$d_6$): δ 7.95 (s, 1H), δ 7.80 (s, 1H), δ 4.18 (s, 3H); MS (ESI) m/z 151.09 $[M+H]^+$.

To a stirred solution of 1-methyl-1,6-dihydro-7H-pyrazolo[4,3-d]pyrimidin-7-one (4) (10.0 g, 66.66 mmol) in DMF (200 mL) was added NBS (15.41 g, 86.58 mmol) at RT and the reaction mixture was stirred at 80° C. for 16 h. The reaction mixture was cooled to RT, quenched with cold water and the precipitated solid was filtered off. The solid was dried under vacuum to afford 3-bromo-1-methyl-1,6-dihydro-7H-pyrazolo[4,3-d]pyrimidin-7-one (5) (11.0 g, 72%) as an off-white solid. $^1$H NMR (400 MHz, DMSO-$d_6$): δ 12.49 (brs, 1H), 7.92 (s, 1H), δ 4.18 (s, 3H); MS (ESI) m/z 229.06 $[M+H]^+$.

To a stirred solution of 3-bromo-1-methyl-1,6-dihydro-7H-pyrazolo[4,3-d]pyrimidin-7-one (5) (11.0 g, 48.24 mmol) in DMF (220 mL) were added $K_2CO_3$ (13.25 g, 96.06 mmol) and tert-butyl 2-bromoacetate (6) (8.24 mL, 57.64 mmol) at 0° C. and stirred at RT for 16 h. The reaction mixture was quenched with water (100 mL) and extracted with EtOAc (2×1 L). The organic layer was dried over anhydrous $Na_2SO_4$, filtered and concentrated to obtain the crude that was purified by flash column chromatography to afford tert-butyl 2-(3-bromo-1-methyl-7-oxo-1,7-dihydro-6H-pyrazolo[4,3-d]pyrimidin-6-yl)acetate (7) (12.0 g, 72%) as a white solid. $^1$H NMR (400 MHz, $CDCl_3$): δ 7.79 (s, 1H), 4.61 (s, 2H), 4.28 (s, 3H), 1.49 (s, 9H); MS (ESI) m/z 343.22 $[M+H]^+$.

To a degassed (argon) solution of tert-butyl 2-(3-bromo-1-methyl-7-oxo-1,7-dihydro-6H-pyrazolo[4,3-d]pyrimidin-6-yl)acetate (7) (5.0 g, 14.619 mmol) in dioxane (100 mL) were added $Cs_2CO_3$ (14.24 g, 43.71 mmol), $Pd_2(dba)_3$ (1.32 g, 1.45 mmol), Xantphos (843 mg, 1.45 mmol) and 4-(trifluoromethyl)aniline (8) (2.35 g, 14.619 mmol) at RT in a pressure vessel. The solution was degassed again for 15 min and the reaction mixture was heated to 100° C. for 5 h. The reaction mixture was cooled to room temperature and filtered through a celite pad. The celite pad was washed with ethyl acetate. The filtrate was concentrated under reduced pressure to afford the crude, which was purified by silica gel column chromatography to obtain tert-butyl 2-(1-methyl-7-oxo-3-((4-(trifluoromethyl)phenyl)amino)-1,7-dihydro-6H-pyrazolo[4,3-d]pyrimidin-6-yl)acetate (9) (4.8 g, 77%) as a brown solid. $^1$H NMR (400 MHz, DMSO-$d_6$): δ 9.46 (s, 1H), 8.15 (s, 1H), 7.73 (d, J=8.4 Hz, 2H), 7.57 (d, J=8.4 Hz, 2H), 4.74 (s, 2H), 4.13 (s, 3H), 1.44 (s, 9H); MS (ESI) m/z 424.4 $[M+H]^+$.

To a stirred solution of tert-butyl 2-(1-methyl-7-oxo-3-((4-(trifluoromethyl)phenyl)amino)-1,7-dihydro-6H-pyrazolo[4,3-d]pyrimidin-6-yl)acetate (9) (4.8 g, 11.34 mmol) in DCM (25 mL) was added 4N HCl in dioxane (50 mL) at 0° C. and stirred at RT for 16 h. The solvent was evaporated under reduced pressure, triturated with ethyl acetate and dried under reduced pressure to afford 2-(1-methyl-7-oxo-3-((4-(trifluoromethyl)phenyl)amino)-1,7-dihydro-6H-pyrazolo[4,3-d]pyrimidin-6-yl)acetic acid (10) (4.8 g) as a pale yellow solid. $^{1}H$ NMR (400 MHz, DMSO-$d_6$): δ 9.45 (s, 1H), 8.17 (s, 1H), 7.72 (d, J=8.8 Hz, 2H), 7.57 (d, J=8.4 Hz, 2H), 4.77 (s, 2H), 4.13 (s, 3H), 3.56 (s, 1H); MS (ESI) m/z 368.30 $[M+H]^+$.

Example 2: Synthesis of N-(3-fluoro-4-methoxyphenyl)-2-(1-methyl-7-oxo-3-((4-(trifluoromethyl)phenyl)amino)-1,7-dihydro-6H-pyrazolo[4,3-d]pyrimidin-6-yl)acetamide (11)

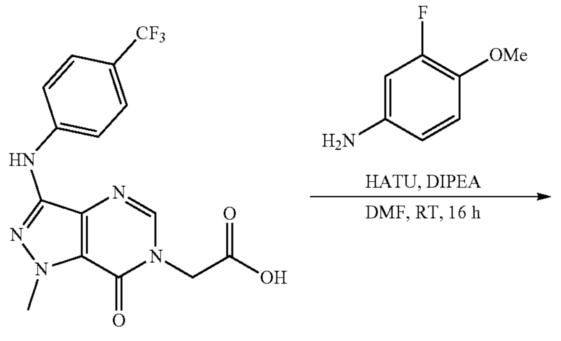

10

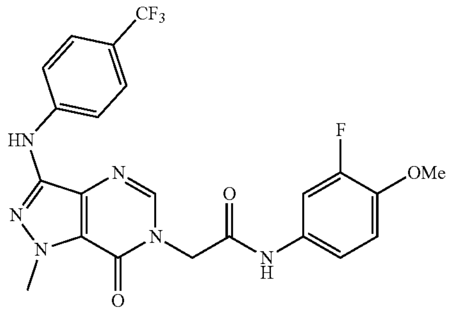

11

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (300 mg, 0.81 mmol) in DMF (3 mL) were added HATU (465 mg, 1.22 mmol), DIPEA (0.45 mL, 2.45 mmol) at 0° C. and reaction mixture was stirred for 5 min at same temperature. Then added 3-fluoro-4-methoxyaniline (126 mg, 0.89 mmol) and the reaction was stirred at RT for 16 h. The reaction mixture was quenched with ice cold water. The precipitated solid was washed with diethyl ether to afford N-(3-fluoro-4-methoxyphenyl)-2-(1-methyl-7-oxo-3-((4-(trifluoromethyl)phenyl)amino)-1,7-dihydro-6H-pyrazolo[4,3-d]pyrimidin-6-yl)acetamide (11) (106 mg, 26%) as an off-white solid. MS (ESI) m/z 491.56 $[M+H]^+$; $^{1}H$ NMR (400 MHz, DMSO-$d_6$): δ 10.48 (s, 1H), 9.46 (s, 1H), 8.15 (s, 1H), 7.73 (d, J=8.4 Hz, 2H), 7.60-7.50 (m, 3H), 7.27 (d, J=8.8 Hz, 1H), 7.14 (t, J=9.2 Hz, 1H), 4.86 (s, 2H), 4.13 (s, 3H), 3.80 (s, 3H), 1.44 (s, 6H).

Example 3: Synthesis of 2-(1-methyl-7-oxo-3-((4-(trifluoromethyl)phenyl)amino)-1,7-dihydro-6H-pyrazolo[4,3-d]pyrimidin-6-yl)-N-(4-(2-(methylsulfonyl)propan-2-yl)phenyl)acetamide (12)

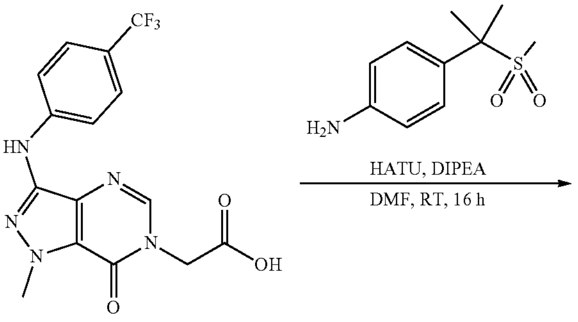

10

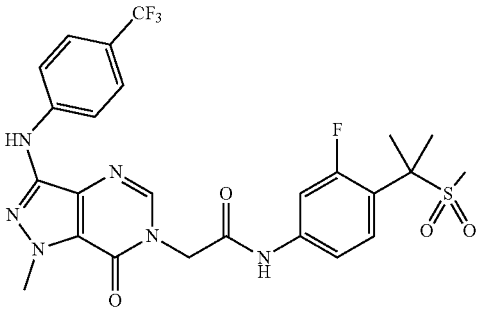

12

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (300 mg, 0.81 mmol) in DMF (3 mL) were added HATU (465 mg, 1.22 mmol), DIPEA (0.4 mL, 2.45 mmol) at 0° C. and reaction mixture was stirred for 5 min at same temperature. Then added 4-(2-(methylsulfonyl)propan-2-yl)aniline (2) (208 mg, 0.98 mmol) and the reaction was stirred at RT for 16 h. The reaction mixture was quenched with ice cold water. The precipitated solid was filtered and purified by prep HPLC to afford 2-(1-methyl-7-oxo-3-((4-(trifluoromethyl)phenyl)amino)-1,7-dihydro-6H-pyrazolo[4,3-d]pyrimidin-6-yl)-N-(4-(2-(methylsulfonyl)propan-2-yl)phenyl)acetamide (12) (110 mg, 23%) as an off-white solid. MS (ESI) m/z 563.43 $[M+H]^+$; $^{1}H$ NMR (400 MHz, DMSO-$d_6$): δ 10.58 (s, 1H), 9.47 (s, 1H), 8.17 (s, 1H), 7.74 (s, 1H), 7.72 (s, 1H), 7.65-7.53 (m, 6H), 4.89 (s, 2H), 4.13 (s, 3H), 2.65 (s, 3H), 1.73 (s, 6H).

Example 4: Synthesis of 2-(1-methyl-7-oxo-3-((4-(trifluoromethyl)phenyl)amino)-1,7-dihydro-6H-pyrazolo[4,3-d]pyrimidin-6-yl)-N-(tetrahydro-2H-pyran-4-yl)acetamide (13)

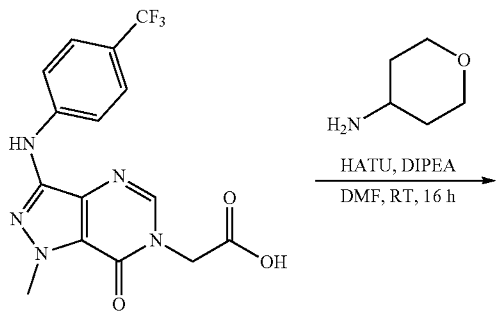

10

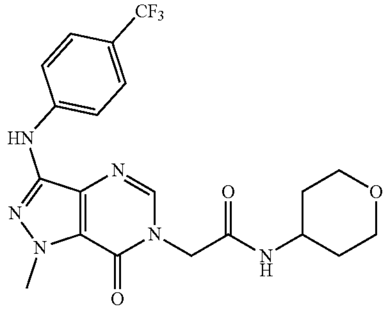

13

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (300 mg, 0.81 mmol) in DMF (3 mL) were added HATU (465 mg, 1.22 mmol), DIPEA (0.4 mL, 2.45 mmol) at 0° C. and reaction mixture was stirred for 5 min at same temperature. Then added tetrahydro-2H-pyran-4-amine (99 mg, 0.98 mmol) and the reaction was stirred at RT for 16 h. The reaction mixture was quenched with ice cold water. The precipitated solid was filtered and purified by prep HPLC to afford 2-(1-methyl-7-oxo-3-((4-(trifluoromethyl)phenyl)amino)-1,7-dihydro-6H-pyrazolo[4,3-d]pyrimidin-6-yl)-N-(tetrahydro-2H-pyran-4-yl)acetamide (13) (120 mg, 32%) as an off-white solid. MS (ESI) m/z 465.44 $[M+H]^+$; $^1H$ NMR (400 MHz, DMSO-$d_6$): δ 9.44 (s, 1H), 8.31 (s, 1H), 8.08 (s, 1H), 7.72 (d, J=8.4 Hz, 2H), 7.56 (d, J=8.4 Hz, 2H), 4.66 (s, 2H), 4.12 (s, 3H), 3.90-3.80 (m, 2H) 3.30-3.20 (m, 2H), 3.00 (t, J=6.0 Hz, 2H), 1.60-1.50 (m, 3H), 1.40-1.30 (m, 2H).

Example 5: Synthesis of 2-(1-methyl-7-oxo-3-((4-(trifluoromethyl)phenyl)amino)-1,7-dihydro-6H-pyrazolo[4,3-d]pyrimidin-6-yl)-N-((tetrahydro-2H-pyran-4-yl)methyl)acetamide (14)

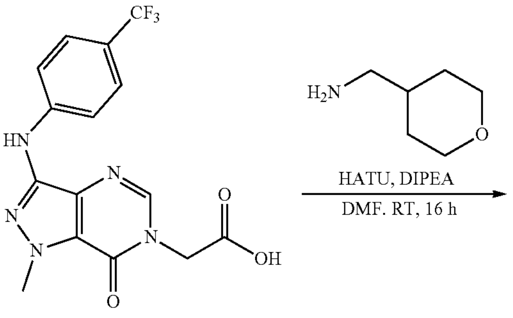

10

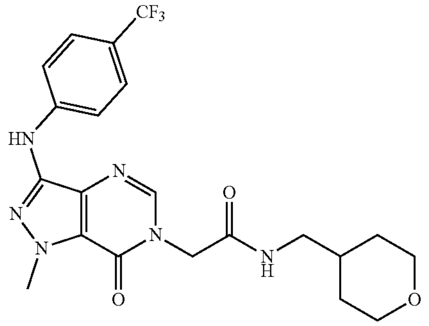

14

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (300 mg, 0.817 mmol) in DMF (5 mL) were added HATU (465 mg, 1.22 mmol), DIPEA (0.56 mL, 3.26 mmol) at 0° C. and reaction mixture was stirred for 5 min at same temperature. Then added (tetrahydro-2H-pyran-4-yl)methanamine (112 mg, 0.98 mmol) and the reaction was stirred at RT for 16 h. The reaction mixture was quenched with ice cold water. The precipitated solid was washed with diethyl ether to afford 2-(1-methyl-7-oxo-3-((4-(trifluoromethyl)phenyl)amino)-1,7-dihydro-6H-pyrazolo[4,3-d]pyrimidin-6-yl)-N-((tetrahydro-2H-pyran-4-yl)methyl)acetamide (14) (130 mg, 34%) as a pale yellow solid. MS (ESI) m/z 465.44 $[M+H]^+$; $^1H$ NMR (400 MHz, DMSO-$d_6$): δ 9.44 (s, 1H), 8.31 (s, 1H), 8.08 (s, 1H), 7.72 (d, J=8.4 Hz, 2H), 7.56 (d, J=8.4 Hz, 2H), 4.66 (s, 2H), 4.12 (s, 3H), 3.90-3.80 (m, 2H) 3.30-3.20 (m, 2H), 3.00 (t, J=6.0 Hz, 2H), 1.60-1.50 (m, 3H), 1.40-1.30 (m, 2H).

Example 6: Synthesis of 2-(1-methyl-7-oxo-3-((4-(trifluoromethyl)phenyl)amino)-1,7-dihydro-6H-pyrazolo[4,3-d]pyrimidin-6-yl)-N-(2-(tetrahydro-2H-pyran-4-yl)propan-2-yl)acetamide (15)

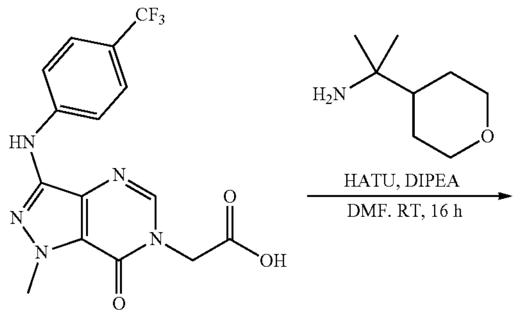

10

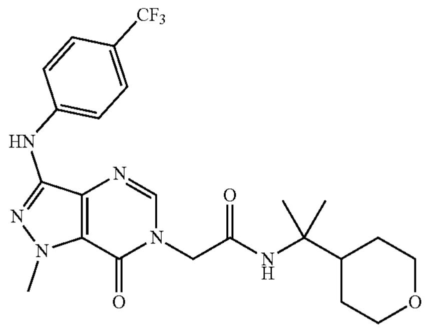

15

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (150 mg, 0.40 mmol) in DMF (3 mL) were added HATU (230 mg, 0.61 mmol), DIPEA (0.24 mL, 1.22 mmol) at 0° C. and reaction mixture was stirred for 5 min at same temperature. Then added 2-(tetrahydro-2H-pyran-4-yl)propan-2-amine (179 mg, 0.48 mmol) and the reaction was stirred at RT for 16 h. The reaction mixture was quenched with ice cold water. The precipitated solid was filtered and purified by prep HPLC to afford 2-(1-methyl-7-oxo-3-((4-(trifluoromethyl)phenyl)amino)-1,7-dihydro-6H-pyrazolo[4,3-d]pyrimidin-6-yl)-N-(2-(tetrahydro-2H-pyran-4-yl)propan-2-yl)acetamide (15) (60 mg, 29%) as an off-white solid. MS (ESI) m/z 493.56 $[M+H]^+$; $^1H$ NMR (400 MHz, DMSO-$d_6$): δ 9.43 (s, 1H), 8.05 (s, 1H), 7.83 (s, 1H), 7.71 (d, J=8.8 Hz, 2H), 7.56 (d, J=8.8 Hz, 2H), 4.63 (s, 2H), 4.12 (s, 3H), 4.00-3.90 (m, 2H), 3.30-3.15 (m, 2H), 2.20-2.05 (m, 1H), 1.60-1.50 (m, 2H), 1.40-1.10 (m, 8H).

Example 7: Synthesis of (R)-2-(1-methyl-7-oxo-3-((4-(trifluoromethyl)phenyl)amino)-1,7-dihydro-6H-pyrazolo[4,3-d]pyrimidin-6-yl)-N-(1-(tetrahydro-2H-pyran-4-yl)ethyl)acetamide (16)

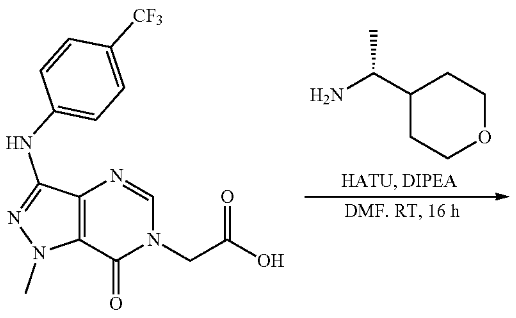

10

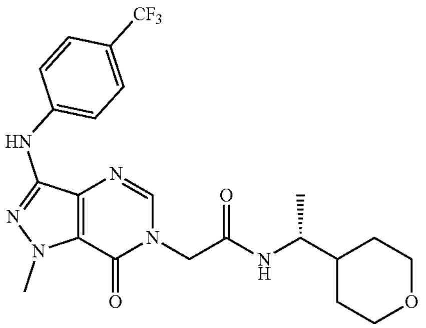

16

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (259 mg, 0.70 mmol) in DMF (5 mL) was added HATU (307 mg, 0.81 mmol), DIPEA (209 mg, 1.62 mmol) at 0° C. and reaction mixture was stirred for 5 min at same temperature. Added (R)-1-(tetrahydro-2H-pyran-4-yl)ethan-1-amine (70 mg, 0.54 mmol) and the reaction was stirred at RT for 16 h. The reaction mixture was diluted with cold water and extracted with EtOAc. Organic layer was evaporated the crude was purified by prep HPLC gave (R)-2-(1-methyl-7-oxo-3-((4-(trifluoromethyl)phenyl)amino)-1,7-dihydro-6H-pyrazolo[4,3-d]pyrimidin-6-yl)-N-(1-(tetrahydro-2H-pyran-4-yl)ethyl)acetamide (16) (45 mg, 17%) as a white solid. MS (ESI) m/z 479.63 $[M+H]^+$; $^1H$ NMR (400 MHz, DMSO-$d_6$): δ 9.43 (s, 1H), 8.12 (d, J=8.8 Hz, 1H), 8.08 (s, 1H), 7.72 (d, J=8.8 Hz, 2H), 7.56 (d, J=8.8 Hz, 2H), 4.65 (s, 2H), 4.12 (s, 3H), 3.90-3.80 (m, 2H), 3.70-3.60 (m, 1H), 3.40-3.20 (m, 2H), 1.65-1.45 (m, 3H), 1.30-1.15 (m, 2H), 1.04 (d, J=6.80 Hz, 3H).

Example 8: Synthesis of (S)-2-(1-methyl-7-oxo-3-((4-(trifluoromethyl)phenyl)amino)-1,7-dihydro-6H-pyrazolo[4,3-d]pyrimidin-6-yl)-N-(1-(tetrahydro-2H-pyran-4-yl)ethyl)acetamide (17)

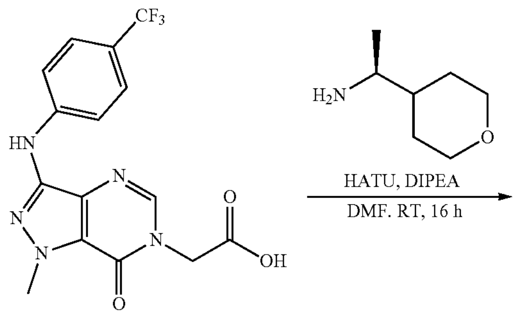

10

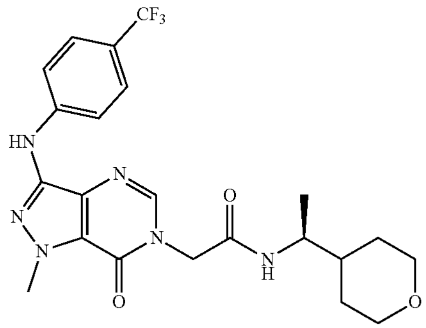

17

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (259 mg, 0.70 mmol) in DMF (5 mL) was added HATU (307 mg, 0.81 mmol), DIPEA (209 mg, 1.62 mmol) at 0° C. and reaction mixture was stirred for 5 min at same temperature. Added (S)-1-(tetrahydro-2H-pyran-4-yl)ethan-1-amine (70 mg, 0.54 mmol) and the reaction was stirred at RT for 16 h. The reaction mixture was diluted with cold water and extracted with EtOAc. The organic layer was evaporated and the residue was purified by prep HPLC to give (S)-2-(1-methyl-7-oxo-3-((4-(trifluoromethyl)phenyl)amino)-1,7-dihydro-6H-pyrazolo[4,3-d]pyrimidin-6-yl)-N-(1-(tetrahydro-2H-pyran-4-yl)ethyl)acetamide (17) (110 mg, 42%) as a white solid. MS (ESI) m/z 479.63 $[M+H]^+$; $^1H$ NMR (400 MHz, DMSO-$d_6$): δ 9.43 (s, 1H), 8.12 (d, J=8.8 Hz, 1H), 8.08 (s, 1H), 7.72 (d, J=8.8 Hz, 2H), 7.56 (d, J=8.8 Hz, 2H), 4.65 (s, 2H), 4.12 (s, 3H), 3.90-3.80 (m, 2H), 3.70-3.60 (m, 1H), 3.40-3.20 (m, 2H), 1.65-1.45 (m, 3H), 1.30-1.15 (m, 2H), 1.04 (d, J=6.80 Hz, 3H).

Example 9: Synthesis of N-(2-methyl-4-(2-(methylsulfonyl)propan-2-yl)phenyl)-2-(1-methyl-7-oxo-3-((4-(trifluoromethyl)phenyl)amino)-1,7-dihydro-6H-pyrazolo[4,3-d]pyrimidin-6-yl)acetamide (18)

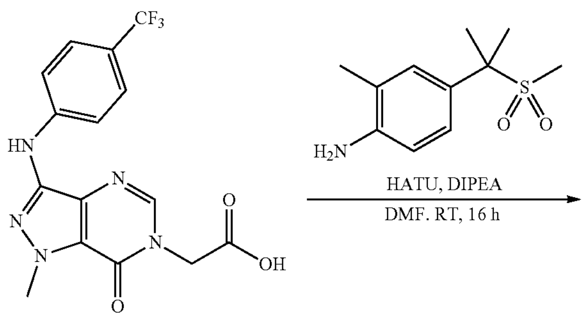

10

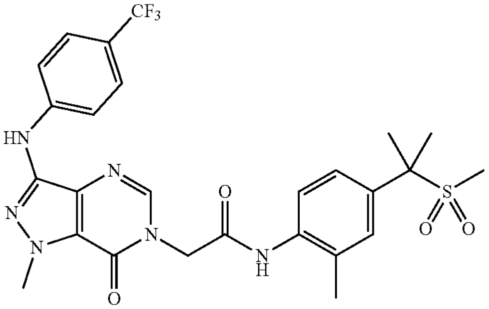

18

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (500 mg, 1.36 mmol) in DMF (3 mL) were added HATU (776 mg, 2.04 mmol), DIPEA (0.75 mL, 4.08 mmol) at 0° C. and reaction mixture was stirred for 5 min at same temperature. Then added 2-methyl-4-(2-(methylsulfonyl)propan-2-yl)aniline (371 mg, 1.63 mmol) and the reaction was stirred at RT for 16 h. The reaction mixture was quenched with ice cold water. The precipitated solid was filtered and purified by prep HPLC to afford N-(2-methyl-4-(2-(methylsulfonyl)propan-2-yl)phenyl)-2-(1-methyl-7-oxo-3-((4-(trifluoromethyl)phenyl)amino)-1,7-dihydro-6H-pyrazolo[4,3-d]pyrimidin-6-yl)acetamide (18) (97 mg, 12%) as an off-white solid. MS (ESI) m/z 577.47 $[M+H]^+$; $^1H$ NMR (400 MHz, DMSO-$d_6$): δ 9.82 (s, 1H), 9.45 (s, 1H), 8.17 (s, 1H), 7.72 (d, J=8.8 Hz, 2H), 7.56 (d, J=8.4 Hz, 2H), 7.55-7.35 (m, 3H), 4.95 (s, 2H), 4.14 (s, 3H), 2.68 (s, 3H), 2.29 (s, 3H), 1.73 (s, 6H).

Example 10: Synthesis of 2-methyl-2-(4-(2-(1-methyl-7-oxo-3-((4-(trifluoromethyl)phenyl)amino)-1,7-dihydro-6H-pyrazolo[4,3-d]pyrimidin-6-yl)acetamido)phenyl)propanoic acid (19)

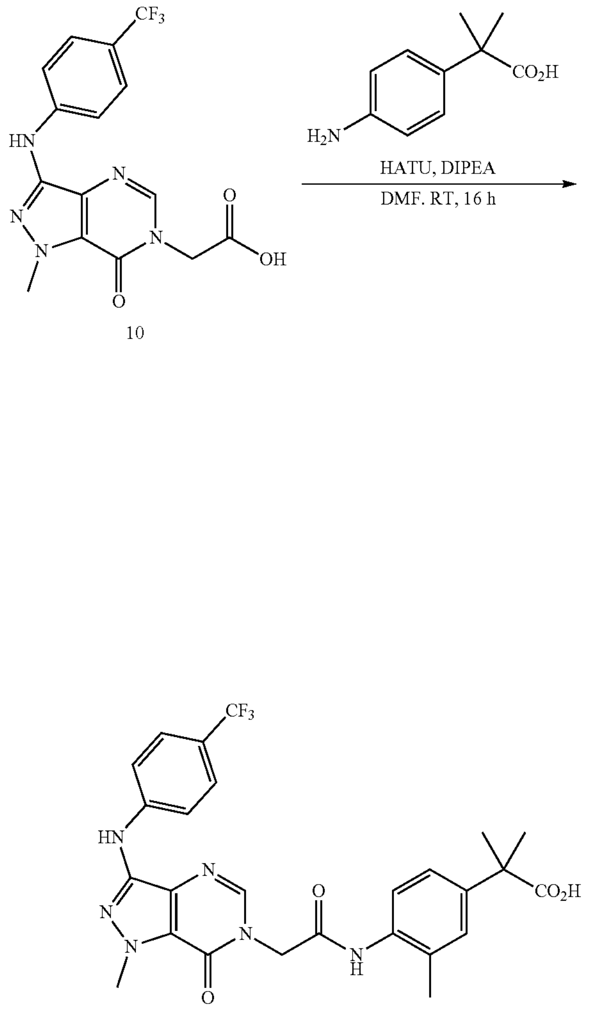

10

19

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (300 mg, 0.81 mmol) in DMF (3 mL) were added HATU (465 mg, 1.22 mmol), DIPEA (0.45 mL, 2.45 mmol) at 0° C. and reaction mixture was stirred for 5 min at same temperature. Then added 2-(4-aminophenyl)-2-methylpropanoic acid (175 mg, 0.98 mmol) and the reaction was stirred at RT for 16 h. The reaction mixture was quenched with ice cold water. The precipitated solid was filtered and purified by prep HPLC to afford 2-methyl-2-(4-(2-(1-methyl-7-oxo-3-((4-(trifluoromethyl)phenyl)amino)-1,7-dihydro-6H-pyrazolo[4,3-d]pyrimidin-6-yl)acetamido)phenyl)propanoic acid (19) (90 mg, 20%) as an off-white solid. MS (ESI) m/z 529.46 $[M+H]^+$; $^1H$ NMR (400 MHz, DMSO-$d_6$): δ 12.40-12.30 (br s, 1H), 10.45 (s, 1H), 9.46 (s, 1H), 8.16 (s, 1H), 7.73 (d, J=8.4 Hz, 2H), 7.60-7.50 (m, 4H), 7.31 (d, J=8.4 Hz, 1H), 4.88 (s, 2H), 4.13 (s, 3H), 1.44 (s, 6H).

Example 11: Synthesis of N-(4-(2-hydroxy-2-methylpropoxy)phenyl)-2-(1-methyl-7-oxo-3-((4-(trifluoromethyl)phenyl)amino)-1,7-dihydro-6H-pyrazolo[4,3-d]pyrimidin-6-yl)acetamide (20)

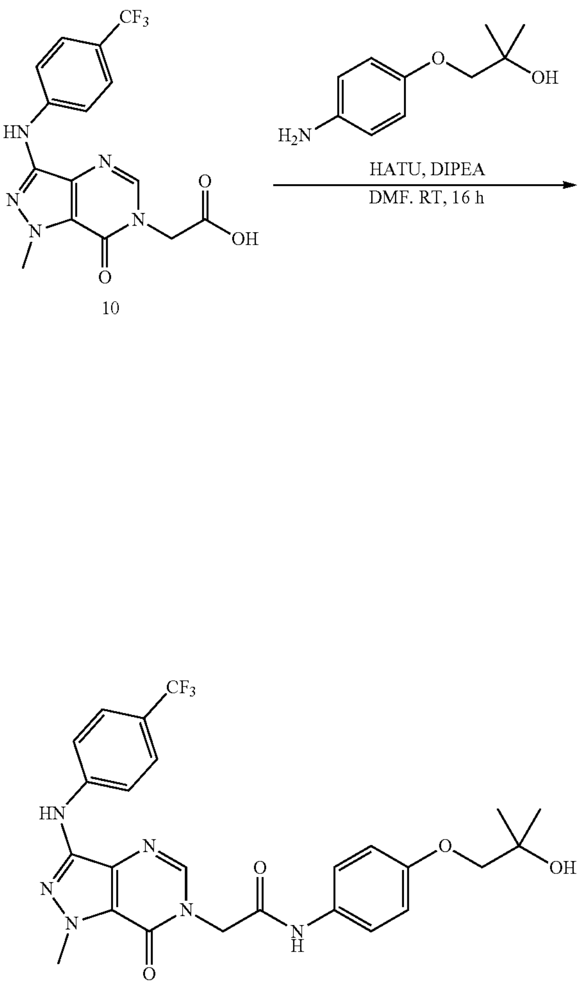

10

20

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (300 mg, 0.81 mmol) in DMF (3 mL) were added HATU (465 mg, 1.22 mmol), DIPEA (0.45 mL, 2.45 mmol) at 0° C. and reaction mixture was stirred for 5 min at same temperature. Then added 1-(4-aminophenoxy)-2-methylpropan-2-ol (177 mg, 0.98 mmol) and the reaction was stirred at RT for 16 h. The reaction mixture was quenched with ice cold water. The precipitated solid was washed with diethyl ether to afford to afford N-(4-(2-hydroxy-2-methylpropoxy)phenyl)-2-(1-methyl-7-oxo-3-((4-(trifluoromethyl)phenyl)amino)-1,7-dihydro-6H-pyrazolo[4,3-d]pyrimidin-6-yl)acetamide (20) (160 mg, 36%) as a gray colored solid. MS (ESI) m/z 531.65 $[M+H]^+$; $^1H$ NMR (400 MHz, DMSO-$d_6$): δ 10.29 (s, 1H), 9.46 (s, 1H), 8.15 (s, 1H), 7.73 (d, J=8.4 Hz, 2H), 7.57 (d, J=8.8 Hz, 2H), 7.48 (d, J=8.8 Hz, 2H), 6.90 (d, J=9.20 Hz, 2H), 4.87 (s, 2H), 4.59 (s, 1H), 4.13 (s, 3H), 3.69 (s, 2H), 1.18 (s, 6H).

Example 12: Synthesis of 2-methyl-2-(4-(2-(1-methyl-7-oxo-3-((4-(trifluoromethyl)phenyl)amino)-1,7-dihydro-6H-pyrazolo[4,3-d]pyrimidin-6-yl)acetamido)phenyl)propanamide (21)

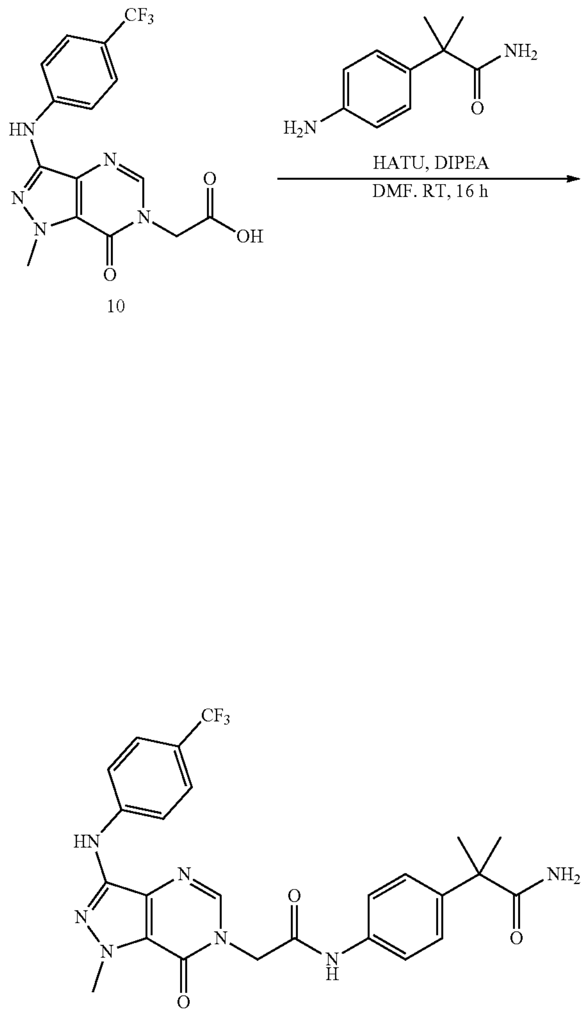

10

21

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (271 mg, 0.74 mmol) in DMF (3 mL) were added HATU (424 mg, 1.11 mmol), DIPEA (0.37 mL, 2.22 mmol) at 0° C. and reaction mixture was stirred for 5 min at same temperature. Then added 2-(4-aminophenyl)-2-methylpropanamide (196 mg, 1.11 mmol) and the reaction was stirred at RT for 16 h. The reaction mixture was quenched with ice cold water. The precipitated solid was filtered and purified by prep HPLC to afford 2-methyl-2-(4-(2-(1-methyl-7-oxo-3-((4-(trifluoromethyl)phenyl)amino)-1,7-dihydro-6H-pyrazolo[4,3-d]pyrimidin-6-yl)acetamido)phenyl)propanamide (21) (75 mg, 17%) as an off-white solid. MS (ESI) m/z 526.33 $[M+H]^+$; $^1H$ NMR (400 MHz, DMSO-$d_6$): δ 10.42 (s, 1H), 9.46 (s, 1H), 8.16 (s, 1H), 7.73 (d, J=8.4 Hz, 2H), 7.57 (d, J=8.8 Hz, 2H), 7.51 (d, J=8.4 Hz, 2H), 6.83 (d, J=4.4 Hz, 2H), 4.87 (s, 2H), 4.13 (s, 2H), 1.41 (s, 6H).

Example 13: Synthesis of N-((1S,4r)-4-((S)-2-hydroxypropoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (22) and N-((1R,4r)-4-((R)-2-hydroxypropoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (23)

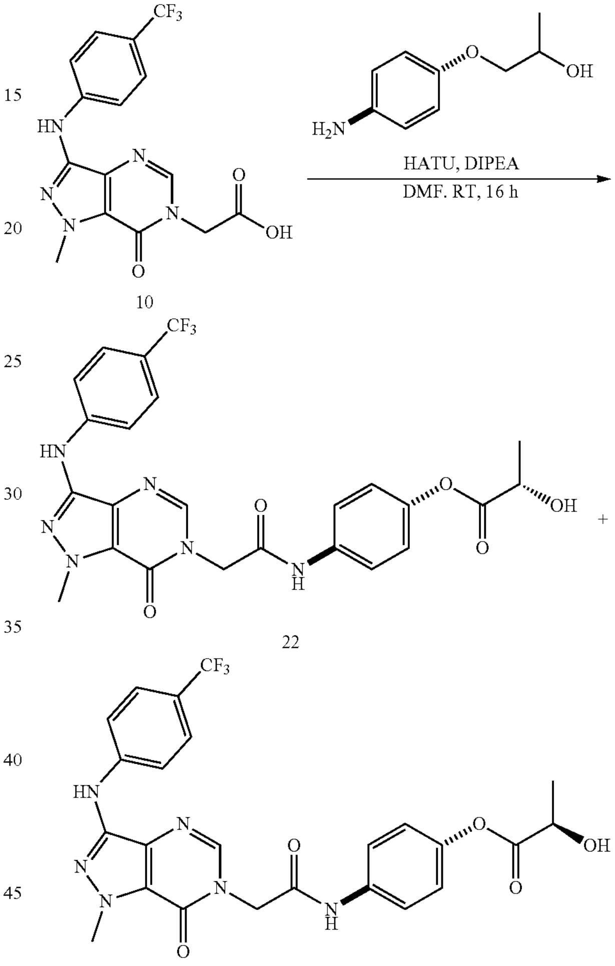

10

22

23

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (250 mg, 0.70 mmol) in DMF (3 mL) was added HATU (400 mg, 1.05 mmol) and DIPEA (290 mg, 2.10 mmol) at 0° C. and reaction mixture was stirred for 5 min at same temperature. Then added 1-(((1r,4r)-4-aminocyclohexyl)oxy)propan-2-ol (142 mg, 0.83 mmol) and the reaction was stirred at RT for 16 h. Reaction mixture was quenched with ice cold water. Precipitated solid was filtered off and dried to afford N-((trans)-4-(2-hydroxypropoxy)cyclohexyl)-2-(4-oxo-8-((5-(trifluoromethyl)pyridin-2-yl)amino)quinazolin-3(4H)-yl) acetamide (22 & 23) (320 mg) as an off-white solid. Chiral SFC separation of enantiomers to afford (22) (64 mg, 9%) & (23) (63 mg, 9%).

22 peak-1: MS (ESI) m/z 523.51 $[M+H]^+$; $^1H$ NMR (400 MHz, DMSO-$d_6$): δ 9.43 (s, 1H), 8.20 (d, J=7.6 Hz, 1H), 8.07 (s, 1H), 7.72 (d, J=8.4 Hz, 2H), 7.56 (d, J=8.4 Hz, 2H), 4.62 (s, 2H), 4.47 (s, 1H), 4.12 (s, 3H), 3.70-3.60 (brs, 1H), 3.60-3.50 (brs, 1H), 3.30-3.10 (m, 3H), 2.11-1.90 (m, 2H), 1.90-1.80 (m, 2H), 1.30-1.15 (m, 4H), 1.01 (d, J=6.0 Hz, 3H).

23 peak-2: MS (ESI) m/z 523.51 $[M+H]^+$; $^1H$ NMR (400 MHz, DMSO-$d_6$): δ 9.43 (s, 1H), 8.21 (d, J=7.6 Hz, 1H), 8.07 (s, 1H), 7.72 (d, J=8.4 Hz, 2H), 7.56 (d, J=8.4 Hz, 2H), 4.63 (s, 2H), 4.48 (s, 1H), 4.12 (s, 3H), 3.70-3.60.

Example 14: Synthesis of N-((trans)-4-(2-hydroxy-2-methylpropoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (24)

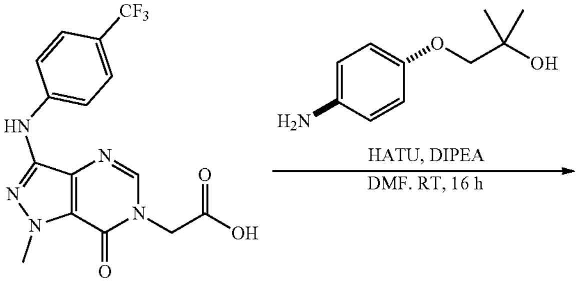

10

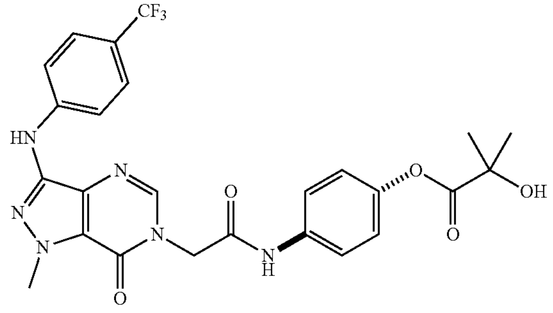

24

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (271 mg, 0.74 mmol) in DMF (3 mL) were added HATU (424 mg, 1.11 mmol), DIPEA (0.37 mL, 2.22 mmol) at 0° C. and reaction mixture was stirred for 5 min at same temperature. Then added 1-(((trans)-4-aminocyclohexyl)oxy)-2-methylpropan-2-ol (166 mg, 0.88 mmol) and the reaction was stirred at RT for 16 h. The reaction mixture was quenched with ice cold water. The precipitated solid was filtered and purified by prep HPLC to afford N-((trans)-4-(2-hydroxy-2-methylpropoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (24) (75 mg, 25%) as an off-white solid. MS (ESI) m/z 537.36 $[M+H]^+$; $^1H$ NMR (400 MHz, DMSO-$d_6$): δ 9.43 (s, 1H), 8.20 (d, J=7.2 Hz, 1H), 8.07 (s, 1H), 7.72 (d, J=8.4 Hz, 2H), 7.56 (d, J=8.8 Hz, 2H), 4.63 (s, 2H), 4.20 (s, 1H), 4.12 (s, 3H), 4.54 (brs, 1H), 3.23-3.21 (m, 1H), 3.14 (s, 2H), 1.97-1.93 (m, 2H), 1.83-1.79 (m, 2H), 1.25-1.20 (m, 4H), 1.05 (s, 6H).

Example 15: Synthesis of (R)-N-(4-((1-hydroxypropan-2-yl)oxy)phenyl)-2-(1-methyl-7-oxo-3-((4-(trifluoromethyl)phenyl)amino)-1,7-dihydro-6H-pyrazolo[4,3-d]pyrimidin-6-yl)acetamide (25) and (S)-N-(4-((1-hydroxypropan-2-yl)oxy)phenyl)-2-(1-methyl-7-oxo-3-((4-(trifluoromethyl)phenyl)amino)-1,7-dihydro-6H-pyrazolo[4,3-d]pyrimidin-6-yl) acetamide (26)

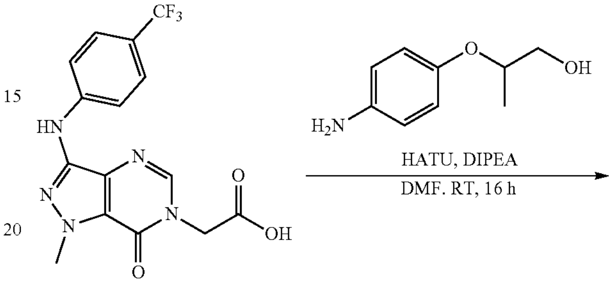

10

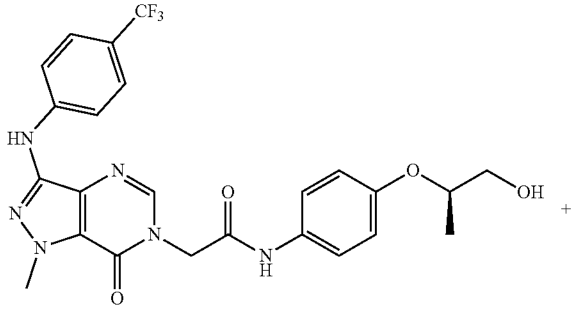

25

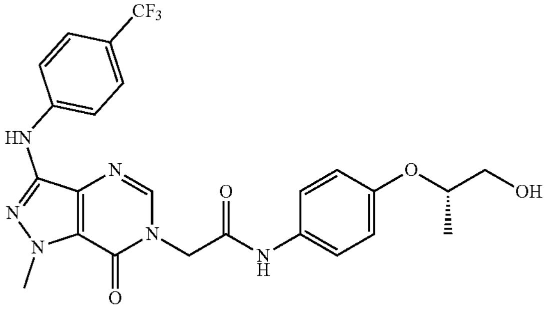

26

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (271 mg, 0.74 mmol) in DMF (3 mL) were added HATU (424 mg, 1.11 mmol), DIPEA (0.37 mL, 2.22 mmol) at 0° C. and reaction mixture was stirred for 5 min at same temperature. Then added 2-(4-aminophenoxy)propan-1-ol (185 mg, 1.11 mmol) and the reaction was stirred at RT for 16 h. The reaction mixture was quenched with ice cold water. The precipitated solid was filtered and purified by prep SFC to (R)-N-(4-((1-hydroxypropan-2-yl)oxy)phenyl)-2-(1-methyl-7-oxo-3-((4-(trifluoromethyl)phenyl)amino)-1,7-dihydro-6H-pyrazolo[4,3-d]pyrimidin-6-yl)acetamide (25) (85 mg, 22%) & (S)-N-(4-((1-hydroxypropan-2-yl)oxy)phenyl)-2-(1-methyl-7-oxo-3-((4-(trifluoromethyl)phenyl)amino)-1,7-dihydro-6H-pyrazolo[4,3-d]pyrimidin-6-yl)acetamide (26) (77 mg, 20%) as an off-white solid.

25 peak-1: MS (ESI) m/z 517.45 $[M+H]^+$; $^1H$ NMR (400 MHz, DMSO-$d_6$): δ 10.29 (s, 1H), 9.46 (s, 1H), 8.15 (s, 1H), 7.73 (d, J=8.4 Hz, 2H), 7.57 (d, J=8.8 Hz, 2H), 7.47 (d, J=8.4 Hz, 2H), 6.89 (d, J=9.2 Hz, 2H), 4.85 (s, 2H), 4.82 (t, J=5.6 Hz, 1H), 4.36-4.32 (m, 1H), 4.13 (s, 3H), 3.55-3.50 (m, 1H), 3.45-3.40 (m, 1H), 1.17 (d, J=6.0 Hz, 3H).

26 peak-2: MS (ESI) m/z 517.45 $[M+H]^+$; $^1H$ NMR (400 MHz, DMSO-$d_6$): δ 10.29 (s, 1H), 9.46 (s, 1H), 8.15 (s, 1H), 7.73 (d, J=8.4 Hz, 2H), 7.57 (d, J=8.8 Hz, 2H), 7.47 (d, J=9.2 Hz, 2H), 6.89 (d, J=8.8 Hz, 2H), 4.85 (s, 2H), 4.81 (t, J=5.6 Hz, 1H), 4.36-4.32 (m, 1H), 4.13 (s, 3H), 3.55-3.49 (m, 1H), 3.45-3.40 (m, 1H), 1.17 (d, J=6.0 Hz, 3H).

Example 16: Synthesis of N-((trans)-4-(1-hydroxy-2-methylpropan-2-yl)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (27)

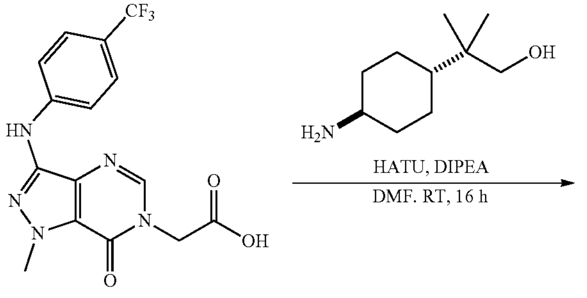

10

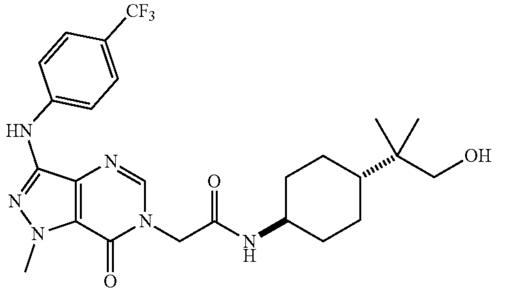

27

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (271 mg, 0.74 mmol) in DMF (3 mL) were added HATU (424 mg, 1.11 mmol), DIPEA (0.37 mL, 2.22 mmol) at 0° C. and reaction mixture was stirred for 5 min at same temperature. Then added 2-((trans)-4-aminocyclohexyl)-2-methylpropan-1-ol (150 mg, 0.88 mmol) and the reaction was stirred at RT for 16 h. The reaction mixture was quenched with ice cold water. The precipitated solid was filtered and purified by prep HPLC afford N-((trans)-4-(1-hydroxy-2-methylpropan-2-yl)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (27) (110 mg, 28%) as an off-white solid. MS (ESI) m/z 519.40 $[M-H]^-$; $^1H$ NMR (400 MHz, DMSO-$d_6$): δ 9.43 (s, 1H), 8.17 (d, J=7.6 Hz, 1H), 8.07 (s, 1H), 7.72 (d, J=8.4 Hz, 2H), 7.56 (d, J=8.8 Hz, 2H), 4.65 (s, 2H), 4.40 (t, J=5.6 Hz, 1H), 4.13 (s, 3H), 4.46-3.42 (m, 1H), 3.13 (d, J=5.2 Hz, 2H), 1.86-1.83 (m, 2H), 1.71-1.68 (m, 2H), 1.23-0.98 (m, 4H), 0.73 (s, 6H).

Example 17: N-((trans)-4-hydroxycyclohexyl)-2-(1-methyl-7-oxo-3-((4-(trifluoromethyl)phenyl)amino)-1,7-dihydro-6H-pyrazolo[4,3-d]pyrimidin-6-yl)acetamide (28)

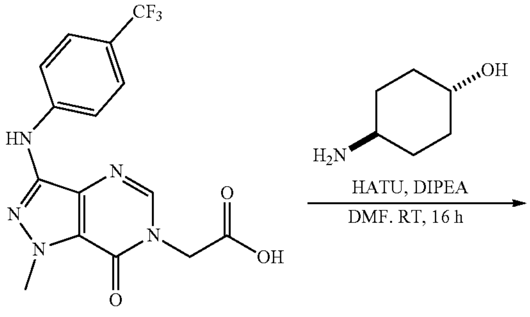

10

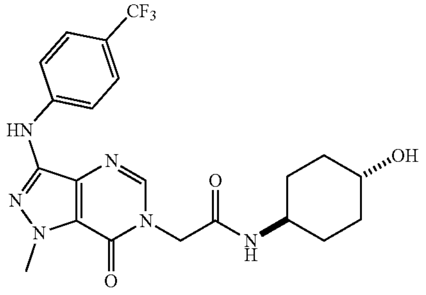

28

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (250 mg, 0.68 mmol) in DMF (5 mL) were added HATU (387 mg, 1.02 mmol), DIPEA (0.53 mL, 3.06 mmol) at 0° C. and reaction mixture was stirred for 5 min at same temperature. Then added (trans)-4-aminocyclohexan-1-ol (93 mg, 0.816 mmol) and the reaction was stirred at RT for 16 h. The reaction mixture was quenched with ice cold water. The precipitated solid was filtered and purified by prep HPLC to afford N-((trans)-4-hydroxycyclohexyl)-2-(1-methyl-7-oxo-3-((4-(trifluoromethyl)phenyl)amino)-1,7-dihydro-6H-pyrazolo[4,3-d]pyrimidin-6-yl)acetamide (28) (95 mg, 30%) as an off-white solid. MS (ESI) m/z 465.35 $[M+H]^+$; $^1H$ NMR (400 MHz, DMSO-$d_6$): δ 9.43 (s, 1H), 8.16 (d, J=7.6 Hz, 1H), 8.06 (s, 1H), 7.72 (d, J=8.4 Hz, 2H), 7.56 (d, J=8.8 Hz, 2H), 4.62 (s, 2H), 4.52 (d, J=4.4 Hz, 1H), 3.49-3.36 (m, 2H), 1.82-1.76 (m, 4H), 1.23-1.17 (m, 4H).

Example 18: N-((1r,4r)-4-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (32)

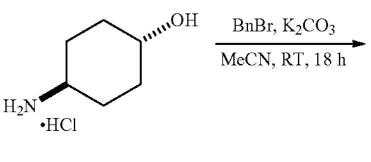

-continued

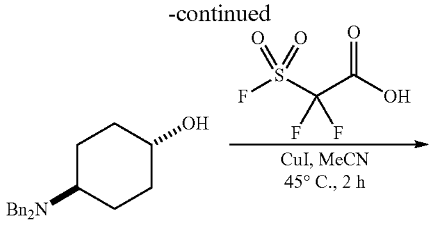

29

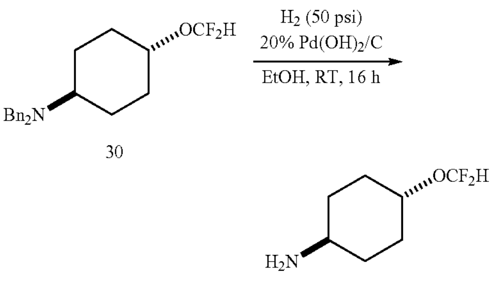

30

31

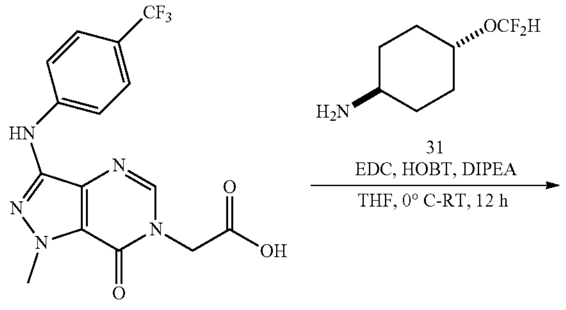

31

10

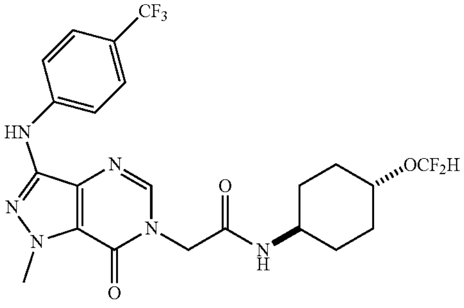

32

To a stirred solution of trans-4-aminocyclohexan-1-ol (5 g, 33 mmol) in acetonitrile (100 mL) at 0° C. were added $K_2CO_3$ (18 g, 132 mmol) followed by benzyl bromide (8.2 g, 69 mmol) and the reaction mixture was stirred at RT for 18 h. Reaction mixture was filtered through celite pad and the filtrate was evaporated under reduced pressure. Resultant solid was washed with n-pentane to afford trans-4-(dibenzylamino)cyclohexan-1-ol (29) (8 g, 82%) as a white solid. This was used in next step without further purification. MS (ESI) m/z 296.36 $[M+H]^+$; $^1H$ NMR (400 MHz, DMSO-$d_6$): δ 7.38-7.24 (m, 8H), 7.23-7.14 (m, 2H), 4.41 (d, J=4.2 Hz, 1H), 3.55 (s, 4H), 2.45-2.28 (m, 1H), 1.90-1.70 (m, 4H), 1.50-1.30 (m, 2H), 1.10-0.90 (m, 2H).

To a stirred solution of trans-4-(dibenzylamino)cyclohexan-1-ol (29) (2 g, 6 mmol) in acetonitrile (50 mL) was added CuI (0.258 g, 1.3 mmol) at RT. The reaction mixture temperature was heated to 45° C. and added 2,2-difluoro-2-(fluorosulfonyl)acetic acid (2.4 g, 13 mmol). Then the reaction mixture was stirred at the same temperature for 1 h. Again 2,2-difluoro-2-(fluorosulfonyl)acetic acid (2.4 g, 13 mmol) was added and continued the stirring for another 1 h. Then the reaction mixture was cooled to RT and filtered through celite pad. Filtrate was evaporated, the residue was dissolved in EtOAc and washed with saturated aq. $NaHCO_3$ solution followed by water. The organic layer was dried over anhydrous $Na_2SO_4$, filtered and concentrated to obtain the crude compound which was purified by flash column chromatography over 100-200 silica using 5% EtOAc in hexanes as an eluent to afford trans-N,N-dibenzyl-4-(difluoromethoxy)cyclohexan-1-amine (30) (1.8 g, 86%) as a white solid. MS (ESI) m/z 346.39 $[M+H]^+$; $^1H$ NMR (400 MHz, DMSO-$d_6$): δ 7.38-7.26 (m, 8H), 7.23-7.15 (m, 2H), 6.65 (t, J=77.2 Hz, 1H), 4.05-3.90 (m, 1H), 3.56 (s, 4H), 2.48-2.35 (m, 1H), 1.97 (d, J=10.4 Hz, 2H), 1.82 (d, J=11.6 Hz, 2H), 1.55-1.42 (m, 2H), 1.30-1.15 (m, 2H).

To a stirred solution of trans-N,N-dibenzyl-4-(difluoromethoxy)cyclohexan-1-amine (30) (0.9 g, 2.6 mmol) in EtOH (10 mL) was added 20% Pd(OH)2/C (0.6 g) and reaction mixture was stirred under hydrogenation (50 PSI) atmosphere for 16 h. Reaction mixture was passed through celite pad and the filtrate was concentrated to obtain trans-4-(difluoromethoxy)cyclohexanamine (31) (350 mg, 81%) as a colorless oil that was used in next step without purification. MS (ESI) m/z 166.37 $[M+H]^+$.

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (4.8 g, 13.07 mmol) in THF (48 mL) were added DIPEA (7.23 mL, 39.23 mmol), EDC·HCl (3.74 g, 19.61 mmol), HOBT (2.64 g, 19.61 mmol) at 0° C. and reaction mixture was stirred for 15 min at room temperature. Then added (1r,4r)-4-(difluoromethoxy)cyclohexan-1-amine (31) (2.16 g, 13.07 mmol) and the reaction was stirred at RT for 12 h. After completion of the reaction by TLC, reaction mixture was quenched with water (100 mL) and extracted with EtOAc (2×200 mL). Organic layer was dried over anhydrous $Na_2SO_4$, filtered and concentrated to obtain the crude that was purified by flash column chromatography over 100-200 silica using 90% EtOAc in hexanes as an eluent to afford N-((1r,4r)-4-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (32) (3.5 g, 57%) as an off-white solid. MS (ESI) m/z 515.61 $[M+H]^+$; $^1H$ NMR (400 MHz, DMSO-$d_6$): δ 9.43 (s, 1H), 8.23 (d, J=7.2 Hz, 1H), 8.07 (s, 1H), 7.72 (d, J=8.4 Hz, 2H), 7.56 (d, J=8.8 Hz, 2H), 6.69 (t, J=76.6 Hz, 1H), 4.63 (s, 2H), 4.12-4.03 (m, 4H), 3.57-3.55 (m, 1H), 1.96-1.94 (m, 2H), 1.85-1.82 (m, 2H), 1.49-1.41 (m, 2H), 1.34-1.32 (m, 2H).

Example 19: Synthesis of N-((1s,4s)-4-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (36)

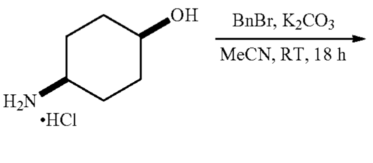

-continued

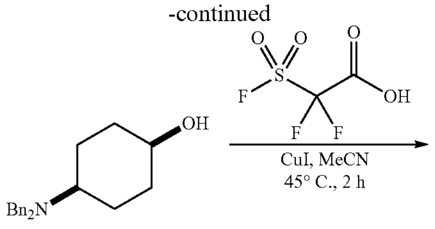

33

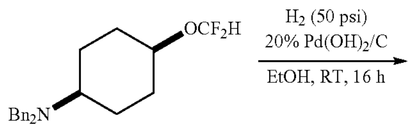

34

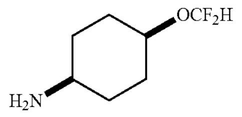

35

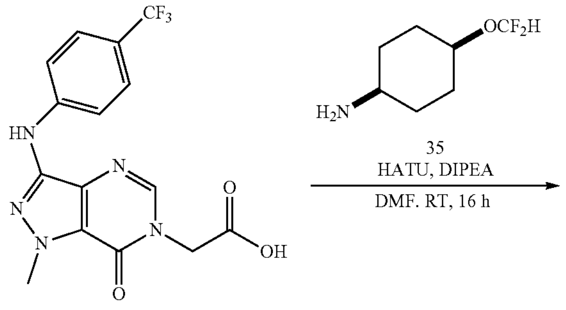

10

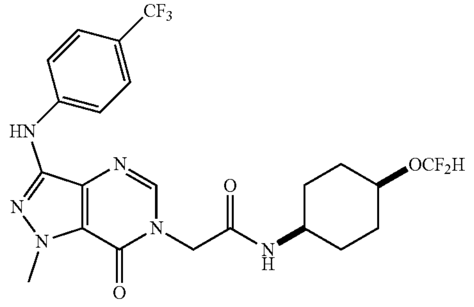

36

To a stirred solution of (1s,4s)-4-aminocyclohexan-1-ol (5 g, 33.11 mmol) in acetonitrile (100 mL) were added $K_2CO_3$ (19.2 g, 139.07 mmol) followed by benzyl bromide (17 g, 99.33 mmol) at ice temperature and the reaction mixture was stirred at RT for 18 h. The mixture was quenched with water and extracted with EtOAc. The organic layer was dried over anhydrous $Na_2SO_4$, filtered and concentrated. The residue was stirred with pet ether, and filtered to afford as (1s,4s)-4-(dibenzylamino)cyclohexan-1-ol (33) (7 g, 72.16%) as a white solid. MS (ESI) m/z 296.27 $[M+H]^+$.

To a stirred solution of (1s,4s)-4-(dibenzylamino)cyclohexan-1-ol (33) (4.4 g, 14.91 mmol) in acetonitrile (45 mL) was added CuI (566 mg, 2.98 mmol) and reaction mixture was heated to 45° C. and then added 2,2-difluoro-2-(fluorosulfonyl)acetic acid (9.29 g, 52.20 mmol) and stirred for 2 h. Reaction mixture was slowly quenched with aq. $NaHCO_3$ solution and extracted with EtOAc. The organic layer was dried over anhydrous $Na_2SO_4$, filtered and concentrated. The residue was purified by silica gel column chromatography to afford (1s,4s)-N,N-dibenzyl-4-(difluoromethoxy)cyclohexan-1-amine (34) (3.2 g, 62%) as a white solid. MS (ESI) m/z 346.70 $[M+H]^+$.

To a stirred solution of (1s,4s)-N,N-dibenzyl-4-(difluoromethoxy)cyclohexan-1-amine (34) (2 g, 5.79 mmol) in EtOH (10 mL) was added 10% Pd/C (8 g) and reaction mixture was stirred at RT under hydrogen (70 psi) atmosphere for 16 h. The reaction mixture was filtered through a celite pad and the filtrate was concentrated to obtain (1s, 4s)-4-(difluoromethoxy)cyclohexan-1-amine (35) (0.45 g, 47%). MS (ESI) m/z 166.12 $[M+H]^-$.

To a stirred solution of 2-(1-methyl-7-oxo-3-((4-(trifluoromethyl)phenyl)amino)-1,7-dihydro-6H-pyrazolo[4,3-d] pyrimidin-6-yl)acetic acid (10) (300 mg, 0.82 mmol) in DMF (3 mL) was added HATU (465 mg, 1.23 mmol), DIPEA (0.43 mL, 2.45 mmol) at 0° C. and reaction mixture was stirred for 15 min at same temperature. Added (1s,4s)-4-(difluoromethoxy)cyclohexan-1-amine (35) (150 mg, 0.89 mmol) and the reaction was stirred at RT for 16 h. The reaction mixture was diluted with water and extracted with EtOAc (2x50 mL). The organic layer was evaporated the crude was purified through silica column followed by Prep SFC to afford N-((1s,4s)-4-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (36) (51 mg, 12%) as an off-white solid. MS (ESI) m/z 515.20 $[M+H]^+$; $^1H$ NMR (400 MHz, DMSO-$d_6$): δ 9.43 (s, 1H), 8.27 (d, J=8.00 Hz, 1H), 8.08 (s, 1H), 7.72 (d, J=8.80 Hz, 2H), 7.56 (d, J=8.80 Hz, 2H), 6.71 (t, J=72.8 Hz, 1H), 4.65 (s, 2H), 4.30-4.20 (m, 1H), 4.12 (s, 3H), 3.70-3.60 (m, 1H), 1.90-1.80 (m, 2H), 1.70-1.50 (m, 6H).

Example 20: Synthesis of 2-(1-methyl-7-oxo-3-((4-(trifluoromethyl)phenyl)amino)-1,7-dihydro-6H-pyrazolo[4,3-d]pyrimidin-6-yl)-N-((1r,4r)-4-((tetrahydro-2H-pyran-4-yl)methoxy)cyclohexyl) acetamide (39)

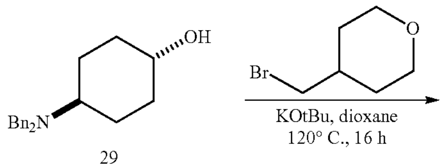

29

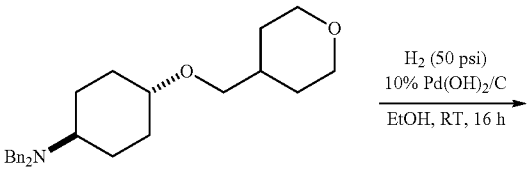

37

-continued

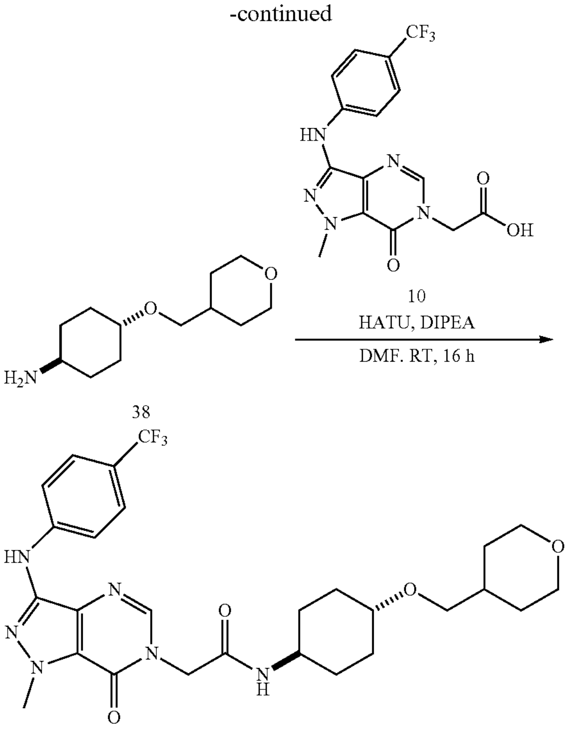

10

38

39

To a stirred solution of (1r,4r)-4-(dibenzylamino)cyclohexan-1-ol (29) (2 g, 6.77 mmol) in dioxane (20 mL) were added KO$^t$Bu (4.0 g, 33.89 mmol) followed by 4-(bromomethyl)tetrahydro-2H-pyran (6.0 mL, 40.67 mmol) at ice temperature and the reaction mixture was stirred at 120° C. for 16 h. The reaction mixture was quenched with water and extracted with EtOAc. Organic layer was dried over anhydrous $Na_2SO_4$, filtered and concentrated. The residue was purified through silica gel column to afford (1r,4r)-N,N-dibenzyl-4-((tetrahydro-2H-pyran-4-yl)methoxy)cyclohexan-1-amine (37) (750 mg, crude). MS (ESI) m/z 394.54 $[M+H]^+$.

To a stirred solution of methyl (1r,4r)-N,N-dibenzyl-4-((tetrahydro-2H-pyran-4-yl)methoxy)cyclohexan-1-amine (37) (750 mg, 1.91 mmol) in EtOH (2 mL) was added 10% Pd/C (2 g) and the reaction mixture was stirred at RT under hydrogen (70 Psi) atmosphere for 16 h. The reaction mixture was filtered through a celite pad and the filtrate was concentrated to obtain (1r,4r)-4-((tetrahydro-2H-pyran-4-yl)methoxy)cyclohexan-1-amine (38) (390 mg, crude).

To a stirred solution of 2-(1-methyl-7-oxo-3-((4-(trifluoromethyl)phenyl)amino)-1,7-dihydro-6H-pyrazolo[4,3-d]pyrimidin-6-yl)acetic acid (10) (350 mg, 0.95 mmol) in DMF (5 mL) were added HATU (720 mg, 1.90 mmol), DIPEA (0.52 mL, 2.86 mmol) at 0° C. and reaction mixture was stirred for 5 min at same temperature. (1r,4r)-4-((tetrahydro-2H-pyran-4-yl)methoxy)cyclohexan-1-amine (38) (406 mg, 1.90 mmol) was then added and the reaction was stirred at RT for 16 h. The reaction mixture was diluted with water and extracted with EtOAc (2×50 mL). The combined organic layer was evaporated and the residue was purified through silica column (60-120 mesh) followed by RP prep HPLC to afford 2-(1-methyl-7-oxo-3-((4-(trifluoromethyl)phenyl)amino)-1,7-dihydro-6H-pyrazolo[4,3-d]pyrimidin-6-yl)-N-((1r,4r)-4-((tetrahydro-2H-pyran-4-yl)methoxy)cyclohexyl)acetamide (39) (40 mg, 5% yield) as an off-white solid. MS (ESI) m/z 563.61 $[M+H]^+$; $^1H$ NMR (400 MHz, DMSO-$d_6$): δ 9.43 (s, 1H), 8.20 (d, J=7.80 Hz, 1H), 8.07 (s, 1H), 7.72 (d, J=8.40 Hz, 2H), 7.56 (d, J=8.40 Hz, 2H), 4.62 (s, 2H), 4.12 (s, 3H), 3.80-3.70 (m, 2H), 3.60-3.50 (m, 1H), 3.30-3.20 (m, 5H), 2.00-1.90 (m, 2H), 1.90-1.80 (m, 2H), 1.80-1.65 (m, 1H), 1.60-1.50 (m, 2H), 1.30-1.10 (m, 6H).

Example 21: Synthesis of N-((1S,3S)-3-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide & N-((1R,3R)-3-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide (43 & 44)

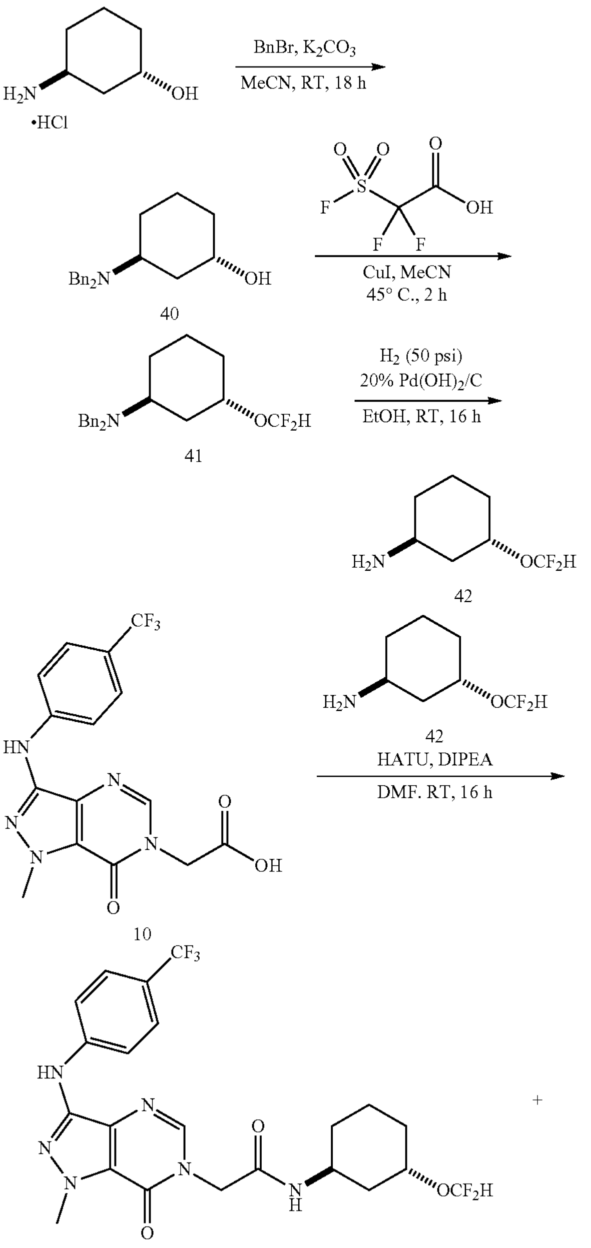

40

41

42

42

10

43

-continued

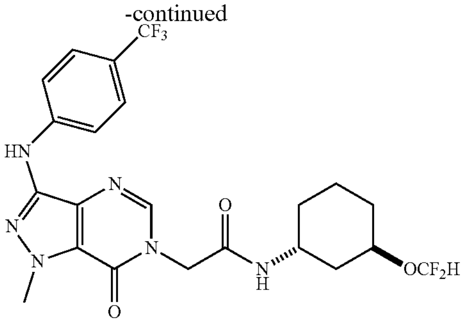

44

To a stirred solution of (trans)-3-aminocyclohexan-1-ol hydrochloride (6 g, 52.17 mmol) in acetonitrile (60 mL) were added $K_2CO_3$ (30.28 g, 219.13 mmol) followed by benzyl bromide (26.76 g, 156.52 mmol) at ice temperature and the reaction mixture was stirred at RT for 18 h. The mixture was quenched with water and extracted with EtOAc. The organic layer was dried over anhydrous $Na_2SO_4$, filtered, and concentrated to obtain the crude. Thus obtained brown crude was stirred with pet ether, and filtered to afford as (trans)-3-(dibenzylamino)cyclohexan-1-ol (40) (6.5 g, 42% yield) as a brown solid. MS (ESI) m/z 296.43 $[M+H]^-$.

To a stirred solution of (trans)-3-(dibenzylamino)cyclohexan-1-ol (40) (4 g, 13.55 mmol) in acetonitrile (40 mL) was added CuI (515 mg, 2.71 mmol) and reaction mixture was heated to 45° C. and then added 2,2-difluoro-2-(fluorosulfonyl)acetic acid (8.44 g, 47.45 mmol and stirred for 2 h. Reaction mixture was slowly Quenched with aq. $NaHCO_3$ solution, extracted with EtOAc. The organic layer was dried over anhydrous $Na_2SO_4$, filtered and concentrated. The residue was purified through silica gel column to afford gummy material as N,N-dibenzyl-3-(difluoromethoxy)cyclohexan-1-amine (41) (3 g, 65% yield). MS (ESI) m/z 346.28 $[M+H]^-$.

To a stirred solution of N,N-dibenzyl-3-(difluoromethoxy)cyclohexan-1-amine (41) (1.5 g, 4.34 mmol) in EtOH (22 mL) was added 10% Pd/C (6 g) and reaction mixture was stirred at RT under hydrogen (70 Psi) atmosphere for 16 h. The reaction mixture was filtered through a celite pad and the filtrate was concentrated to obtain 3-(difluoromethoxy)cyclohexan-1-amine (42) (0.450 g, 63% yield). MS (ESI) m/z 166.08 $[M+H]^-$.

To a stirred solution of 2-(1-methyl-7-oxo-3-((4-(trifluoromethyl)phenyl)amino)-1,7-dihydro-6H-pyrazolo[4,3-d] pyrimidin-6-yl)acetic acid (10) (400 mg, 1.08 mmol) in DMF (4 mL) was added HATU (621 mg, 1.63 mmol), DIPEA (0.6 mL, 3.26 mmol) at 0° C. and the reaction mixture was stirred for 5 min at same temperature. Added 3-(difluoromethoxy)cyclohexan-1-amine (42) (179 mg, 1.08 mmol) and the reaction mixture was stirred at RT for 16 h. The reaction mixture was diluted with water and extracted with EtOAc (2×50 mL). The organic layer was evaporated and the residue was purified through silica column (60-120 mesh) followed by Prep SFC afforded both trans isomers of N-((1,3)-3-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide with unknown absolute stereochemistry as off-white solids (43) (105 mg, 19% yield) and (44) (125 mg, 22% yield).

Compound 43: MS (ESI) m/z 515.23 $[M+H]^+$; $^1H$ NMR (400 MHz, DMSO-$d_6$): δ 9.43 (s, 1H), 8.25 (d, J=8.00 Hz, 1H), 8.07 (s, 1H), 7.72 (d, J=8.80 Hz, 2H), 7.56 (d, J=8.80 Hz, 2H), 6.69 (t, J=72.8 Hz, 1H), 4.64 (s, 2H), 4.50-4.40 (m, 1H), 4.12 (s, 3H), 4.00-3.90 (m, 1H), 1.90-1.80 (m, 1H), 1.80-1.50 (m, 6H), 1.40-1.20 (m, 1H).

Compound 44: MS (ESI) m/z 515.23 $[M+H]^+$; $^1H$ NMR (400 MHz, DMSO-$d_6$): δ 9.44 (s, 1H), 8.26 (d, J=8.00 Hz, 1H), 8.08 (s, 1H), 7.72 (d, J=8.80 Hz, 2H), 7.56 (d, J=8.80 Hz, 2H), 6.69 (t, J=72.8 Hz, 1H), 4.64 (s, 2H), 4.50-4.40 (m, 1H), 4.12 (s, 3H), 4.00-3.90 (m, 1H), 1.90-1.80 (m, 1H), 1.80-1.50 (m, 6H), 1.40-1.20 (m, 1H).

Example 22: Synthesis of N-((1S,3R)-3-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl)acetamide & N-((1R,3S)-3-(difluoromethoxy)cyclohexyl)-2-(1-methyl-7-oxo-3-((4-(trifluoromethyl)phenyl)amino)-1,7-dihydro-6H-pyrazolo[4,3-d]pyrimidin-6-yl) acetamide (48 & 49)

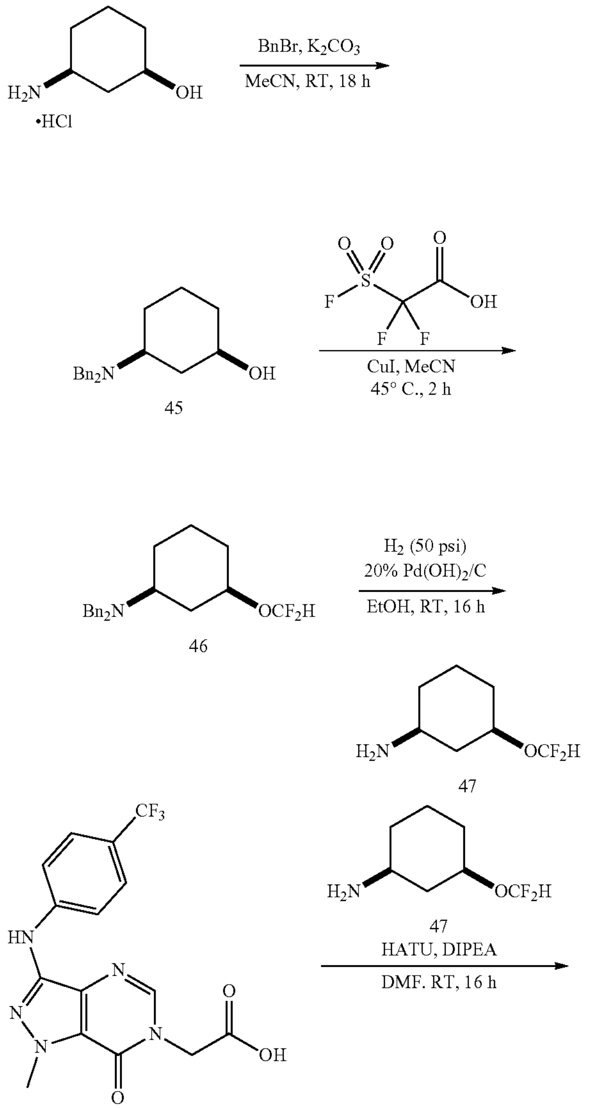

45 46 47 47 10

-continued

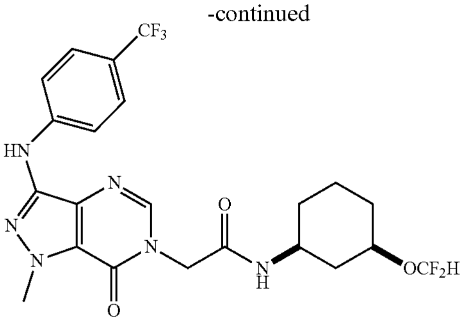

48

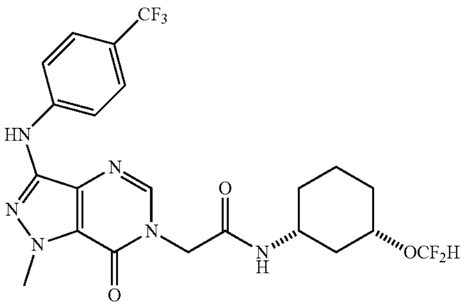

49

To a stirred solution of (cis)-3-aminocyclohexan-1-ol hydrochloride (6 g, 52.17 mmol) in acetonitrile (60 mL) were added $K_2CO_3$ (30.28 g, 219.13 mmol) followed by benzyl bromide (26.76 g, 156.52 mmol) at ice temperature and the reaction mixture was stirred at RT for 18 h. The mixture was quenched with water and extracted with EtOAc. The organic layer was dried over anhydrous $Na_2SO_4$, filtered and concentrated to obtain the crude. Thus obtained brown crude was stirred with pet ether, and filtered to afford as (cis)-3-(dibenzylamino)cyclohexan-1-ol (45) (6.5 g, 42% yield) as a brown solid. MS (ESI) m/z 296.43 $[M+H]^-$.

To a stirred solution of 3-(dibenzylamino)cyclohexan-1-ol (45) (4 g, 13.55 mmol) in acetonitrile (40 mL) was added CuI (515 mg, 2.71 mmol) and reaction mixture was heated to 45° C. and then added 2,2-difluoro-2-(fluorosulfonyl) acetic acid (8.44 g, 47.45 mmol and stirred for 2 h. Reaction mixture was slowly Quenched with aq. $NaHCO_3$ solution, extracted with EtOAc. The organic layer was dried over anhydrous $Na_2SO_4$, filtered and concentrated. The residue was purified through a silica gel column to afford gummy material as N,N-dibenzyl-3-(difluoromethoxy)cyclohexan-1-amine (46) (3 g, 65% yield). MS (ESI) m/z 346.28 $[M+H]^-$.

To a stirred solution of N,N-dibenzyl-3-(difluoromethoxy)cyclohexan-1-amine (46) (1.5 g, 4.34 mmol) in EtOH (22 mL) was added 10% Pd/C (6 g) and reaction mixture was stirred at RT under hydrogen (70 Psi) atmosphere for 16 h. The reaction mixture was filtered through celite pad and the filtrate was concentrated to obtain 3-(difluoromethoxy)cyclohexan-1-amine (47) (0.450 g, 63% yield). MS (ESI) m/z 166.08 $[M+H]^-$.

To a stirred solution of 2-(1-methyl-7-oxo-3-((4-(trifluoromethyl)phenyl)amino)-1,7-dihydro-6H-pyrazolo[4,3-d] pyrimidin-6-yl)acetic acid (10) (400 mg, 1.08 mmol) in DMF (4 mL) was added HATU (621 mg, 1.63 mmol), DIPEA (0.6 mL, 3.26 mmol) at 0° C. and reaction mixture was stirred for 5 min at same temperature. Added 3-(difluoromethoxy)cyclohexan-1-amine (47) (179 mg, 1.08 mmol)

and the reaction was stirred at RT for 16 h. The reaction mixture was diluted with water and extracted with EtOAc (2×50 mL). The organic layer was evaporated and the residue was purified through silica column (60-120 mesh) followed by SFC to afford both cis isomers of N-((1,3)-3-(difluoromethoxy)cyclohexyl)-2-(1-methyl-7-oxo-3-((4-(trifluoromethyl)phenyl)amino)-1,7-dihydro-6H-pyrazolo [4,3-d]pyrimidin-6-yl)acetamide with unknown absolute stereochemistry (48) (15 mg, 3% yield) as an off-white solid and (49) (2 mg, 1% yield) as an off-white solid.

Compound 48: MS (ESI) m/z 515.23 $[M+H]^+$; $^1H$ NMR (400 MHz, DMSO-$d_6$): δ 9.44 (s, 1H), 8.32 (d, J=7.20 Hz, 1H), 8.08 (s, 1H), 7.72 (d, J=8.80 Hz, 2H), 7.56 (d, J=8.80 Hz, 2H), 6.70 (t, J=72.8 Hz, 1H), 4.63 (s, 2H), 4.12 (s, 3H), 4.10-4.00 (m, 1H), 3.65 (m, 1H), 2.14 (m, 1H), 1.93 (m, 1H), 1.73 (m, 2H), 1.35-1.23 (m, 4H).

Compound 49: MS (ESI) m/z 515.33 $[M+H]^+$; $^1H$ NMR (400 MHz, DMSO-$d_6$): δ 9.44 (s, 1H), 8.32 (d, J=8.4 Hz, 1H), 8.08 (s, 1H), 7.73 (d, J=8.4 Hz, 2H), 7.57 (d, J=8.80 Hz, 2H), 6.70 (t, J=76.4 Hz, 1H), 4.63 (s, 2H), 4.12 (s, 3H), 4.10-4.00 (m, 1H), 3.65 (m, 1H), 2.14 (m, 1H), 1.93 (m, 1H), 1.73 (m, 2H), 1.29-1.11 (m, 4H).

Example 23: Synthesis of N-((1r,4r)-4-(2-hydroxy-2-methylpropoxy)cyclohexyl)-2-(1-methyl-7-oxo-3-((5-(trifluoromethyl)pyridin-2-yl)amino)-1,7-dihydro-6H-pyrazolo[4,3-d]pyrimidin-6-yl)acetamide (52)

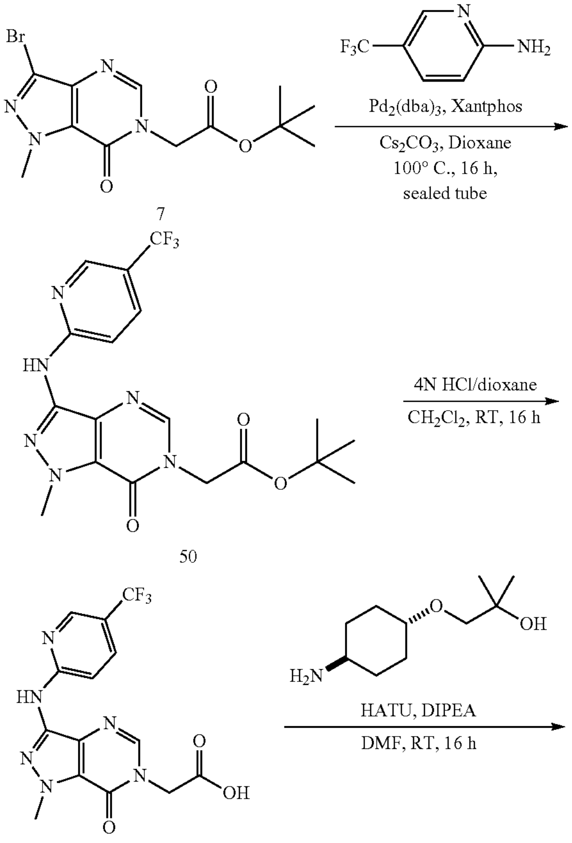

7

50

51

-continued

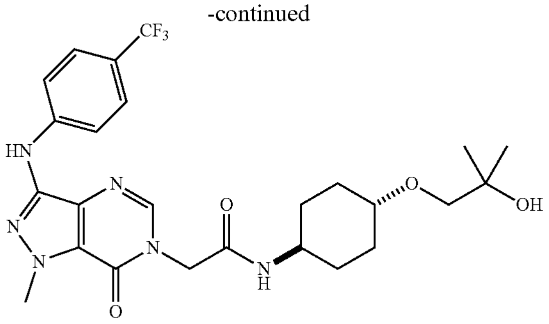

52

To a stirred solution of tert-butyl 2-(3-bromo-1-methyl-7-oxo-1,7-dihydro-6H-pyrazolo[4,3-d]pyrimidin-6-yl)acetate (7) (500 mg, 1.46 mmol) in 1,4 dioxane (15 mL) were added 5-(trifluoromethyl)pyridin-2-amine (190 mg, 1.18 mmol) and cesium carbonate (1.42 g, 4.38 mmol). The reaction was degassed with argon for 15 min, then added $Pd_2(dba)_3$ (267 mg, 0.29 mmol) and Xantphos (168 mg, 0.29 mmol), the reaction mixture again degassed with argon for 5 min, then reaction mixture was stirred at 100° C. for 16 h. The reaction mixture was diluted with ice cold water and extracted with EtOAc (2×15 mL). The organic layer was dried over anhydrous $Na_2SO_4$, filtered and concentrated. The residue was purified by silica column to afford tert-butyl 2-(1-methyl-7-oxo-3-((5-(trifluoromethyl)pyridin-2-yl)amino)-1,7-dihydro-6H-pyrazolo[4,3-d]pyrimidin-6-yl)acetate (50) (200 mg, 32% yield) as a pale yellow solid. MS (ESI) m/z 425.25 $[M+H]^+$.

To a stirred solution of tert-butyl 2-(1-methyl-7-oxo-3-((5-(trifluoromethyl)pyridin-2-yl)amino)-1,7-dihydro-6H- pyrazolo[4,3-d]pyrimidin-6-yl)acetate (50) (200 mg, 0.47 mmol) in 1,4-dioxane (2 mL) was added 4M HCl in dioxane (3 mL) at 0° C. and the reaction mixture was stirred at RT for 16 h. The reaction mixture was evaporated to afford 2-(1-methyl-7-oxo-3-((5-(trifluoromethyl)pyridin-2-yl)amino)-1,7-dihydro-6H-pyrazolo[4,3-d]pyrimidin-6-yl)acetic acid (51) (150 mg, 90%) as an off-white solid. MS (ESI) m/z 369.0 $[M+H]^+$.

To a stirred solution of 2-(1-methyl-7-oxo-3-((5-(trifluoromethyl)pyridin-2-yl)amino)-1,7-dihydro-6H-pyrazolo[4,3-d]pyrimidin-6-yl)acetic acid (51) (150 mg, 0.40 mmol) in DMF (3 mL) was added HATU (231 mg, 0.61 mmol), DIPEA (0.21 mL, 1.22 mmol) at 0° C. and the reaction mixture was stirred for 5 min at same temperature. Added 1-(((1r,4r)-4-aminocyclohexyl)oxy)-2-methylpropan-2-ol (114 mg, 0.61 mmol) and the reaction was stirred at RT for 16 h. The reaction mixture was diluted with water and extracted with ethyl acetate (2×50 mL). The organic layer was evaporated and the residue was purified by SFC prep to afforded N-((1r,4r)-4-(2-hydroxy-2-methylpropoxy)cyclohexyl)-2-(1-methyl-7-oxo-3-((5-(trifluoromethyl)pyridin-2-yl)amino)-1,7-dihydro-6H-pyrazolo[4,3-d]pyrimidin-6-yl)acetamide (52) (40 mg, 10% yield) as an off-white solid. MS (ESI) m/z 538.19 $[M+H]^+$; $^1H$ NMR (400 MHz, DMSO-$d_6$): δ 9.65 (s, 1H), 8.42 (s, 1H), 8.20 (d, J=7.2 Hz, 1H), 8.02 (s, 1H), 7.89 (d, J=6.80 Hz, 1H), 7.17 (d, J=8.8 Hz, 1H), 4.62 (s, 2H), 4.20 (s, 1H), 4.14 (s, 3H), 3.60-3.50 (m, 1H), 3.30-3.20 (m, 1H), 3.14 (s, 2H), 2.00-1.90 (m, 2H), 1.90-1.80 (m, 2H), 1.30-1.20 (m, 4H), 1.05 (s, 6H).

Example 24: Synthesis of N-((1r,4r)-4-(difluoromethoxy)cyclohexyl)-2-(1-methyl-7-oxo-3-((5-(trifluoromethyl)pyridin-2-yl)amino)-1,7-dihydro-6H-pyrazolo[4,3-d]pyrimidin-6-yl)acetamide (55)

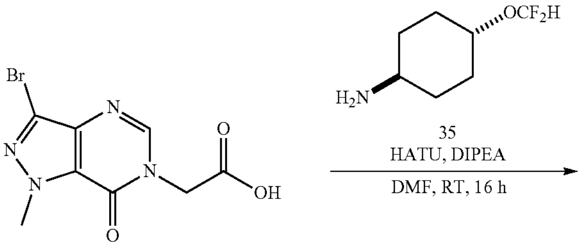

53

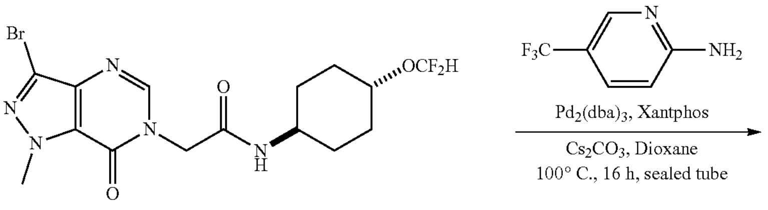

54

-continued

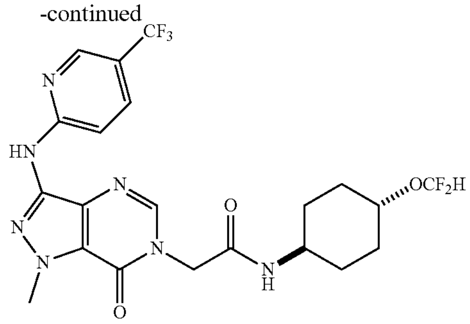

55

To a stirred solution of 2-(3-bromo-1-methyl-7-oxo-1,7-dihydro-6H-pyrazolo[4,3-d]pyrimidin-6-yl)acetic acid (53) (1.2 g, 4.18 mmol) in DMF (15 mL) were added HATU (2.3 g, 6.27 mmol), DIPEA (2.3 mL, 12.54 mmol) at 0° C. and reaction mixture was stirred for 5 min at same temperature. Then added (1r,4r)-4-(difluoromethoxy)cyclohexan-1-amine (35) (827 mg, 5.017 mmol) and the reaction was stirred at RT for 16 h. The reaction mixture was quenched with ice cold water. The precipitated solid was filtered and washed with $Et_2O$ to afford N2-(3-bromo-1-methyl-7-oxo-1,7-dihydro-6H-pyrazolo[4,3-d]pyrimidin-6-yl)-N-((1r,4r)-4-(difluoromethoxy)cyclohexyl)acetamide (54) (1.0 g, 55%) as pale yellow solid. MS (ESI) m/z 434.27 $[M+H]^+$; $^1H$ NMR (400 MHz, DMSO-$d_6$): δ 8.23 (d, J=7.6 Hz, 1H), 8.15 (s, 1H), 6.69 (t, J=76 Hz, 1H), 4.62 (s, 2H), 4.16 (s, 3H), 4.10-4.00 (m, 1H), 3.60-3.50 (m, 1H), 2.00-1.90 (m, 2H), 1.90-1.80 (m, 2H), 1.50-1.40 (m, 2H), 1.40-1.25 (m, 2H).

To a stirred solution of N2-(3-bromo-1-methyl-7-oxo-1,7-dihydro-6H-pyrazolo[4,3-d]pyrimidin-6-yl)-N-((1r,4r)-4-(difluoromethoxy)cyclohexyl)acetamide (54) (400 mg, 0.921 mmol) in 1,4 dioxane (5 mL) were added 5-(trifluoromethyl)pyridin-2-amine (149 mg, 0.921 mmol) and cesium carbonate (898 mg, 2.76 mmol). The reaction was then degassed with argon for 15 min, then added $Pd_2(dba)_3$ (53 mg, 0.09 mmol) and Xantphos (84, 0.09 mmol), the reaction mixture again degassed with argan for 5 min, then the reaction mixture was stirred at 100° C. for 2 h. The reaction mixture was diluted with ice cold water and extracted with EtOAc (2×15 mL). The organic layer was dried over anhydrous $Na_2SO_4$, filtered and concentrated. The residue was purified by silica column to afford N-((1r,4r)-4-(difluoromethoxy)cyclohexyl)-2-(1-methyl-7-oxo-3-((5-(trifluoromethyl)pyridin-2-yl)amino)-1,7-dihydro-6H-pyrazolo[4,3-d]pyrimidin-6-yl)acetamide (55) (90 mg, 19% yield) as white solid. MS (ESI) m/z 516.50 $[M+H]^+$; $^1H$ NMR (400 MHz, DMSO-$d_6$): δ 9.70 (s, 1H), 8.42 (s, 1H), 8.24 (d, J=7.6 Hz, 1H), 8.02 (s, 1H), 7.90 (d, J=6.80 Hz, 1H), 7.18 (d, J=8.80 Hz, 1H), 6.69 (t, J=76 Hz, 1H), 4.62 (s, 2H), 4.18 (s, 3H), 4.10-4.00 (m, 1H), 3.60-3.50 (m, 1H), 2.00-1.90 (m, 2H), 1.90-1.80 (m, 2H), 1.50-1.40 (m, 2H), 1.40-1.25 (m, 2H).

Example 25: Synthesis of N-(3-fluoro-4-methoxyphenyl)-2-(1-methyl-7-oxo-3-((5-(trifluoromethyl)pyridin-2-yl)amino)-1,7-dihydro-6H-pyrazolo[4,3-d]pyrimidin-6-yl)acetamide (64)

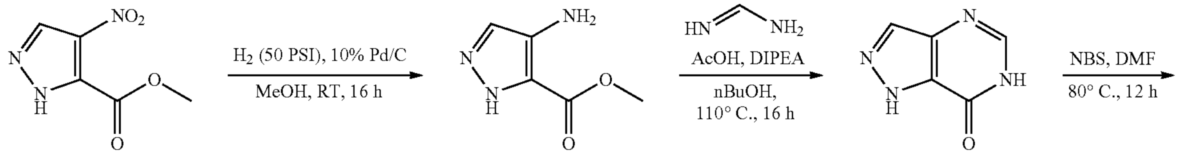

1 56 57

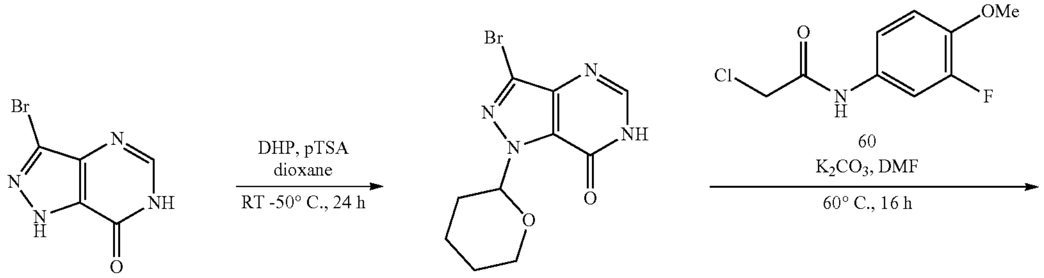

58 59

-continued

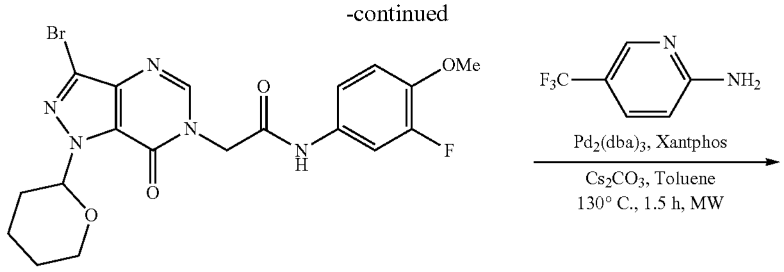

61

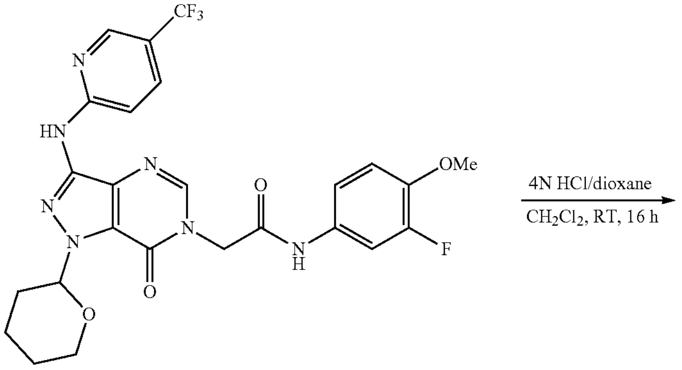

62

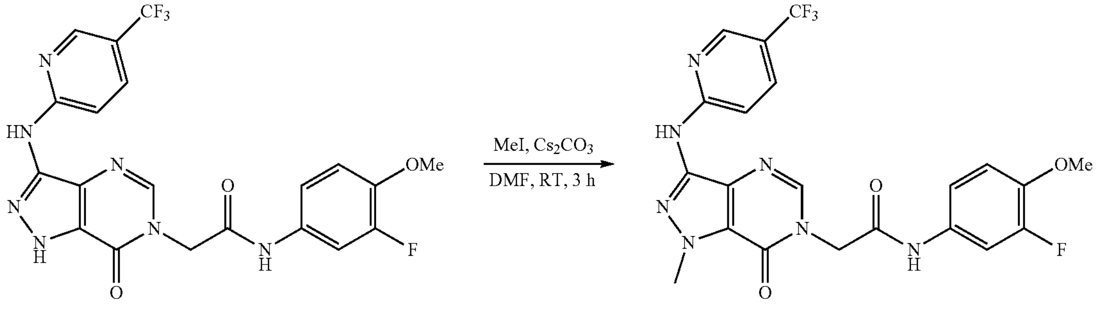

63 64

To a stirred solution of methyl 4-nitro-1H-pyrazole-5-carboxylate (1) (10 g, 58.47 mmol) in MeOH (100 mL) was added 10% Pd/C (3.0 g). The reaction mixture was stirred at RT under hydrogen (50 PSI) atmosphere for 16 h. The reaction mixture was filtered through celite pad and the filtrate was concentrated to obtain methyl 4-amino-1H-pyrazole-5-carboxylate (56) (8 g, 97% yield) as a brown solid. $^1$H NMR (400 MHz, DMSO-$d_6$): δ 12.82 (brs, 1H), 7.09 (s, 1H), 4.87 (s, 2H), 3.77 (s, 3H).

To a stirred solution of methyl 4-amino-1H-pyrazole-5-carboxylate (56) (8 g, 56.73 mmol) in n-butanol (80 mL) were added DIPEA (48.15 ml, 283.8 mmol), formamidine acetate (6.49 g, 62.41 mmol) at RT and then the reaction was stirred at 110° C. for 3 h. The reaction mixture was cooled to RT and precipitated solid was filtered off. The solid compound was triturated with diethyl ether to afford 1,6-dihydro-7H-pyrazolo[4,3-d] pyrimidin-7-one (57) (7.1 g, 92%) as an off-white solid. MS (ESI) m/z 137.05 $[M+H]^+$; $^1$H NMR (400 MHz, DMSO-$d_6$): δ 13.10 (brs, 2H), 8.11 (s, 1H), 7.85 (s, 1H).

To a stirred solution of methyl 1,6-dihydro-7H-pyrazolo [4,3-d]pyrimidin-7-one (57) (5 g, 3.67 mmol) in DMF (80 mL) was added NBS (10 g, 5.51 mmol) at rt and the reaction mixture was stirred at 60° C. for 12 h. The reaction mixture was cooled to RT, quenched with cold water and precipitated solid was filtered off. The solid was dried under vacuum to afford 3-bromo-1,6-dihydro-7H-pyrazolo[4,3-d]pyrimidin-7-one (58) (5.5 g, 64%) as an off-white solid. MS (ESI) m/z 216.97 $[M+2]^+$.

To a stirred solution of 3-bromo-1,6-dihydro-7H-pyrazolo [4,3-d]pyrimidin-7-one (58) (3 g, 14.31 mmol) in DMF (30 mL) were added pTSA (134 mg, 0.7 mmol) followed by DHP (6.05 g, 70.42 mmol) at rt and the reaction mixture was stirred at 60° C. for 16 h. The reaction mixture was cooled to rt, quenched with cold water and extracted with EtOAc (3×50 mL). The organic layer was dried over anhydrous $Na_2SO_4$, filtered and concentrated. The residue was purified by flash column chromatography to afford 3-bromo-1-(tetrahydro-2H-pyran-2-yl)-1,6-dihydro-7H-pyrazolo[4,3-d] pyrimidin-7-one (59) (2.6 g, 61%) as an off-white solid. MS (ESI) m/z 298.95 $[M+H]^+$; $^1$H NMR (400 MHz, DMSO-$d_6$): δ 8.98 (s, 1H), 6.13 (dd, J=10.4, 2.0 Hz, 1H), 3.93 (d, J=12.8 Hz, 1H), 3.64-3.58 (m, 1H), 2.49-2.24 (m, 1H), 2.02-1.91 (m, 2H), 1.70-1.55 (m, 4H).

To a stirred solution of 3-bromo-1-(tetrahydro-2H-pyran-2-yl)-1,6-dihydro-7H-pyrazolo[4,3-d]pyrimidin-7-one (59) (2.6 g, 8.69 mmol) in DMF (30 mL) were added $K_2CO_3$ (3.6 g, 26.03 mmol) followed by 2-chloro-N-(3-fluoro-4-methoxyphenyl)acetamide (60) (2.83 g, 13.04 mmol) at RT and reaction mixture was stirred at 60° C. for 16 h. The reaction mixture was quenched with water (100 mL) and extracted with EtOAc (2×250 mL). The organic layer was dried over anhydrous $Na_2SO_4$, filtered and concentrated. The residue was purified by flash column chromatography over 100-200 silica using 70% EtOAc in hexanes as an eluent to afford 2-(3-bromo-7-oxo-1-(tetrahydro-2H-pyran-2-yl)-1,7-dihydro-6H-pyrazolo [4,3-d]pyrimidin-6-yl)-N-(3-fluoro-4-methoxyphenyl)acetamide (61) (1.5 g, 30% yield) as an off-white solid. MS (ESI) m/z 482.01 $[M+H]^+$; $^1H$ NMR (400 MHz, DMSO-$d_6$): δ 8.31 (s, 1H), 7.53 (dd, J=13.6, 2.4 Hz, 1H), 7.27-7.20 (m, 1H), 7.14 (t, J=9.8 Hz, 1H), 6.11 (dd, J=10.4, 2.0 Hz, 1H), 4.88 (s, 2H), 4.0-3.90 (m, 1H), 3.80 (s, 3H), 3.62-3.56 (m, 1H), 2.32-2.24 (m, 1H), 2.01-1.92 (m, 2H), 1.70-1.50 (m, 3H).

To a degassed (argon) solution of 2-(3-bromo-7-oxo-1-(tetrahydro-2H-pyran-2-yl)-1,7-dihydro-6H-pyrazolo [4,3-d]pyrimidin-6-yl)-N-(3-fluoro-4-methoxyphenyl)acetamide (61) (200 mg, 0.417 mmol) in toluene (6 mL) were added $Cs_2CO_3$ (406 mg, 1.25 mmol), $Pd_2(dba)_3$ (38 mg, 0.04 mmol), Xantphos (24 mg, 0.041 mmol) and 5-(trifluoromethyl)pyridin-2-amine (101 mg, 0.626 mmol) at RT. The solution was degassed again for 15 min and the mixture was heated at 130° C. in microwave for 1.5 h. Reaction mixture was cooled to room temperature and filtered through a celite pad. The celite pad was washed with 5% MeOH in $CH_2Cl_2$. The filtrate was concentrated under reduced pressure to afford the crude, which was purified by prep-HPLC to afford N-(3-fluoro-4-methoxyphenyl)-2-(7-oxo-1-(tetrahydro-2H-pyran-2-yl)-3-((5-(trifluoromethyl)pyridin-2-yl)amino)-1,7-dihydro-6H-pyrazolo[4,3-d]pyrimidin-6-yl) acetamide (62) (50 mg, 24%) as a pale yellow solid. MS (ESI) m/z 562.14 $[M+H]^+$; $^1H$ NMR (400 MHz, DMSO-$d_6$): δ 10.56 (brs, 1H), 9.80 (brs, 1H), 8.45 (s, 1H), 8.19 (s, 1H), 7.95 (dd, J=8.8, 2.4 Hz, 1H), 7.55 (dd, J=13.2, 2 Hz, 1H), 7.26 (d, J=8.8 Hz, 2H), 7.15 (t, J=9.2 Hz, 1H), 6.12 (dd, J=8, 2 Hz, 1H), 4.87 (s, 2H), 3.95 (d, J=7.6 Hz, 1H), 3.80 (s, 3H), 3.63-3.56 (m, 1H), 2.39-2.31 (m, 1H), 2.03-1.93 (m, 2H), 1.72-1.56 (m, 1H), 1.55-1.53 (m, 2H).

To a stirred solution of N-(3-fluoro-4-methoxyphenyl)-2-(7-oxo-1-(tetrahydro-2H-pyran-2-yl)-3-((5-(trifluoromethyl)pyridin-2-yl)amino)-1,7-dihydro-6H-pyrazolo[4,3-d]pyrimidin-6-yl)acetamide (62) (45 mg, 0.08 mmol) in DCM (2 mL) was added 4N HCl/dioxane (2 ml) at 0° C. The reaction mixture was stirred at RT for 16 h. The reaction mixture was concentrated and the residue was purified by prep HPLC to afford N-(3-fluoro-4-methoxyphenyl)-2-(7-oxo-3-((5-(trifluoromethyl)pyridin-2-yl)amino)-1,7-dihydro-6H-pyrazolo[4,3-d]pyrimidin-6-yl)acetamide (63) (12 mg, 31% yield) as an off-white solid. MS (ESI) m/z 478.05 $[M+H]^+$; $^1H$ NMR (400 MHz, DMSO-$d_6$): δ 13.92 (brs, 1H), 10.49 (s, 1H), 9.77 (brs, 1H), 8.44 (s, 1H), 8.09 (s, 1H), 7.90 (d, J=8.8 Hz, 1H), 7.55 (dd, J=13.2, 2 Hz, 1H), 7.26 (d, J=9.2 Hz, 1H), 7.21-7.12 (m, 2H), 4.86 (s, 2H), 3.80 (s, 3H).

To a stirred solution of N-(3-fluoro-4-methoxyphenyl)-2-(7-oxo-3-((5-(trifluoromethyl)pyridin-2-yl)amino)-1,7-dihydro-6H-pyrazolo[4,3-d]pyrimidin-6-yl)acetamide (63) (50 mg, 0.104 mmol) in DMF (2 mL) were added $Cs_2CO_3$ (68 mg, 0.209 mmol) followed by methyl iodide (18 mg, 0.125 mmol) at RT. The reaction mixture was stirred for 16 h at same temperature. The reaction mixture was quenched with water (50 ml) and extracted with EtOAc (2*25 mL). The combined organic layer was dried over anhydrous $Na_2SO_4$, filtered and concentrated. The residue was purified by prep-HPLC to afford N-(3-fluoro-4-methoxyphenyl)-2-(1-methyl-7-oxo-3-((5-(trifluoromethyl) pyridin-2-yl) amino)-1,7-dihydro-6H-pyrazolo[4,3-d]pyrimidin-6-yl)acetamide (64) (10 mg, 14%) as a white solid. MS (ESI) m/z 492.09 $[M+H]^+$; $^1H$ NMR (400 MHz, DMSO-$d_6$): δ 10.60 (s, 1H), 9.68 (s, 1H), 8.50 (brs, 2H), 8.43 (s, 1H), 8.10 (s, 1H), 7.90 (d, J=8.8 Hz, 1H), 7.55 (d, J=13.6 Hz, 1H), 7.27 (d, J=8.8 Hz, 1H), 7.19-7.12 (m, 2H), 4.85 (s, 2H), 4.15 (s, 3H), 3.80 (s, 3H).

Example 26: Synthesis of N-((1r,4r)-4-(difluoromethoxy)cyclohexyl)-2-(1-methyl-7-oxo-3-((6-(trifluoromethyl)pyridin-3-yl)amino)-1,7-dihydro-6H-pyrazolo[4,3-d]pyrimidin-6-yl)acetamide (65)

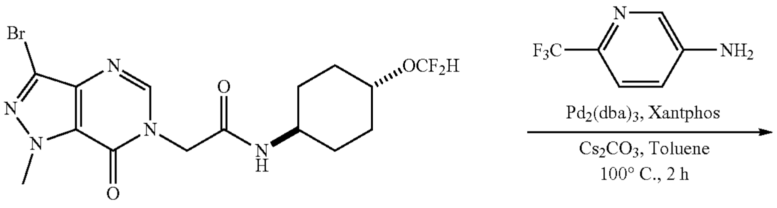

54

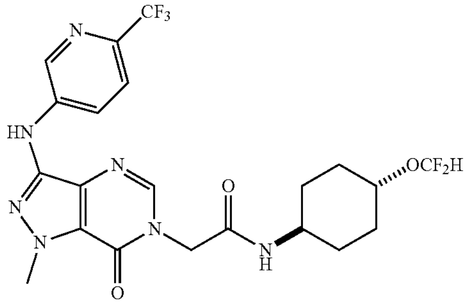

65

To a stirred solution of 2-(3-bromo-1-methyl-7-oxo-1,7-dihydro-6H-pyrazolo[4,3-d]pyrimidin-6-yl)-N-((1r,4r)-4-(difluoromethoxy)cyclohexyl)acetamide (54) (300 mg, 0.69 mmol) in 1,4 dioxane (5 mL) were added 6-(trifluoromethyl) pyridin-3-amine (111 mg, 0.69 mmol) and cesium carbonate (673 mg, 2.07 mmol). The reaction was degassed with argon for 15 min, then added $Pd_2(dba)_3$ (63 mg, 0.06 mmol) and Xantphos (39 mg, 0.06 mmol), the reaction mixture again degassed with argon for 5 min, then the reaction mixture was stirred at 100° C. for 2 h. The reaction mixture was diluted with ice cold water and extracted with EtOAc (2×15 mL). The combined organic layer was dried over anhydrous $Na_2SO_4$, filtered and concentrated to obtain crude was purified by SFC to afford N-((1r,4r)-4-(difluoromethoxy) cyclohexyl)-2-(1-methyl-7-oxo-3-((6-(trifluoromethyl)pyridin-3-yl)amino)-1,7-dihydro-6H-pyrazolo[4,3-d]pyrimidin-6-yl)acetamide (65) (100 mg, 28% yield) as a pale brown solid.

MS (ESI) m/z 516.50 $[M+H]^+$; $^1H$ NMR (400 MHz, DMSO-$d_6$): δ 9.80 (s, 1H), 8.89 (s, 1H), 8.30-8.20 (m, 2H), 8.10 (s, 1H), 7.76 (d, J=8.80 Hz, 1H), 6.69 (t, J=76 Hz, 1H), 4.64 (s, 2H), 4.30 (s, 3H), 4.10-4.00 (m, 1H), 3.65-3.50 (m, 1H), 2.00-1.90 (m, 2H), 1.90-1.80 (m, 2H), 1.50-1.40 (m, 2H), 1.40-1.25 (m, 2H).

Example 27: Synthesis of N-((1r,4r)-4-(2-hydroxy-2-methylpropoxy)cyclohexyl)-2-(1-methyl-7-oxo-3-((6-(trifluoromethyl)pyridin-3-yl)amino)-1,7-dihydro-6H-pyrazolo[4,3-d]pyrimidin-6-yl)acetamide (68)

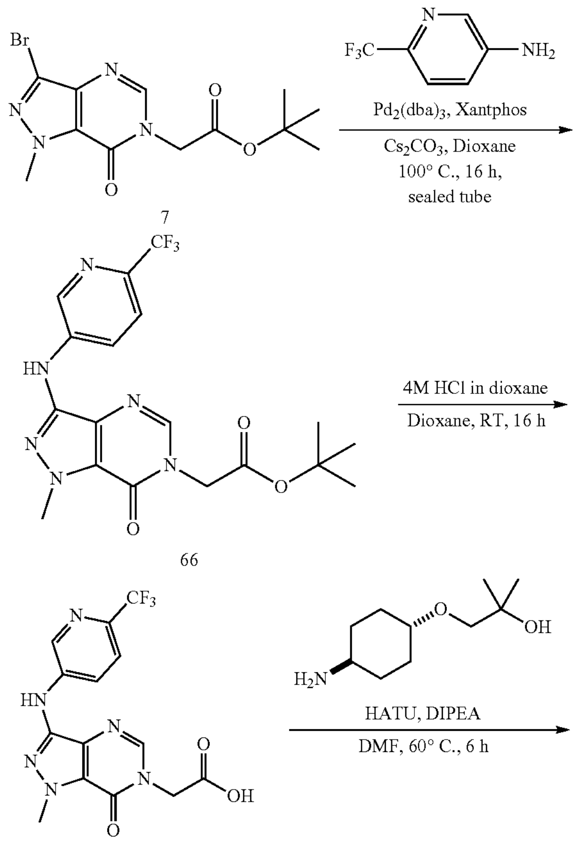

7

66

67

-continued

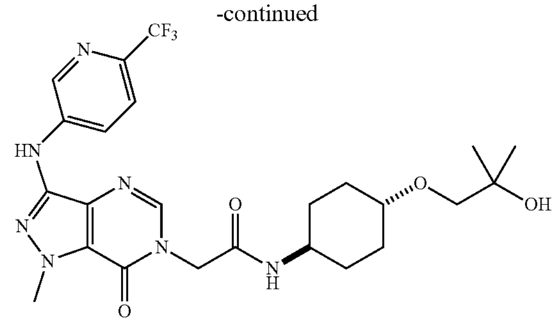

68

To a stirred solution of tert-butyl 2-(3-bromo-1-methyl-7-oxo-1,7-dihydro-6H-pyrazolo[4,3-d]pyrimidin-6-yl)acetate (7) (500 mg, 1.46 mmol) in 1,4 dioxane (15 mL) were added 6-(trifluoromethyl)pyridin-3-amine (284 mg, 1.75 mmol) and cesium carbonate (1.42 g, 4.38 mmol). The reaction was degassed with argon for 15 min, then added $Pd_2(dba)_3$ (133 mg, 0.14 mmol) and Xantphos (84 mg, 0.14 mmol). The reaction mixture was again degassed with argon for 5 min, then reaction mixture was stirred at 100° C. for 16 h. The reaction mixture was diluted with ice cold water and extracted with EtOAc (2×15 mL). The combined organic layer was dried over anhydrous $Na_2SO_4$, filtered and concentrated. The residue was purified by silica column to afford tert-butyl 2-(1-methyl-7-oxo-3-((6-(trifluoromethyl) pyridin-3-yl)amino)-1,7-dihydro-6H-pyrazolo[4,3-d]pyrimidin-6-yl)acetate (66) (600 mg, 70% yield) as a pale yellow solid. MS (ESI) m/z 425.4 $[M+H]^+$.

To a stirred solution of tert-butyl 2-(1-methyl-7-oxo-3-((6-(trifluoromethyl)pyridin-3-yl)amino)-1,7-dihydro-6H-pyrazolo[4,3-d]pyrimidin-6-yl)acetate (66) (600 mg, 1.45 mmol) in 1,4-dioxane (2 mL) was added 4M HCl in dioxane (10 mL) at 0° C. The reaction mixture was stirred at RT for 16 h. The reaction mixture was evaporated to give 2-(1-methyl-7-oxo-3-((6-(trifluoromethyl)pyridin-3-yl)amino)-1,7-dihydro-6H-pyrazolo[4,3-d]pyrimidin-6-yl)acetic acid (67) (500 mg, 90% yield) as a pale yellow solid. MS (ESI) m/z 369.33 $[M+H]^+$.

To a stirred solution of 2-(1-methyl-7-oxo-3-((6-(trifluoromethyl)pyridin-3-yl)amino)-1,7-dihydro-6H-pyrazolo[4,3-d]pyrimidin-6-yl)acetic acid (67) (300 mg, 0.81 mmol) in DMF (10 mL) was added HATU (464 mg, 1.22 mmol), DIPEA (0.31 mL, 2.44 mmol) at 0° C. The reaction mixture was stirred for 5 min at same temperature. Added 1-(((1r,4r)-4-aminocyclohexyl)oxy)-2-methylpropan-2-ol (182 mg, 0.97 mmol) and the reaction was stirred at RT for 16 h. The reaction mixture was diluted with water and extracted with ethyl acetate (2×50 mL). The combined organic layer was evaporated and the residue was purified by Prep HPLC to afford N-((1r,4r)-4-(2-hydroxy-2-methylpropoxy)cyclohexyl)-2-(1-methyl-7-oxo-3-((6-(trifluoromethyl)pyridin-3-yl)amino)-1,7-dihydro-6H-pyrazolo[4,3-d]pyrimidin-6-yl) acetamide (68) (120 mg, 27% yield) as an off-white solid. MS (ESI) m/z 538.15 $[M+H]^+$; $^1H$ NMR (400 MHz, DMSO-$d_6$): δ 9.80 (s, 1H), 8.89 (s, 1H), 8.21 (d, J=7.2 Hz, 2H), 8.09 (s, 1H), 7.76 (d, J=8.80 Hz, 1H), 4.63 (s, 2H), 4.20 (s, 1H), 4.13 (s, 3H), 3.60-3.50 (m, 1H), 3.30-3.20 (m, 1H), 3.15 (s, 2H), 2.00-1.90 (m, 2H), 1.90-1.80 (m, 2H), 1.30-1.20 (m, 4H), 1.05 (s, 6H).

Example 28: Synthesis of N-(3-fluoro-4-methoxyphenyl)-2-(7-oxo-1-(tetrahydro-2H-pyran-2-yl)-3-((5-(trifluoromethyl)pyridin-2-yl)amino)-1,7-dihydro-6H-pyrazolo[4,3-d]pyrimidin-6-yl)acetamide (70)

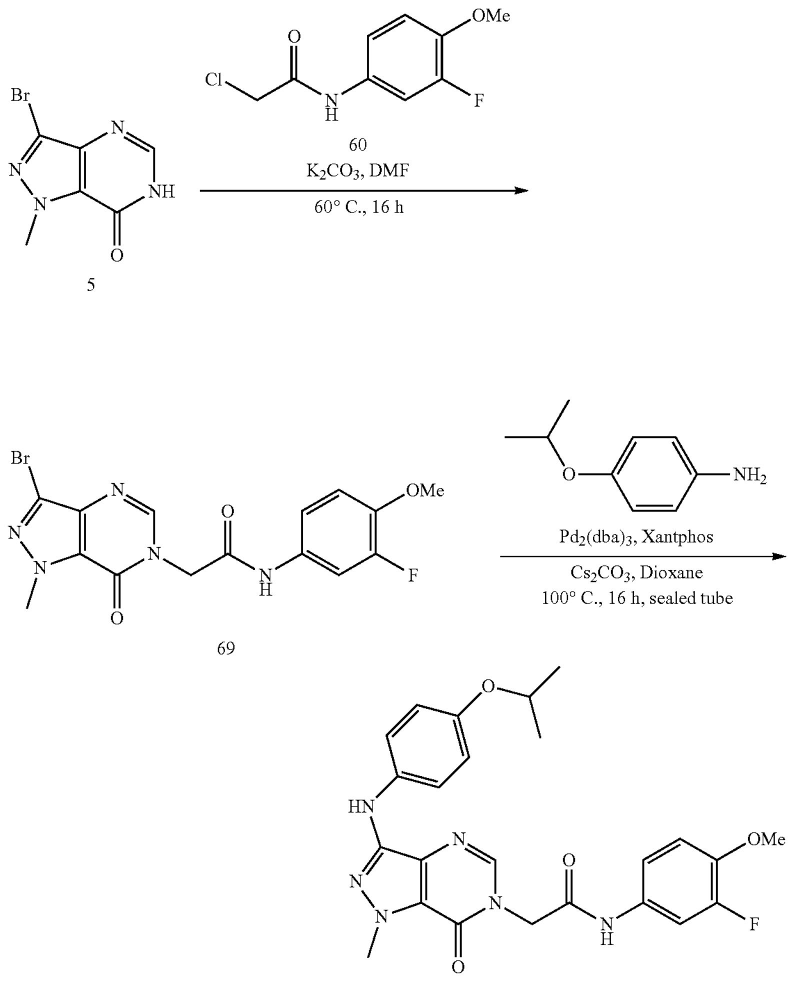

70

To a stirred solution of 3-bromo-1-methyl-1,6-dihydro-7H-pyrazolo[4,3-d]pyrimidin-7-one (5) (2 g, 8.70 mmol) in DMF (30 mL) were added $K_2CO_3$ (3.6 g, 26.03 mmol) followed by 2-chloro-N-(3-fluoro-4-methoxyphenyl)acetamide (60) (2.83 g, 13.04 mmol) at RT. The reaction mixture was stirred at 60° C. for 16 h. The reaction mixture was quenched with water (100 mL) and extracted with EtOAc (2×250 mL). The combined organic layer was dried over anhydrous $Na_2SO_4$, filtered and concentrated. The residue was purified by flash column chromatography to afford 2-(3-bromo-1-methyl-7-oxo-1,7-dihydro-6H-pyrazolo[4,3-d]pyrimidin-6-yl)-N-(3-fluoro-4-methoxyphenyl)acetamide (69) (2.91 g, 81% yield) as a pale yellow solid. MS (ESI) m/z 412.20 $[M+H]^+$; $^1H$ NMR (400 MHz, DMSO-$d_6$): δ 10.49 (brs, 1H), 8.31 (s, 1H), 7.53 (dd, J=9.6, 2.4 Hz, 1H), 7.25 (1H, J=10.0 Hz, 1H), 7.13 (t, J=9.2 Hz, 1H), 4.85 (s, 2H), 4.17 (s, 3H), 3.80 (s, 3H).

To a degassed (argon) solution of 2-(3-bromo-1-methyl-7-oxo-1,7-dihydro-6H-pyrazolo[4,3-d]pyrimidin-6-yl)-N-(3-fluoro-4-methoxyphenyl)acetamide (69) (343 mg, 0.82 mmol) in dioxane (10 mL) were added $Cs_2CO_3$ (812 mg, 2.50 mmol), $Pd_2(dba)_3$ (76 mg, 0.08 mmol), Xantphos (48 mg, 0.082 mmol) and 4-isopropoxyaniline (186 mg, 1.34 mmol) at RT. The reaction mixture was degassed again for 15 min and the mixture heated at 100° C. for 16 h. The reaction mixture was cooled to room temperature and filtered through a celite pad. The celite pad was washed with 5% MeOH in $CH_2Cl_2$. The filtrate was concentrated under reduced pressure. The residue was purified by prep-HPLC to afford N-(3-fluoro-4-methoxyphenyl)-2-(3-((4-isopropoxyphenyl)amino)-1-methyl-7-oxo-1,7-dihydro-6H-pyrazolo[4,3-d]pyrimidin-6-yl)acetamide (70) (30 mg, 8%) as an off-white solid. MS (ESI) m/z 481.50 $[M+H]^+$; $^1H$ NMR (400 MHz, DMSO-$d_6$): δ 10.47 (s, 1H), 8.66 (s, 1H), 8.10 (s, 1H), 7.58-7.53 (m, 4H), 7.27 (d, J=8.8 Hz, 1H), 7.14 (t, J=9.2 Hz, 1H), 6.82 (d, J=8.8 Hz, 2H), 4.85 (s, 2H), 4.48-4.44 (m, 1H), 4.07 (s, 3H), 3.80 (s, 3H), 1.23 (d, J=6.0 Hz, 6H).

Example 29: Synthesis of 2-(3-((4-chlorophenyl) amino)-1-methyl-7-oxo-1,7-dihydro-6H-pyrazolo[4, 3-d]pyrimidin-6-yl)-N-(3-fluoro-4-methoxyphenyl) acetamide (71)

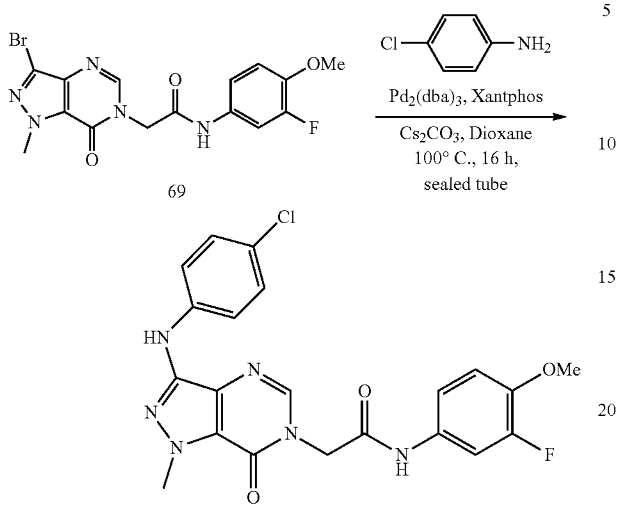

69

71

To a degassed (argon) solution of 2-(3-bromo-1-methyl-7-oxo-1,7-dihydro-6H-pyrazolo[4,3-d]pyrimidin-6-yl)-N-(3-fluoro-4-methoxyphenyl)acetamide (69) (343 mg, 0.82 mmol) in dioxane (10 mL) were added $Cs_2CO_3$ (812 mg, 2.5 mmol), $Pd_2(dba)_3$ (76 mg, 0.08 mmol), Xantphos (48 mg, 0.082 mmol) and 4-chloroaniline (160 mg, 1.34 mmol) at RT. The reaction mixture was degassed again for 15 min and the mixture was heated at 100° C. for 16 h. The reaction mixture was cooled to room temperature and filtered through celite pad. The celite pad was washed with 5% MeOH in $CH_2Cl_2$. The filtrate was concentrated under reduced pressure. The residue was purified by prep-HPLC to afford 2-(3-((4-chlorophenyl)amino)-1-methyl-7-oxo-1,7-dihydro-6H-pyrazolo [4,3-d]pyrimidin-6-yl)-N-(3-fluoro-4-methoxyphenyl)acetamide (71) (50 mg, 13%) as an off-white solid. MS (ESI) m/z 455.26 $[M-H]^-$; $^1H$ NMR (400 MHz, DMSO-$d_6$): δ 10.47 (s, 1H), 9.12 (s, 1H), 8.13 (s, 1H), 7.64 (dd, J=9.2, 2.4 Hz, 2H), 7.54 (dd, J=13.6, 2.4 Hz, 1H), 7.28 (d, J=9.2 Hz, 3H), 7.14 (t, J=9.2 Hz, 1H), 4.85 (s, 2H), 4.10 (s, 3H), 3.80 (s, 3H).

Example 30: Synthesis of 2-(1-ethyl-7-oxo-3-((4-(trifluoromethyl)phenyl)amino)-1,7-dihydro-6H-pyrazolo[4,3-d]pyrimidin-6-yl)-N-(3-fluoro-4-methoxyphenyl)acetamide (77)

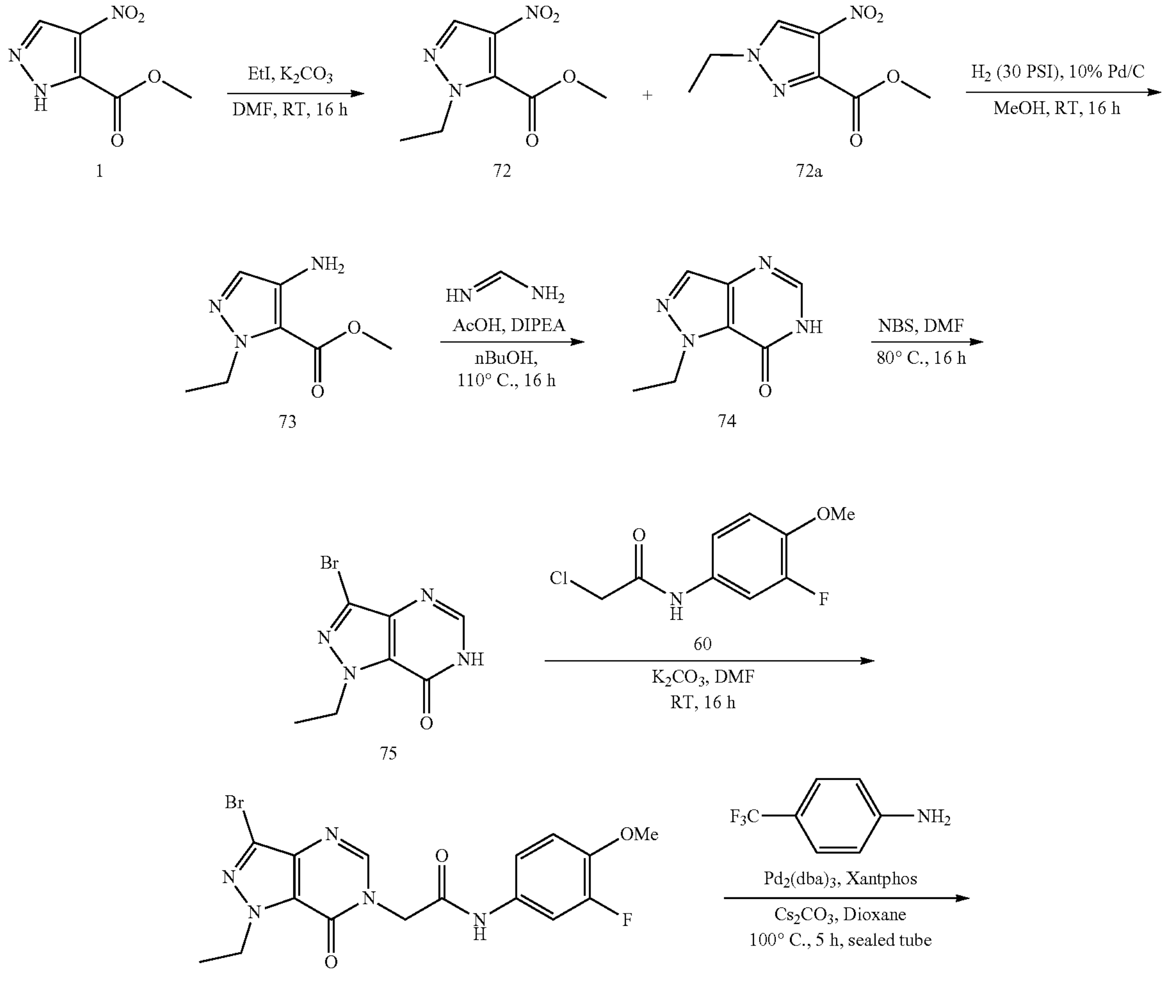

1

72

72a

73

74

75

60

76

-continued

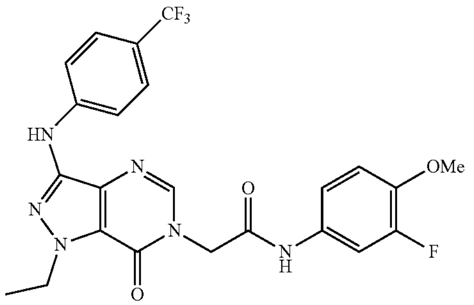

77

To a stirred solution of methyl 4-nitro-1H-pyrazole-5-carboxylate (1) (5.0 g, 29.22 mmol) in DMF (50 mL) were added $K_2CO_3$ (12.07 g, 87.66 mmol) followed by ethyl iodide (2.58 mL, 32.14 mmol) at RT. The reaction mixture was stirred for 16 h at same temperature. The reaction mixture was quenched with water (100 mL) and extracted with EtOAc (2×100 mL). The combined organic layer was dried over anhydrous $Na_2SO_4$, filtered and concentrated. The residue was purified through silica gel column to afford methyl 1-ethyl-4-nitro-1H-pyrazole-5-carboxylate (72) (1.7 g, 29%). MS (ESI) m/z 200.07 $[M+H]^+$. $^1$H NMR (400 MHz, DMSO-$d_6$): δ 8.39 (s, 1H), 4.75-4.70 (m, 1H), 4.29 (q, J=7.2 Hz, 2H), 3.99 (s, 3H), 1.38 (d, J=7.2 Hz, 3H).

To a stirred solution of methyl 1-ethyl-4-nitro-1H-pyrazole-5-carboxylate (72) (1.8 g, 9.04 mmol) in MeOH (100 mL) was added 10% Pd/C (3.0 g). The reaction mixture was stirred at RT under hydrogen (50 PSI) atmosphere for 8 h. The reaction mixture was filtered through a celite pad and the filtrate was concentrated to obtain methyl 4-amino-1-ethyl-1H-pyrazole-5-carboxylate (73) (1.5 g, 98% yield) as a brown solid. MS (ESI) m/z 170.2 $[M+H]^+$; $^1$H NMR (400 MHz, DMSO-$d_6$): δ 7.02 (s, 1H), 5.00 (brs, 2H), 4.31 (q, J=7.2 Hz, 2H), 3.80 (s, 3H), 1.20 (d, J=7.2 Hz, 3H).

To a stirred solution of ethyl 4-amino-1H-pyrazole-5-carboxylate (73) (1.8 g, 10.64 mmol) in n-butanol (80 mL) were added DIPEA (9.2 mL, 53.2 mmol), formamidine acetate (1.21 g, 11.70 mmol) at RT. The reaction mixture was stirred at 110° C. for 3 h. The reaction mixture was cooled to RT and precipitated solid was filtered off. The solid compound was triturated with diethyl ether to afford 1-ethyl-1,6-dihydro-7H-pyrazolo[4,3-d]pyrimidin-7-one (74) (1.2 g, 69%) as an off-white solid. MS (ESI) m/z 165.11 $[M+H]^+$; $^1$H NMR (400 MHz, DMSO-$d_6$): δ 7.97 (s, 1H), 7.79 (s, 1H), 4.57 (q, J=7.2 Hz, 2H), 1.38 (d, J=7.2 Hz, 3H).

To a stirred solution of ethyl 1,6-dihydro-7H-pyrazolo[4,3-d]pyrimidin-7-one (74) (1.2 g, 7.31 mmol) in DMF (80 mL) was added NBS (2.86 g, 16.08 mmol) at RT. The reaction mixture was stirred at 80° C. for 12 h. The reaction mixture was cooled to RT, quenched with cold water and precipitated solid was filtered off. The solid was dried under vacuum to afford 3-bromo-1-ethyl-1,6-dihydro-7H-pyrazolo[4,3-d]pyrimidin-7-one (75) (1.0 g, 56%) as off-white solid. MS (ESI) m/z 243.08 $[M+2]^+$; $^1$H NMR (400 MHz, DMSO-$d_6$): δ 12.51 (s, 1H), 7.93 (s, 1H), 4.55 (q, J=7.2 Hz, 2H), 1.39 (d, J=7.2 Hz, 3H).

To a stirred solution of 3-bromo-1-ethyl-1,6-dihydro-7H-pyrazolo[4,3-d]pyrimidin-7-one (75) (500 mg, 2.06 mmol) in DMF (30 mL) were added $K_2CO_3$ (854 mg, 6.18 mmol) followed by 2-chloro-N-(3-fluoro-4-methoxyphenyl)acetamide (60) (537.9 mg, 2.47 mmol) at RT. The reaction mixture was stirred at 60° C. for 16 h. The reaction mixture was quenched with water (100 mL) and extracted with EtOAc (2×250 mL). The combined organic layer was dried over anhydrous $Na_2SO_4$, filtered and concentrated. The residue was purified by flash column chromatography over 100-200 silica to afford 2-(3-bromo-1-ethyl-7-oxo-1,7-dihydro-6H-pyrazolo[4,3-d]pyrimidin-6-yl)-N-(3-fluoro-4-methoxyphenyl)acetamide (76) (400 mg, 46% yield) as an off-white solid. MS (ESI) m/z 424.29 $[M+H]^+$; $^1$H NMR (400 MHz, DMSO-$d_6$): δ 8.24 (s, 1H), 7.53 (d, J=10.8 Hz, 1H), 7.26 (d, J=4.4 Hz, 1H), 7.13 (d, J=8.0 Hz, 1H), 4.86 (s, 2H), 4.56 (q, J=7.2 Hz, 2H), 3.80 (s, 3H), 1.39 (d, J=7.2 Hz, 3H).

To a degassed (argon) solution of 2-(3-bromo-1-ethyl-7-oxo-1,7-dihydro-6H-pyrazolo[4,3-d]pyrimidin-6-yl)-N-(3-fluoro-4-methoxyphenyl)acetamide (76) (330 mg, 0.777 mmol) in dioxane (6 mL) were added $Cs_2CO_3$ (406 mg, 1.25 mmol), $Pd_2(dba)_3$ (70.5 mg, 0.077 mmol), Xantphos (44.5 mg, 0.077 mmol) and 5-(trifluoromethyl)pyridin-2-amine (188 mg, 1.165 mmol) at RT. The solution was degassed again for 15 min and the mixture was heated at 100° C. in a microwave for 3 h. The reaction mixture was cooled to room temperature and filtered through a celite pad. The celite pad was washed with 5% MeOH in $CH_2Cl_2$. The filtrate was concentrated under reduced pressure to afford the crude, which was purified by prep-HPLC to afford 2-(1-ethyl-7-oxo-3-((4-(trifluoromethyl)phenyl)amino)-1,7-dihydro-6H-pyrazolo[4,3-d]pyrimidin-6-yl)-N-(3-fluoro-4-methoxyphenyl)acetamide (77) (103 mg, 26%) as a pale yellow solid. MS (ESI) m/z 505.31 $[M+H]^+$; $^1$H NMR (400 MHz, DMSO-$d_6$): δ 10.47 (s, 1H), 9.44 (s, 1H), 8.16 (s, 1H), 7.72 (d, J=8.8 Hz, 2H), 7.57 (d, J=8.8 Hz, 2H), 7.53 (s, 1H), 7.27 (d, J=8.8 Hz, 1H), 7.14 (t, J=9.2 Hz, 1H), 4.81 (s, 2H), 4.52 (q, J=7.2 Hz, 2H), 3.80 (s, 3H), 1.39 (t, J=7.2 Hz, 3H).

Example 31: Synthesis of N-((1r,4r)-4-(difluoromethoxy)cyclohexyl)-2-(1-ethyl-7-oxo-3-((4-(trifluoromethyl)phenyl)amino)-1,7-dihydro-6H-pyrazolo[4,3-d]pyrimidin-6-yl)acetamide (80)

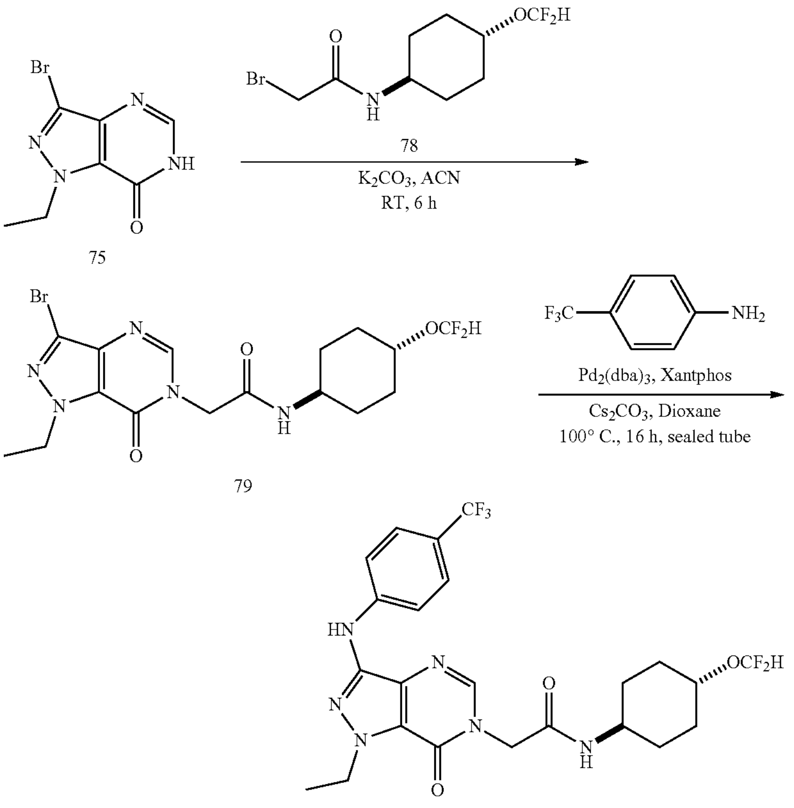

80

To a stirred solution of 3-bromo-1-ethyl-1,6-dihydro-7H-pyrazolo[4,3-d]pyrimidin-7-one (75) (600 mg, 2.46 mmol), 2-bromo-N-((1r,4r)-4-(difluoromethoxy)cyclohexyl)acetamide (78) (642 mg, 2.96 mmol) in DMF (20 mL) were added $K_2CO_3$ (509 mg, 3.66 mmol) and stirred at RT for 16 h. The reaction mixture was diluted with water (10 mL) to give a solid, which was filtered and washed with water to afford 2-(3-bromo-1-ethyl-7-oxo-1,7-dihydro-6H-pyrazolo[4,3-d]pyrimidin-6-yl)-N-((1r,4r)-4-(difluoromethoxy)cyclohexyl)acetamide (79) (300 mg, 27%) as a white solid. MS (ESI) m/z 448.48 $[M+H]^+$; $^1H$ NMR (400 MHz, DMSO-$d_6$): δ 8.26 (d, J=7.6 Hz, 1H), 8.15 (s, 1H), 6.68 (t, J=76.4 Hz, 1H), 4.63 (s, 2H), 4.50 (q, J=7.6 Hz, 2H), 4.10-4.00 (m, 1H), 3.60-3.50 (m, 2H), 2.00-1.90 (m, 2H), 1.90-1.80 (m, 2H), 1.60-1.20 (s, 7H).

To a stirred solution of 2-(3-bromo-1-ethyl-7-oxo-1,7-dihydro-6H-pyrazolo[4,3-d]pyrimidin-6-yl)-N-((1r,4r)-4-(difluoromethoxy)cyclohexyl)acetamide (79) (500 mg, 1.12 mmol) in 1,4 dioxane (5 mL) were added 4-(trifluoromethyl) aniline (216 mg, 1.34 mmol) and cesium carbonate (1.1 g, 3.45 mmol). The reaction mixture was degassed with argon for 15 min, then added $Pd_2(dba)_3$ (103 mg, 0.11 mmol) and Xantphos (63 mg, 0.11 mmol). The reaction mixture was again degassed with argon for 5 min, and then the reaction mixture was stirred at 100° C. for 16 h. The reaction mixture was diluted with ice cold water and extracted with EtOAc (2×15 mL) The combined organic layer was dried over anhydrous $Na_2SO_4$, filtered and concentrated to obtain crude was purified by silica column to afford N-((1r,4r)-4-(difluoromethoxy)cyclohexyl)-2-(1-ethyl-7-oxo-3-((4-(trifluoromethyl)phenyl)amino)-1,7-dihydro-6H-pyrazolo[4,3-d]pyrimidin-6-yl)acetamide (80) (120 mg, 20% yield) as a white solid. MS (ESI) m/z 529.56 $[M+H]^+$; $^1H$ NMR (400 MHz, DMSO-$d_6$): δ 9.44 (s, 1H), 8.23 (d, J=7.6 Hz, 1H), 8.08 (s, 1H), 7.71 (d, J=8.4 Hz, 2H), 7.56 (d, J=8.4 Hz, 2H), 6.69 (t, J=76.4 Hz, 1H), 4.64 (s, 2H), 4.50 (q, J=7.6 Hz, 2H), 4.10-4.00 (m, 1H), 3.60-3.50 (m, 1H), 2.00-1.90 (m, 2H), 1.90-1.80 (m, 2H), 1.50-1.30 (s, 7H).

Example 32: Synthesis of 2-(1-ethyl-7-oxo-3-((4-(trifluoromethyl)phenyl)amino)-1,7-dihydro-6H-pyrazolo[4,3-d]pyrimidin-6-yl)-N-((1r,4r)-4-(2-hydroxy-2-methylpropoxy)cyclohexyl)acetamide (84)

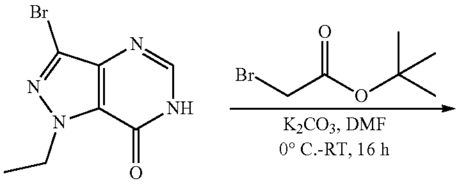

7

-continued

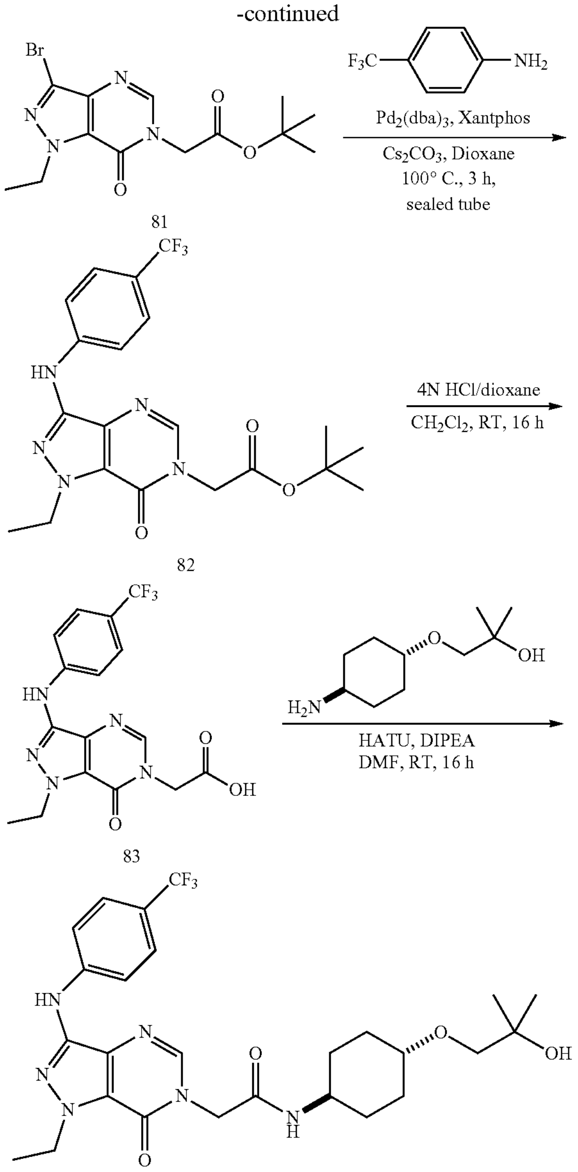

81

82

83

84

To a stirred solution of 3-bromo-1-ethyl-1,6-dihydro-7H-pyrazolo[4,3-d]pyrimidin-7-one (75) (1.9 g, 7.81 mmol) in DMF (100 mL) were added $K_2CO_3$ (2.1 g, 15.6 mmol) followed by tert-butyl bromoacetate (1.4 mL, 9.38 mmol). The reaction mixture was stirred at RT for 16 h. The reaction mixture was quenched with water (100 mL) and extracted with EtOAc (2×250 mL). The combined organic layer was dried over anhydrous $Na_2SO_4$, filtered and concentrated. The residue was purified by flash column chromatography over silica (100-200) to afford tert-butyl 2-(3-bromo-1-ethyl-7-oxo-1,7-dihydro-6H-pyrazolo[4,3-d]pyrimidin-6-yl)acetate (81) (2.3 g, 82% yield) as an off-white solid. MS (ESI) m/z 357.42 $[M+H]^+$; $^1$H NMR (400 MHz, $CDCl_3$): δ 8.24 (s, 1H), 4.74 (s, 2H), 4.57 (q, J=7.2 Hz, 2H), 1.41 (s, 9H).

To a degassed (argon) solution of tert-butyl 2-(3-bromo-1-ethyl-7-oxo-1,7-dihydro-6H-pyrazolo[4,3-d]pyrimidin-6-yl)acetate (81) (2.3 g, 6.46 mmol) in dioxane (25 mL) were added $Cs_2CO_3$ (6.2 g, 19.38 mmol), $Pd_2(dba)_3$ (591 mg, 0.64 mmol), Xantphos (373 mg, 0.64 mmol) and 4-(trifluoromethyl)aniline (1.0 g, 6.46 mmol) at RT. The solution was degassed again for 15 min and the mixture was heated at 100° C. in sealed tube for 3 h. The reaction mixture was cooled to room temperature and filtered through a celite pad. The celite pad was washed with 5% MeOH in $CH_2Cl_2$. The filtrate was concentrated under reduced pressure. The residue was purified by silica gel column to give tert-butyl 2-(1-ethyl-7-oxo-3-((4-(trifluoromethyl)phenyl)amino)-1,7-dihydro-6H-pyrazolo[4,3-d]pyrimidin-6-yl)acetate (82) (1.8 g, 64%) as a pale yellow solid. MS (ESI) m/z 438.09 $[M+H]^+$; $^1$H NMR (400 MHz, DMSO-$d_6$): δ 9.46 (s, 1H), 8.16 (s, 1H), 7.72 (d, J=8.4 Hz, 2H), 7.57 (d, J=8.4 Hz, 2H), 4.74 (s, 2H), 4.50 (q, J=7.2 Hz, 2H), 1.44 (s, 9H), 1.38 (t, J=7.2 Hz, 3H).

To a stirred solution of tert-butyl 2-(1-ethyl-7-oxo-3-((4-(trifluoromethyl)phenyl)amino)-1,7-dihydro-6H-pyrazolo [4,3-d]pyrimidin-6-yl)acetate (82) (1.8 g, 4.11 mmol) in DCM (10 mL) was added 4M solution of HCl in dioxane (10 mL) at 0° C. The reaction mixture was stirred at RT for 16 h. The reaction mixture was evaporated under reduced pressure and triturated with ether and dried under reduced pressure gave 2-(1-ethyl-7-oxo-3-((4-(trifluoromethyl)phenyl)amino)-1,7-dihydro-6H-pyrazolo[4,3-d]pyrimidin-6-yl) acetic acid (83) (1.1 g, 7.3%) as a pale yellow solid. MS (ESI) m/z 382.46 $[M+H]^+$; $^1$H NMR (400 MHz, DMSO-$d_6$): δ 9.46 (s, 1H), 8.17 (s, 1H), 7.71 (d, J=8.4 Hz, 2H), 7.57 (d, J=8.4 Hz, 2H), 4.77 (s, 2H), 4.52 (q, J=7.2 Hz, 2H), 1.40 (t, J=7.2 Hz, 3H).

To a stirred solution of 2-(1-ethyl-7-oxo-3-((4-(trifluoromethyl)phenyl)amino)-1,7-dihydro-6H-pyrazolo[4,3-d] pyrimidin-6-yl)acetic acid (83) (250 mg, 0.65 mmol) in DMF (3 mL) were added HATU (374 mg, 0.98 mmol), DIPEA (0.36 mL, 1.96 mmol) at 0° C. and reaction mixture was stirred for 5 min at same temperature. Then added 2-(((1r,4r)-4-aminocyclohexyl)methoxy)propan-2-ol (147 mg, 0.78 mmol) and the reaction was stirred at RT for 16 h. The reaction mixture was quenched with ice cold water. The precipitated solid was filtered and prep HPLC purification to afford 2-(1-ethyl-7-oxo-3-((4-(trifluoromethyl)phenyl) amino)-1,7-dihydro-6H-pyrazolo[4,3-d]pyrimidin-6-yl)-N-((1r,4r)-4-(2-hydroxy-2-methylpropoxy)cyclohexyl)acetamide (84) (39 mg, 10%) as an off-white solid. MS (ESI) m/z 551.72 $[M+H]^+$; $^1$H NMR (400 MHz, DMSO-$d_6$): δ 9.44 (s, 1H), 8.20 (d, J=7.6 Hz, 1H), 8.07 (s, 1H), 7.71 (d, J=8.4 Hz, 2H), 7.56 (d, J=8.8 Hz, 2H), 4.63 (s, 2H), 4.51 (q, J=4.4 Hz, 1H), 4.20 (s, 1H), 3.60-3.50 (br s, 1H), 3.30-3.20 (br s, 1H), 3.15 (s, 2H), 2.00-1.90 (m, 2H), 1.90-1.80 (m, 2H), 1.39 (t, J=7.2 Hz, 3H), 1.30-1.20 (m, 4H), 1.05 (s, 6H).

Example 33: Synthesis of N-((1r,4r)-4-(2-hydroxy-2-methylpropoxy)cyclohexyl)-2-(7-oxo-1-(2,2,2-trifluoroethyl)-3-((4-(trifluoromethyl)phenyl)amino)-1,7-dihydro-6H-pyrazolo[4,3-d]pyrimidin-6-yl) acetamide (92)

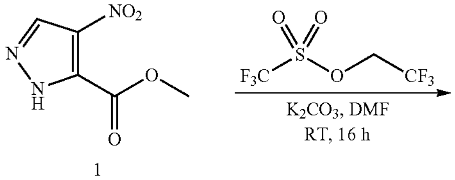

1

-continued

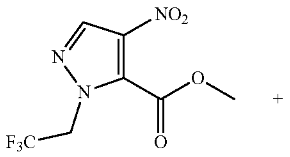

85

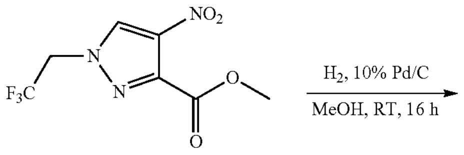

85a

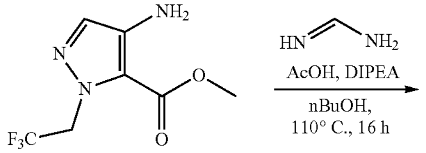

86

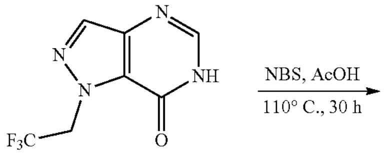

87

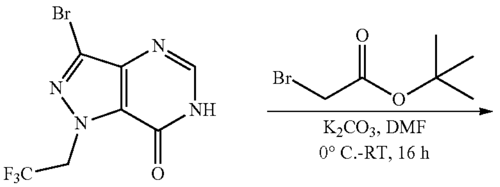

88

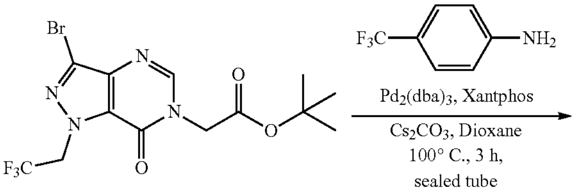

89

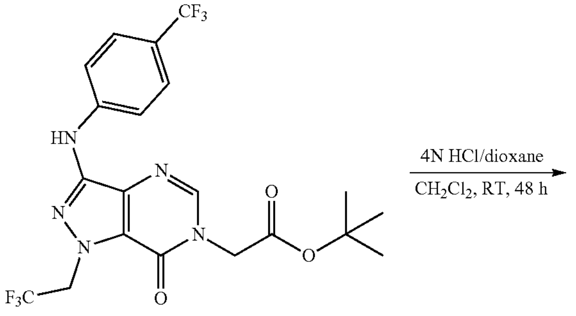

90

-continued

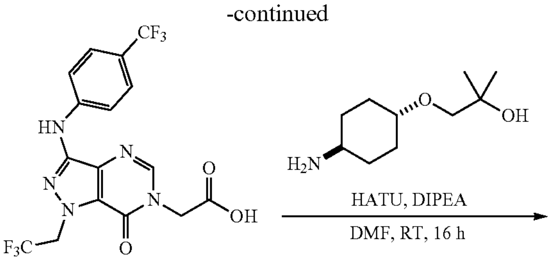

91

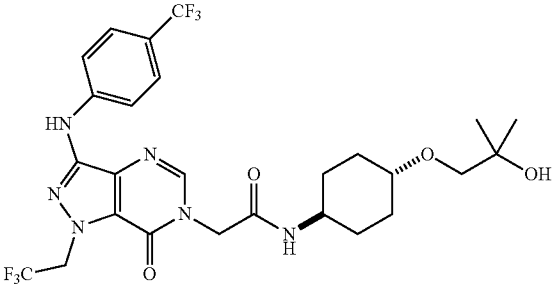

92

To a stirred solution of methyl 4-nitro-1H-pyrazole-5-carboxylate (1) (10 g, 58.4 mmol) in DMF (100 mL) were added $K_2CO_3$ (16.1 g, 116.9 mmol) followed by 2,2,2-trifluoroethyl trifluoromethanesulfonate (12.7 mL, 87.7 mmol) at RT. The reaction mixture was stirred for 16 h at same temperature. The reaction mixture was quenched with water and extracted with EtOAc. The organic layer was dried over anhydrous $Na_2SO_4$, filtered and concentrated. The residue was purified through a silica gel column to afford methyl 4-nitro-1-(2,2,2-trifluoroethyl)-1H-pyrazole-5-carboxylate (85) (4 g, 32% yield) as a colorless liquid and further elution gave the other isomer methyl 4-nitro-1-(2,2,2-trifluoroethyl)-1H-pyrazole-3-carboxylate (85a) (5 g). MS (ESI) m/z 254.14 $[M+H]^+$; $^1H$ NMR (400 MHz, DMSO-$d_6$): δ 9.57 (s, 1H), 5.41 (q, J=7.20 Hz, 2H), 3.98 (s, 3H).

To a stirred solution of methyl 4-nitro-1-(2,2,2-trifluoroethyl)-1H-pyrazole-5-carboxylate (85) (3.3 g, 13.04 mmol) in MeOH (33 mL) was added 10% Pd/C (2 g) and the reaction mixture was stirred at RT under hydrogen (50 PSI) atmosphere for 16 h. The reaction mixture was filtered through a celite pad and the filtrate was concentrated to obtain methyl 4-amino-1-(2,2,2-trifluoroethyl)-1H-pyrazole-5-carboxylate (86) (2.3 g, 82% yield). MS (ESI) m/z 224.09 $[M+H]^+$; $^1H$ NMR (400 MHz, DMSO-$d_6$): δ 7.24 (s, 1H), 5.09 (q, J=7.20 Hz, 2H), 4.20 (s, 2H), 3.93 (s, 3H).

To a stirred solution of methyl 4-amino-1-(2,2,2-trifluoroethyl)-1H-pyrazole-5-carboxylate (86) (2.3 g, 10.31 mmol) in n-butanol (23 mL) were added DIPEA (9.5 mL, 51.56 mmol) and formamidine acetate (2.1 g, 20.62 mmol) at RT. The reaction mixture was stirred at 110° C. for 16 h. The reaction mixture was cooled to RT and a precipitated solid was filtered off. The solid compound was triturated with diethyl ether to afford 1-(2,2,2-trifluoroethyl)-1,6-dihydro-7H-pyrazolo[4,3-d]pyrimidin-7-one (87) (2 g, 89% yield) as an off-white solid. MS (ESI) m/z 218.04 $[M+H]^+$; $^1H$ NMR (400 MHz, DMSO-$d_6$): δ 12.52 (brs, 1H), 8.21 (s, 1H), 7.98 (s, 1H), 5.46 (q, J=7.20 Hz, 2H).

To a stirred solution of 1-(2,2,2-trifluoroethyl)-1,6-dihydro-7H-pyrazolo[4,3-d]pyrimidin-7-one (87) (1.6 g, 7.33 mmol) in DMF (16' mL) was added NBS (6.5 g, 36.69 mmol) at RT. The reaction mixture was stirred at 110° C. for 30 h. The reaction mixture was cooled to RT, quenched with cold water and precipitated solid was filtered off. The solid was dried under vacuum to afford 3-bromo-1-(2,2,2-trifluoroethyl)-1,6-dihydro-7H-pyrazolo[4,3-d]pyrimidin-7-one (88) (1.0 g, 46% yield) as an off-white solid.
MS (ESI) m/z 297.04 $[M+H]^-$; $^1H$ NMR (400 MHz, DMSO-$d_6$): δ 12.79 (brs, 1H), 8.04 (s, 1H), 5.46 (q, J=7.20 Hz, 2H).

To a stirred solution of 3-bromo-1-(2,2,2-trifluoroethyl)-1,6-dihydro-7H-pyrazolo[4,3-d]pyrimidin-7-one (88) (1.0 g, 3.3 mmol) in DMF (10 mL) were added $K_2CO_3$ (935 g, 6.77 mmol) followed by tert-butyl bromoacetate (0.7 mL, 5.08 mmol). The reaction mixture was stirred at RT for 16 h. The reaction mixture was quenched with water (100 mL) and extracted with EtOAc (2×250 mL). The combined organic layer was dried over anhydrous $Na_2SO_4$, filtered and concentrated. The residue was purified by flash column chromatography over silica (100-200) to afford tert-butyl 2-(3-bromo-7-oxo-1-(2,2,2-trifluoroethyl)-1,7-dihydro-6H-pyrazolo[4,3-d]pyrimidin-6-yl)acetate (89) (600 mg, 43% yield) as an off-white solid. MS (ESI) m/z 410.02 $[M+H]^+$; 411.20.

To a degassed (argon) solution of tert-butyl 2-(3-bromo-7-oxo-1-(2,2,2-trifluoroethyl)-1,7-dihydro-6H-pyrazolo[4,3-d]pyrimidin-6-yl)acetate (89) (400 mg, 0.97 mmol) in dioxane (5 mL) were added $Cs_2CO_3$ (951 g, 2.92 mmol), $Pd_2(dba)_3$ (89 mg, 0.09 mmol), Xantphos (56 mg, 0.09 mmol) and 4-(trifluoromethyl)aniline (157 g, 0.97 mmol) at RT. The solution was degassed again for 15 min and mixture was heated at 100° C. in a sealed tube for 3 h. The reaction mixture was cooled to room temperature and filtered through a celite pad. The celite pad was washed with 5% MeOH in $CH_2Cl_2$. The filtrate was concentrated under reduced pressure. The residue was purified by silica gel column to give tert-butyl 2-(7-oxo-1-(2,2,2-trifluoroethyl)-3-((4-(trifluoromethyl)phenyl)amino)-1,7-dihydro-6H-pyrazolo[4,3-d]pyrimidin-6-yl)acetate (90) (250 mg, 52% yield) as a pale yellow solid. MS (ESI) m/z 491.13 $[M+H]^+$; 492.27

To a stirred solution of tert-butyl 2-(7-oxo-1-(2,2,2-trifluoroethyl)-3-((4-(trifluoromethyl)phenyl)amino)-1,7-dihydro-6H-pyrazolo[4,3-d]pyrimidin-6-yl)acetate (90) (250 mg, 0.50 mmol) in 1,4 dioxane (3 mL) was added 4M solution of HCl in dioxane (3 mL) at 0° C. The reaction mixture was stirred at RT for 48 h. The reaction mixture was evaporated under reduced pressure and triturated with ether and dried under reduced pressure gave 2-(7-oxo-1-(2,2,2-trifluoroethyl)-3-((4-(trifluoromethyl)phenyl)amino)-1,7-dihydro-6H-pyrazolo[4,3-d]pyrimidin-6-yl)acetic acid (91) (200 mg, 90%) as a pale yellow solid. MS (ESI) m/z 435.07 $[M+H]^+$; $^1H$ NMR (400 MHz, DMSO-$d_6$): δ 13.32 (br s, 1H), 9.71 (s, 1H), 8.30 (s, 1H), 7.99 (d, J=8.40 Hz, 2H), 7.61 (d, J=8.8 Hz, 2H), 5.35 (q, J=8.80 Hz, 2H), 4.78 (s, 2H).

To a stirred solution of 2-(7-oxo-1-(2,2,2-trifluoroethyl)-3-((4-(trifluoromethyl)phenyl)amino)-1,7-dihydro-6H-pyrazolo[4,3-d]pyrimidin-6-yl)acetic acid (91) (200 mg, 0.45 mmol) in DMF (3 mL) were added HATU (262 mg, 0.68 mmol), DIPEA (0.25 mL, 1.37 mmol) at 0° C. and the reaction mixture was stirred for 5 min at the same temperature. Then added 2-(((1r,4r)-4-aminocyclohexyl)methoxy)propan-2-ol (103 mg, 0.55 mmol) and the reaction was stirred at RT for 16 h. The reaction mixture was quenched with ice cold water. The precipitated solid was filtered and prep HPLC purification to afford N-((1r,4r)-4-(2-hydroxy-2-methylpropoxy)cyclohexyl)-2-(7-oxo-1-(2,2,2-trifluoroethyl)-3-((4-(trifluoromethyl)phenyl)amino)-1,7-dihydro-6H-pyrazolo[4,3-d]pyrimidin-6-yl)acetamide (92) (50 mg, 18% yield) as an off-white solid. MS (ESI) m/z 605.36 $[M+H]^+$; $^1H$ NMR (400 MHz, DMSO-$d_6$): δ 9.70 (s, 1H), 8.30-8.20 (m, 2H), 7.81 (d, J=8.4 Hz, 2H), 7.60 (d, J=8.8 Hz, 2H), 5.34 (q, J=8.80 Hz, 2H), 4.64 (s, 2H), 4.20 (s, 1H), 3.60-3.50 (br s, 1H), 3.30-3.20 (br s, 1H), 3.14 (s, 2H), 2.00-1.90 (m, 2H), 1.90-1.80 (m, 2H), 1.30-1.20 (m, 4H), 1.05 (s, 6H).

Example 34: Synthesis of N-(3-fluoro-4-methoxyphenyl)-2-(1-isopropyl-7-oxo-3-((4-(trifluoromethyl)phenyl)amino)-1,7-dihydro-6H-pyrazolo[4,3-d]pyrimidin-6-yl)acetamide (98)

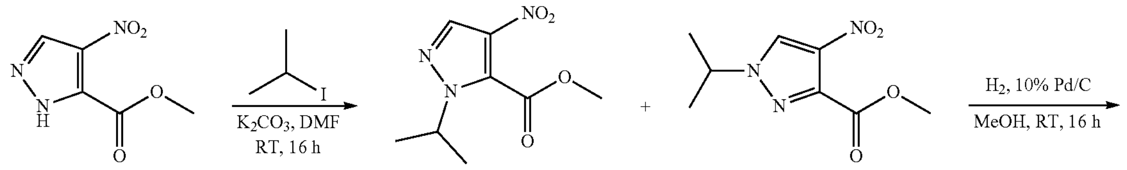

1 93 93a

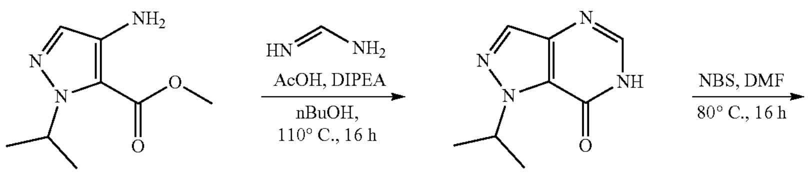

94 95

-continued

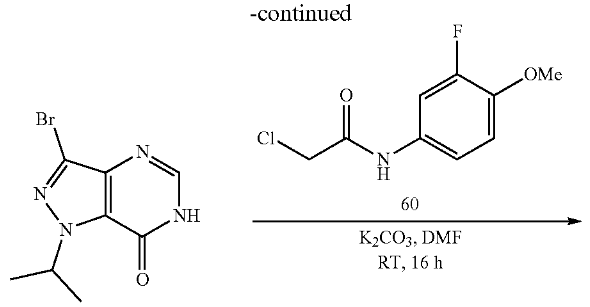

96

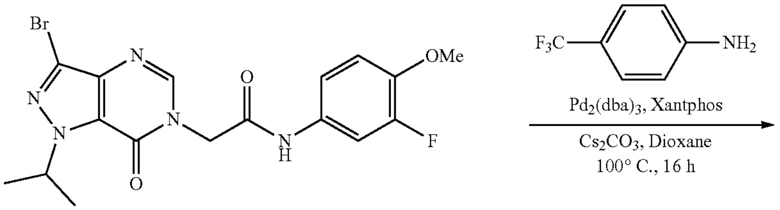

97

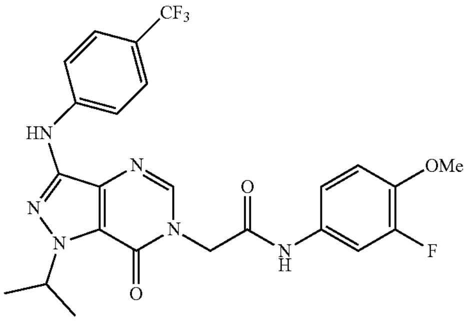

98

To a stirred solution of methyl 4-nitro-1H-pyrazole-5-carboxylate (1) (5 g, 29.22 mmol) in DMF (50 mL) were added $K_2CO_3$ (8.04 g, 58.44 mmol) followed by 2-iodopropane (5.46 g, 32.11 mmol) at RT and the reaction mixture was stirred for 16 h at same temperature. The reaction mixture was quenched with water (100 mL) and extracted with EtOAc (2×100 mL). The combined organic layer was dried over anhydrous $Na_2SO_4$, filtered and concentrated. The residue was purified through silica gel column to give methyl 1-isopropyl-4-nitro-1H-pyrazole-5-carboxylate (93) (2.0 g, 32%). MS (ESI) m/z 213.07 $[M+H]^+$; $^1H$ NMR (400 MHz, DMSO-$d_6$): δ 8.41 (s, 1H), 4.75-4.70 (m, 1H), 4.00 (s, 2H), 1.44 (d, J=6.8 Hz, 6H).

To a stirred solution of methyl 1-isopropyl-4-nitro-1H-pyrazole-5-carboxylate (93) (2.0 g, 9.38 mmol) in MeOH (20 mL) was added 10% Pd/C (1.0 g). The reaction mixture was stirred at RT under a hydrogen (50 PSI) atmosphere for 8 h. The reaction mixture was filtered through a celite pad and the filtrate was concentrated to obtain methyl 4-amino-1-isopropyl-1H-pyrazole-5-carboxylate (94) (1.4 g, 81% yield) as a brown solid. MS (ESI) m/z 184.20 $[M+H]^+$; $^1H$ NMR (400 MHz, DMSO-$d_6$): δ 7.05 (s, 1H), 5.30-5.15 (m, 1H), 4.99 (s, 2H), 3.79 (s, 3H), 1.31 (d, J=6.8 Hz, 6H).

To a stirred solution of methyl 4-amino-1-isopropyl-1H-pyrazole-5-carboxylate (94) (1.4 g, 7.64 mmol) in n-butanol (80 mL) were added DIPEA (6.65 mL, 38.2 mmol), formamidine acetate (874.9 mg, 8.40 mmol) at RT. The reaction mixture was stirred at 110° C. for 3 h. The reaction mixture was cooled to RT and the precipitated solid was filtered off. The solid compound was triturated with diethyl ether to afford 1-isopropyl-1,6-dihydro-7H-pyrazolo[4,3-d]pyrimidin-7-one (95) (1.0 g, 73%) as an off-white solid. MS (ESI) m/z 179.18 $[M+H]^+$.

To a stirred solution of 1-isopropyl-1,6-dihydro-7H-pyrazolo[4,3-d]pyrimidin-7-one (95) (1 g, 5.61 mmol) in DMF (10 mL) was added NBS (2.19 g, 12.34 mmol) at RT. The reaction mixture was stirred at 80° C. for 12 h. The reaction mixture was cooled to RT, quenched with cold water and the precipitated solid was filtered off. The solid was dried under vacuum to afford 3-bromo-1-isopropyl-1,6-dihydro-7H-pyrazolo[4,3-d]pyrimidin-7-one (96) (700 mg, 49%) as an off-white solid. MS (ESI) m/z 257.21 $[M+H]^+$; $^1H$ NMR (400 MHz, DMSO-$d_6$): δ 12.51 (s, 1H), 7.92 (s, 1H), 5.40-5.30 (m, 1H), 4.87 (s, 2H), 1.47 (d, J=6.8 Hz, 6H).

To a stirred solution of 3-bromo-1-isopropyl-1,6-dihydro-7H-pyrazolo[4,3-d]pyrimidin-7-one (96) (500 mg, 1.94 mmol) in DMF (10 mL) were added $K_2CO_3$ (803.1 mg, 5.82 mmol) followed by 2-chloro-N-(3-fluoro-4-methoxyphenyl) acetamide (60) (423 mg, 1.94 mmol) at RT. The reaction mixture was stirred at 60° C. for 16 h. The reaction mixture was quenched with water (100 mL) and extracted with EtOAc (2×250 mL). The combined organic layer was dried over anhydrous $Na_2SO_4$, filtered and concentrated. The residue was purified by flash column chromatography over 100-200 silica to afford 2-(3-bromo-1-isopropyl-7-oxo-1,7-dihydro-6H-pyrazolo[4,3-d]pyrimidin-6-yl)-N-(3-fluoro-4-methoxyphenyl)acetamide (97) (350 mg, 41% yield) as an off-white solid. MS (ESI) m/z 438.28 $[M+H]^+$; $^1H$ NMR (400 MHz, DMSO-$d_6$): δ 10.57 (brs, 1H), 8.24 (s, 1H), 7.54 (d, J=10.8 Hz, 1H), 7.26 (d, J=8.8 Hz, 1H), 7.15 (d, J=8.8 Hz, 1H), 5.40-5.30 (m, 1H), 4.87 (s, 2H), 3.80 (s, 3H), 1.45 (d, J=6.8 Hz, 6H).

To a degassed (argon) solution of 2-(3-bromo-1-isopropyl-7-oxo-1,7-dihydro-6H-pyrazolo[4,3-d]pyrimidin-6-yl)-N-(3-fluoro-4-methoxyphenyl)acetamide (97) (330 mg, 0.752 mmol) in dioxane (6 mL) were added $Cs_2CO_3$ (735 mg, 2.25 mmol), $Pd_2(dba)_3$ (68 mg, 0.075 mmol), Xantphos (43 mg, 0.075 mmol) and 5-(trifluoromethyl)pyridin-2-amine (181 mg, 1.12 mmol) at RT. The solution was degassed again for 15 min and the reaction mixture heated at 100° C. in a microwave for 3 h. The reaction mixture was cooled to room temperature and filtered through a celite pad. The celite pad was washed with 5% MeOH in $CH_2Cl_2$. The filtrate was concentrated under reduced pressure. The residue was purified by prep-HPLC to afford N-(3-fluoro-4-methoxyphenyl)-2-(1-isopropyl-7-oxo-3-((4-(trifluoromethyl)phenyl)amino)-1,7-dihydro-6H-pyrazolo[4,3-d]pyrimidin-6-yl)acetamide (98) (74 mg, 19%) as a pale yellow solid. MS (ESI) m/z 519.17 $[M+H]^+$; $^1$H NMR (400 MHz, DMSO-$d_6$): δ 10.49 (s, 1H), 9.46 (s, 1H), 8.16 (s, 1H), 7.70 (d, J=8.8 Hz, 2H), 7.57 (d, J=8.8 Hz, 2H), 7.53 (s, 1H), 7.27 (d, J=8.8 Hz, 1H), 7.14 (t, J=9.2 Hz, 1H), 5.40-5.30 (m, 1H), 4.87 (s, 2H), 3.80 (s, 3H), 1.47 (d, J=6.8 Hz, 6H).

Example 35: SF-1 Luc Assay

Vector Construction: pGal4DBD_SF-1LBD was generated by cloning polymerase chain reaction fragments encoding either human SF-1 (aa 198-462) ligand-binding domain (LBD) in frame with the DNA-binding domain (DBD) of the yeast transcriptional factor Gal4 encoded by the pFA-CMV vector (Stratagene, La Jolla, CA). SF-1 (aa 198-462) was amplified from an Invitrogen expressed sequence tag clone (San Diego, CA). BamHI and XbaI sites introduced by the primers GATCGGATCCCCGGAGCCTTATGCCAGCCC (forward) and GATCTCTAGATCAAGTCTGCTTGGCTTGCAGCATTTCGATGAG (reverse) were used for subcloning the amplicon into pFA-CMV.

Cell Culture and Transient Transfection Conditions: Chinese hamster ovary (CHO) cells of the K1 subtype (American Type Culture Collection, Manassas, VA) were grown in T-175 flasks (Corning Life Sciences, Acton, MA) at 37° C., 5% $CO_2$, 95% relative humidity in Ham's F-12 media (Gibco, Carlsbad, CA) supplemented with 10% (v/v) fetal bovine serum (Gemini Bio-products, West Sacramento, CA) and 1% (v/v) penicillin/streptomycin mix (Gibco). Cells were routinely cultured by splitting them from 1:10 to 1:20. The day before transfection, cells were rinsed with PBS and trypsinized with a 0.25% trypsin-EDTA solution (Gibco), then $6\times10^6$ CHO-K1 cells were seeded in T-175 flasks containing 20 ml of Ham's F-12 media supplemented as mentioned above. Cells were allowed to incubate overnight at 37° C., 5% CO2 and 95% relative humidity (RH). On the following day, CHO-K1 cells were transiently cotransfected with either 250 ng of pGal4DBD_SF-1LBD plasmid or 125 ng of pGal4DBD_RORALBD in combination with 9 μg of pG5luc (Promega, Madison, WI) and 8.75 μg of empty pcDNA3.1 (Invitrogen), in 1.2 mL of Ham's F-12 media containing 54 μl of TransIT-CHO reagent and 9 μL of TransIT-CHO Mojo reagent, according to the manufacturer's protocol (Mirus Bioproducts, Madison, WI). Flasks containing transfected cells were then placed back in the incubator at 37° C., 5% $CO_2$ and 95% relative humidity. Four hours after transfection, cells were trypsinized and suspended to a concentration of $1.6\times10^5$ cells/ml in supplemented Ham's F-12 media.

Assays: The collected cells were resuspended in the culture medium and plated into a 384 well-white plate (Corning Life Sciences, Acton, MA) at 8,000 cells/50 μL/well. The 384-plate was incubated at room temperature for 1 hr and then further incubated at 37° C., 5% $CO_2$ for 3 hr. The test article solutions were added into the 384-plate and incubated at 37° C., 6% $CO_2$ for 40 hours.

Cell viability was tested by a fluorescence method using Resazurin. After the incubation of the transfected CHO cells with the test article solutions, 10 μL of 20 μmol/L Resazurin solution was added into the 384 well-plate. Then, the fluorescence was measured immediately at 615 nm with the excitation wavelength of 570 nm (0 hr reading). After incubation at 37° C., 6% $CO_2$ for 2 hr, the fluorescence was measured at 615 nm with the excitation wavelength of 570 nm again (2 hr reading). The fluorescence counts (2 hr-0 hr) were calculated by subtracting the 0 hr readings from the 2 hr readings.

Measurement of SF-1 Transcriptional Activity: SF-1 transcriptional activity was detected as the intracellular Luc activity using SteadyLite Plus HTS Reporter Gene Assay System. After the measurement of the cell viability, the culture media in the 384 well-plate were completely removed. Then, 30 μL of the Luc substrate solution was added into each well and incubated for 10 min at room temperature. After the incubation, luminescence of each well was measured by a microplate reader.

Calculation of the Cell Viability (%): Cell viability (%) was calculated according to the following equation:

$$\text{Cell viability (\%)}=(A/B)\times100 \qquad \text{Equation}$$

A: mean fluorescence count (2 hr-0 hr) in the test article group

B: mean fluorescence count (2 hr-0 hr) in the vehicle group

Calculation of the SF-1 Transcriptional Activity (% of Control): The % of control for the transcriptional activity was calculated according to the following equation:

$$\text{\% of control}=A/B\times100 \qquad \text{Equation}$$

A: luminescence count in the test article-treated CHO cells transfected with GAL4-SF-1 plasmid B: mean luminescence count in the vehicle-treated CHO cells transfected with GAL4-SF-1 plasmid EC50 Calculation: Half maximal effective concentration (EC50) was calculated by embedded software from Collaborative Drug Discovery Inc. (CDD). Potency of compounds is shown in Table 1:

TABLE 1

| Compound Number | hSF-1-Luc: EC50 |
|---|---|
| 11 | ++++ |
| 12 | ++++ |
| 13 | ++++ |
| 14 | ++++ |
| 15 | +++ |
| 16 | +++ |
| 17 | ++++ |
| 18 | ++++ |
| 19 | +++ |
| 20 | ++++ |
| 21 | ++++ |
| 22 | ++++ |
| 23 | ++++ |

TABLE 1-continued

| Compound Number | hSF-1-Luc: EC50 |
|---|---|
| 24 | ++++ |
| 25 | ++++ |
| 26 | ++++ |
| 27 | ++++ |
| 28 | +++ |
| 32 | ++++ |
| 36 | ++++ |
| 39 | ++++ |
| 43 | ++++ |
| 44 | ++++ |
| 48 | ++++ |
| 49 | ++++ |
| 52 | ++ |
| 55 | +++ |
| 63 | 75% inhibition at 8 uM |
| 64 | ++ |
| 65 | ++++ |
| 68 | +++ |
| 70 | ++++ |
| 71 | ++++ |
| 77 | ++++ |
| 80 | ++++ |
| 84 | ++++ |
| 92 | +++ |
| 98 | +++ |

++++ = $EC_{50}$ < 200 nM;
+++ = 200 nM ≤ $EC_{50}$ < 1 μM;
++ = 1 μM ≤ $EC_{50}$ ≤ 10 μM;
+ = 10 μM < $EC_{50}$ ≤ 20 μM

Example 36: R2C Proliferation Assay for SF-1 Antagonists

SF-1 regulates progenitor cell formation and survival in adult Leydig cells. Anti-proliferative effects of SF-1 antagonists using a SF-1+ rat Leydig tumor cell line, R2C, was investigated. Cell proliferation was measured by detecting DNA incorporation of EdU, a nucleoside analogue that can be fluorescently tagged after cell fixation.

Methods

Proliferation of the rat Leydig tumor cell line R2C (ATCC® CCL-97™) was assessed using 5-ethynyl-2'-deoxyuridine (EdU), a nucleoside analogue incorporated during DNA synthesis that can be fluorescently tagged after cell fixation. Cycloheximide, a protein synthesis inhibitor, was used as a positive control for the assay.

R2C cells are maintained according to a protocol provided by the American Type Culture Collection (ATCC). At the time of assay, R2C cells were diluted to 1.0 million cells/mL with culture medium (F12 medium supplemented with 2% FBS and 1% Penicillin-Streptomycin) and 50 uL of cell suspension seeded into each well of 384-well clear bottom plates. The assay plates were incubated in a humidified, 37° C., 6% $CO_2$ atmosphere for 24 hours. Serially diluted SF-1 antagonists, cycloheximide or vehicle (DMSO) were then applied to the R2C cells and incubated in a humidified, 37° C., 6% $CO_2$ atmosphere for two days. EdU (Invitrogen), at a final concentration of 5 μM, was added to the cells and incubated for an additional 16 hours, after which cells were fixed with 10% formalin.

Cells were then washed and permeabilized in 0.5% TritonX-100/PBS solution at RT for 1 hour. EdU incorporation was detected by labeling EdU with 6-FAM azide (Lumiprobe) using a copper (I)-catalyzed Click reaction between an azide and alkyne. The reaction mixture consists of 5 mM ascorbic acid, 1 mM $CuSO_4$, 1 μM 6-FAM azide dissolved in PBS buffer. The fluorescent signal was detected by using an EnVision 2104 Multimode Plate Reader. For data normalization, the average fluorescence of DMSO wells was defined as 100%, and average fluorescence of 10 μM cycloheximide wells was defined as 0%. Curve fitting and $EC_{50}$ determination were performed using the variable slope sigmoidal dose-response analysis.

Preparation of the Various Medium and Reagents

Preparation of R2C Culture Medium

Preparation method: Culture medium was prepared by adding 92 mL of horse serum (Invitrogen), 15.5 mL fetal bovine serum and 6.1 mL of penicillin (10,000 units/mL) streptomycin (10 mg/mL) solution to 500 mL of Ham's F-12 medium (Invitrogen). The culture medium was stored in a refrigerator (set at 4° C.) and used within one month of preparation.

Preparation of R2C Plating Medium

Preparation method: Culture medium was prepared by adding 10 mL of fetal bovine serum and 5.1 mL of penicillin (10,000 units/mL) streptomycin (10 mg/mL) solution to 500 mL of Ham's F-12 medium. The culture medium was stored in a refrigerator (set at 4° C.) and used within one month of preparation.

Preparation of R2C Daughter Plate Medium

Preparation method: Culture medium was prepared by adding 50 mL of fetal bovine serum and 5.5 mL of penicillin (10,000 units/mL) streptomycin (10 mg/mL) solution to 500 mL of Ham's F-12 medium. The culture medium was stored in a refrigerator (set at 4° C.) and used within one month of preparation.

Preparation of the Cycloheximide (Positive Control) Solutions

Preparation method: Cycloheximide was dissolved in DMSO to obtain a concentration of 5 mmol/L. The 5 mmol/L solution were diluted 20-fold into R2C daughter plate medium to obtain daughter plate. The daughter plate was then added to assay plates to obtain the final test conditions.

Preparation of the Test Article Solutions

Preparation method: The test article was dissolved in DMSO to obtain a concentration of 10 mmol/L. The 10 mmol/L was further diluted in DMSO to obtain a concentration of 256 μmol/L. The 10 mmol/L and/or the 256 μmol/L solutions was serially diluted 2.5-fold into vehicle to obtain a 10-point dilution. These solutions were diluted 20-fold into R2C daughter plate medium to obtain serial diluted test article daughter plate. The daughter plate was then added to assay plates to obtain the final test conditions.

Preparation of EdU Plating Solution

Preparation method: EdU was dissolved in DMSO to obtain a EdU stock solution with a concentration of 30 mmol/L. The 30 mmol/L EdU stock solution was stored in a freezer (set at −20° C.). At the time of use, add 25 μl of 30 mM EdU stock solution into 25 ml R2C plating medium to obtain EdU plating solution.

Preparation of 6-FAM Azide Solution

Preparation method: 6-FAM azide was dissolved in DMSO to obtain a concentration of 30 mmol/L. The 30 mmol/L stock solution was further diluted to 1 mmol/L to obtain working solution.

Preparation of the 25 mL 2× Mounting Mix Solution

Preparation method: ascorbic acid was dissolved in PBS to obtain a concentration of 1 mol/L. Copper(II) sulfate was dissolved in water to obtain a concentration of 0.2 mol/L. 25 mL 2× mounting mix solution was prepared by adding 1. 24.4 mL PBS, 2. 0.25 mL of 1M ascorbic acid solution, 3. 0.25 mL of 0.2M $CuSO_4$ solution, 4. 0.05 mL of 1 mM 6-FAM azide DMSO solution. The 2× mounting mix solution was used at the time of preparation.

Hoechst 33258 Staining Solution

Preparation method: ascorbic acid was dissolved in PBS to obtain a concentration of 1 mol/L. Copper(II) sulfate was dissolved in water to obtain a concentration of 0.2 mol/L. 25 mL 2× mounting mix solution was prepared by adding 1. 24.4 mL PBS, 2. 0.25 mL of 1M ascorbic acid solution, 3. 0.25 mL of 0.2M $CuSO_4$ solution, 4. 0.05 mL of 1 mM 6-FAM azide DMSO solution. The 2× mounting mix solution was used at the time of preparation.

Study Procedures

Incubation of the R2C Cells with the Test Article

R2C cells were routinely cultured in R2C culture medium. To assay SF-1 antagonist inhibitory activity, R2C cells were resuspended in the R2C plating medium and plated into a 384 well-clear bottom black plate at 20,000 cells/50 μL/well. The 384-plate was incubated at 37° C., 6% $CO_2$ for 24 hours to allow cell attachment to assay plates. The serial diluted test article solutions, the cycloheximide positive control solutions, or the vehicle solutions were then added into the 384-plate and incubated at 37° C., 6% $CO_2$ for two days. 10 μL EdU plating solution were then dispensed into each well of assay plate incubated at 37° C., 6% $CO_2$ for two days.

Measurement of the R2C Cell Proliferation

R2C proliferation is measured by detecting the fluorescent labelled EdU. The R2C assay plates were fixed by dispense 60 μL of 10% formalin into each well, and the plates were incubated at room temperature for 1 hour on an orbital shaker. The plates were washed with 80 μL of PBS three times, and cells were permeabilized by treating with 100 μL of PBS-0.5% TritonX-100 at RT for 1 hour on an orbital shaker. The plates were washed with 80 μL of PBS three times, and after the last wash, 25 μL of PBS was dispensed into each well. 25 μL of 2× mounting mix solution was then added into each well of fixed cells, and the plates were incubated at RT for 30 min in the dark on an orbital shaker. The cells were washed with 80 μL of PBS, three times, and after the last wash, 25 μL of PBS was dispensed into each well. 25 μL of Hoechst 33258 staining solution was then added into each well of fixed cells, and the plates were incubated at RT for 30 min in the dark on an orbital shaker. The cells were washed with 80 μL of PBS, three times, and after the last wash, 50 μL of PBS was dispensed into each well. Assay plates were sealed with aluminum foil, and fluorescence was measured using a Envision microplate reader.

Calculation of the R2C Proliferation Activity (% of Control)

The % of control for the proliferation activity was calculated according to the following equation:

$$\%\text{ of control}=100\times(A-C)/(B-C) \quad \text{Equation}$$

A: fluorescence count in the test article-treated R2C cells

B: mean fluorescence count in the vehicle-treated R2C cells

C: mean fluorescence count in the 10 μM cycloheximide-treated R2C cells

EC50 Calculation: Half maximal effective concentration (EC50) was calculated by embedded software from Collaborative Drug Discovery Inc. (CDD). Potency of compounds is shown in Table 2:

TABLE 2

| Compound Number | R2C: EC50 |
|---|---|
| 11 | ++++ |
| 12 | ++++ |
| 13 | +++ |
| 14 | +++ |
| 15 | ++ |
| 16 | ++ |
| 17 | +++ |
| 18 | ++++ |
| 19 | +++ |
| 20 | ++++ |
| 21 | ++++ |
| 22 | ++++ |
| 23 | ++++ |
| 24 | ++++ |
| 25 | ++++ |
| 26 | ++++ |
| 27 | ++++ |
| 28 | ++ |
| 32 | ++++ |
| 36 | +++ |
| 39 | ++++ |
| 43 | ++++ |
| 44 | ++++ |
| 48 | ++++ |
| 49 | ++++ |
| 52 | 72% inhibition at 8 μM |
| 55 | ++ |
| 63 | 19% inhibition at 8 μM |
| 64 | ++ |
| 65 | +++ |
| 68 | ++ |
| 70 | ++ |
| 71 | ++++ |
| 77 | ++++ |
| 80 | ++++ |
| 84 | ++++ |
| 92 | +++ |
| 98 | ++ |

++++ = $EC_{50}$ < 200 nM;
+++ = 200 nM ≤ $EC_{50}$ < 1 μM;
++ = 1 μM ≤ $EC_{50}$ ≤ 10 μM;
+ = 10 μM < $EC_{50}$ ≤ 20 μM

What is claimed is:

1. A compound having the structure of Formula (I):

Formula (I)

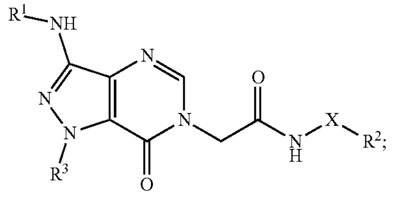

wherein:

X is a bond or $C_1$-$C_6$alkylene;

$R^1$ is selected from $C_{3-8}$cycloalkyl, $C_{2-9}$heterocycloalkyl, —$CH_2C_{6-10}$aryl, $C_{6-10}$aryl, and $C_{1-9}$heteroaryl, wherein $C_{3-8}$cycloalkyl, $C_{2-9}$heterocycloalkyl, —$CH_2C_{6-10}$aryl, $C_{6-10}$aryl and $C_{1-9}$heteroaryl are optionally substituted with one, two, three, four, or five $R^4$;

$R^2$ is selected from $C_{3-8}$cycloalkyl, $C_{2-9}$heterocycloalkyl, $C_{6-10}$aryl and $C_{1-9}$heteroaryl, wherein $C_{3-8}$cycloalkyl, $C_{2-9}$heterocyclkyl, $C_{6-10}$aryl and $C_{1-9}$heteroaryl are optionally substituted with one, two, three, four, or five $R^5$;

$R^3$ is hydrogen, $C_1$-$C_6$alkyl, $C_1$-$C_6$haloalkyl, or $C_{3-8}$cycloalkyl;

each $R^4$ and each $R^5$ are each independently selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^6$, —$SR^6$, —C(O)$OR^6$, —OC(O)N($R^6$)($R^7$), —N($R^8$)C(O)N($R^6$)($R^7$), —N($R^8$)C(O)$R^9$, —N($R^8$)C(O)$OR^9$, —N($R^8$)S(O)$_2R^9$, —C(O)$R^9$, —OC(O)$R^9$, —C(O)N($R^6$)($R^7$), —C(O)C(O)N($R^6$)($R^7$), —S(O)$R^9$, —S(O)$_2R^9$, and —S(O)$_2$N($R^6$)($R^7$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —C(O)$OR^{10}$, —OC(O)N($R^{10}$)($R^{11}$), —N($R^{12}$)C(O)N($R^{10}$)($R^{11}$), —N($R^{12}$)C(O)$R^{13}$, —N($R^{12}$)C(O)$OR^{13}$, —N($R^{12}$)S(O)$_2R^{13}$, —C(O)$R^{13}$, —OC(O)$R^{13}$, —C(O)N($R^{10}$)($R^{11}$), —C(O)C(O)N($R^{10}$)($R^{11}$), —S(O)$R^{13}$, —S(O)$_2R^{13}$, and —S(O)$_2$N($R^{10}$)($R^{11}$);

each $R^6$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^7$ is independently selected from hydrogen, $C_{1-6}$alkyl, and $C_{1-6}$haloalkyl;

each $R^8$ is independently selected from hydrogen, $C_{1-6}$alkyl, and $C_{1-6}$haloalkyl;

each $R^9$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl; and each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

or a pharmaceutically acceptable salt or solvate thereof.

2. The compound of claim 1, or a pharmaceutically acceptable salt or solvate thereof, wherein $R^1$ is selected from $C_{6-10}$aryl and $C_{1-9}$heteroaryl, wherein $C_{6-10}$aryl and $C_{1-9}$heteroaryl are optionally substituted with one, two, three, four, or five $R^4$.

3. The compound of claim 2, or a pharmaceutically acceptable salt or solvate thereof, wherein $R^1$ is phenyl optionally substituted with one, two, or three $R^4$.

4. The compound of claim 3 or a pharmaceutically acceptable salt or solvate thereof, wherein each $R^4$ is independently selected from halogen, —CN, $C_{1-6}$alkyl, $C_{1-6}$haloalkyl, and —$OR^6$.

5. The compound of claim 4, or a pharmaceutically acceptable salt or solvate thereof, wherein each $R^4$ is independently selected from $C_{1-6}$haloalkyl.

6. The compound of claim 1, or a pharmaceutically acceptable salt or solvate thereof, wherein $R^2$ is $C_{3-8}$cycloalkyl optionally substituted with one, two, three, four, or five $R^5$.

7. The compound of claim 6, or a pharmaceutically acceptable salt or solvate thereof, wherein $R^2$ is cyclohexyl optionally substituted with one, two, or three $R^5$.

8. The compound of claim 1, or a pharmaceutically acceptable salt or solvate thereof, wherein $R^2$ is $C_{6-10}$aryl optionally substituted with one, two, three, four, or five $R^5$.

9. The compound of claim 8, or a pharmaceutically acceptable salt or solvate thereof, wherein $R^2$ is phenyl optionally substituted with one, two, or three $R^5$.

10. The compound of claim 1, or a pharmaceutically acceptable salt or solvate thereof, wherein each $R^5$ is independently selected from halogen, $C_{1-6}$haloalkyl, —$OR^6$, and $C_{1-6}$alkyl optionally substituted with one group selected from —$OR^{10}$, —C(O)$OR^{10}$, —C(O)N($R^{10}$)($R^{11}$), —S(O)$_2R^{13}$, and —S(O)$_2$N($R^{10}$)($R^{11}$).

11. The compound of claim 10, or a pharmaceutically acceptable salt or solvate thereof, wherein each $R^5$ is independently selected from halogen, —$OR^6$, and $C_{1-6}$alkyl optionally substituted with one group selected from —$OR^{10}$, —C(O)$OR^{10}$, —C(O)N($R^{10}$)($R^{11}$), and —S(O)$_2R^{13}$.

12. The compound of claim 11, or a pharmaceutically acceptable salt or solvate thereof, wherein each $R^6$ is independently selected from hydrogen and $C_{1-6}$alkyl optionally substituted with one, two, or three groups selected from halogen and hydroxy.

13. The compound of claim 11, or a pharmaceutically acceptable salt or solvate thereof, wherein each $R^{10}$ is independently selected hydrogen, $C_{1-6}$alkyl, and $C_{1-6}$haloalkyl.

14. The compound of claim 1, or a pharmaceutically acceptable salt or solvate thereof, wherein $R^3$ is $C_1$-$C_6$alkyl.

15. The compound of claim 1, or a pharmaceutically acceptable salt or solvate thereof, wherein X is a bond.

16. The compound of claim 1 selected from:

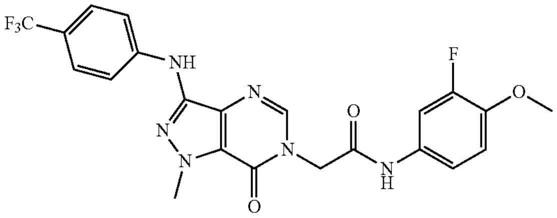
,

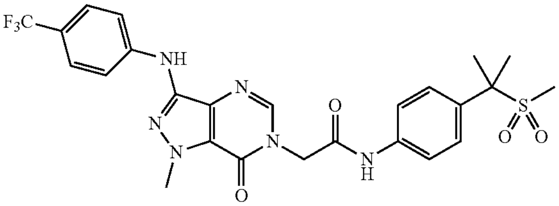
,

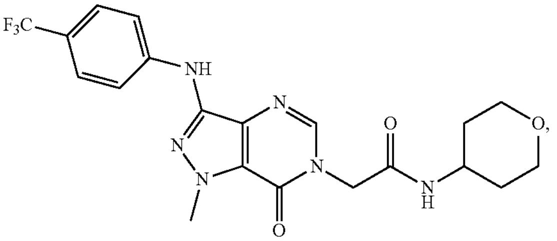

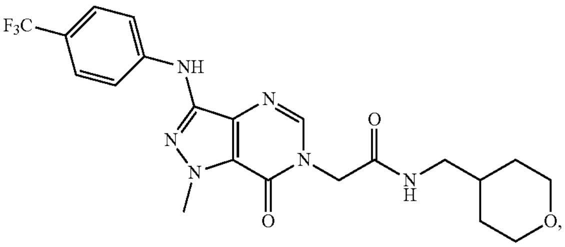

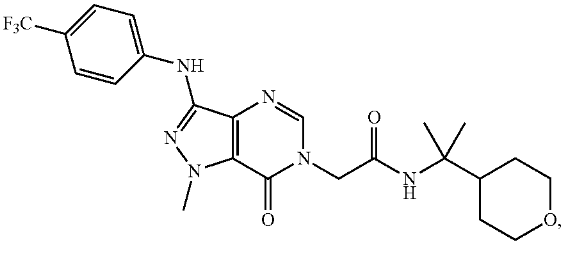

-continued

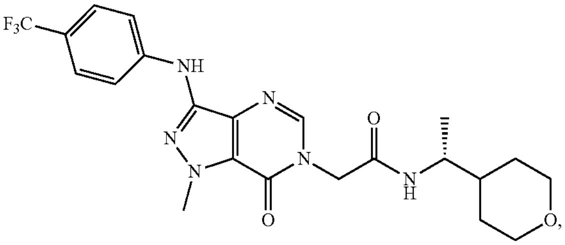

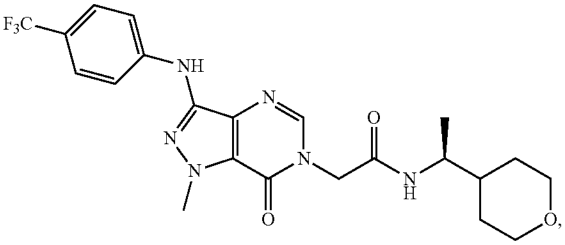

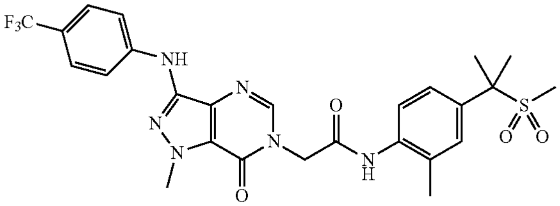
,

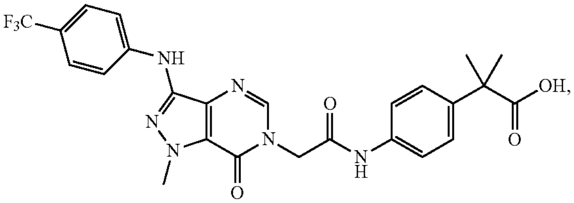

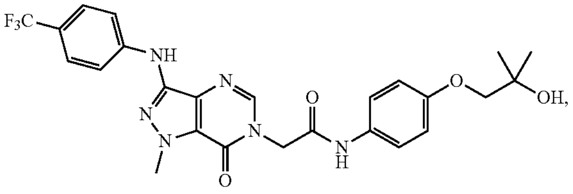

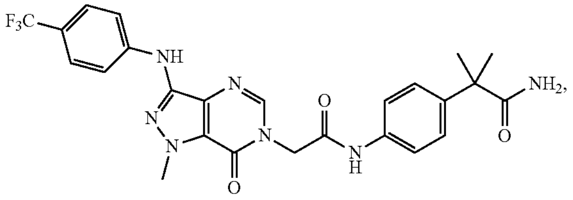

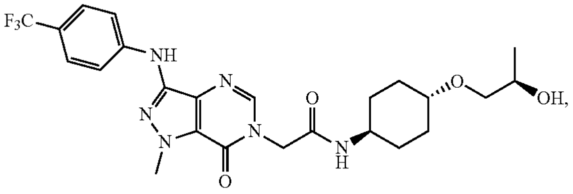

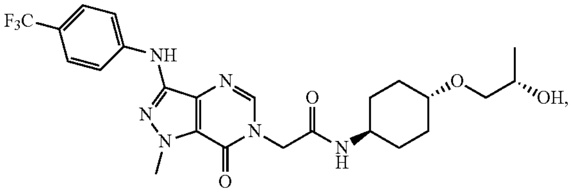

-continued
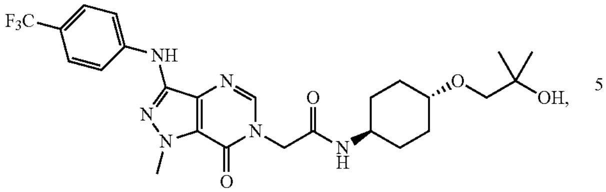
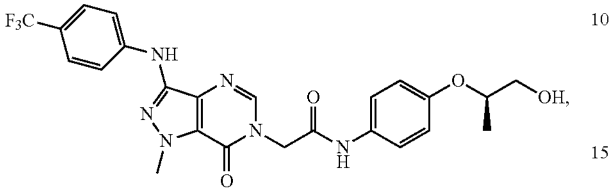
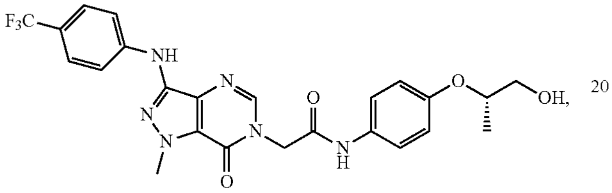
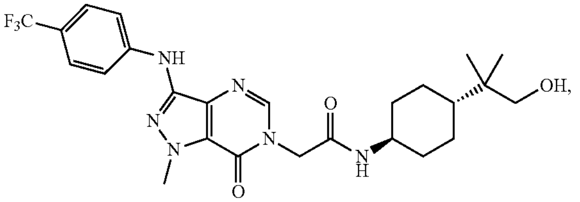
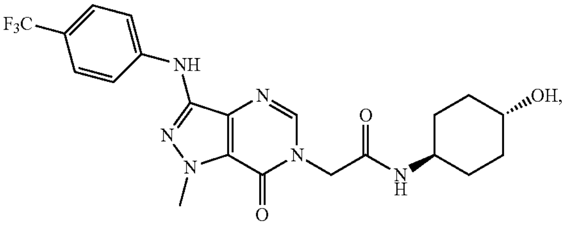
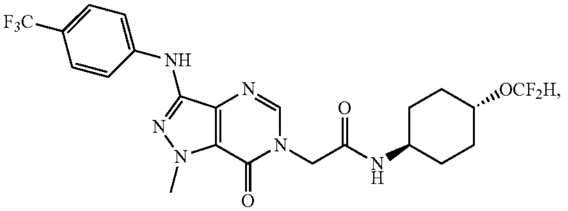
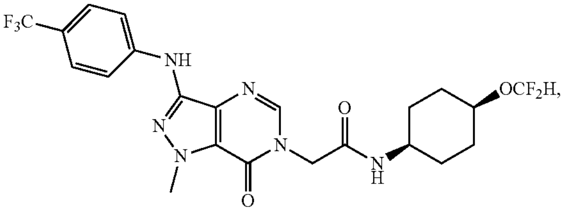
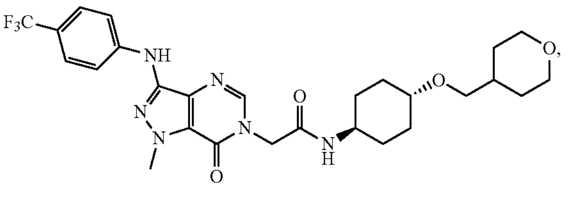
-continued
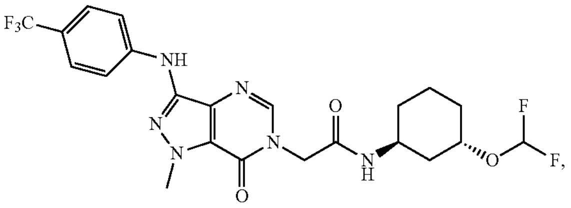
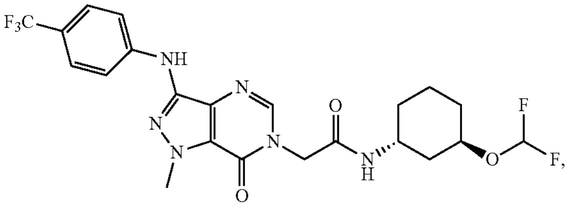
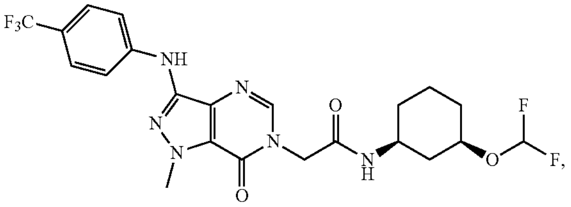
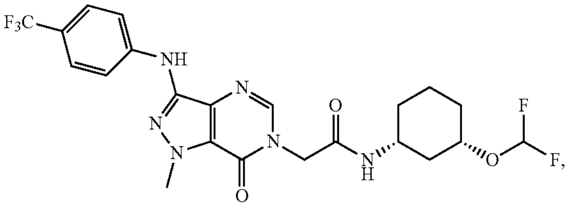
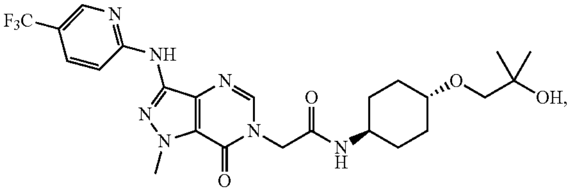
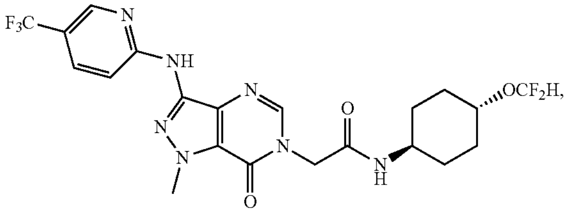
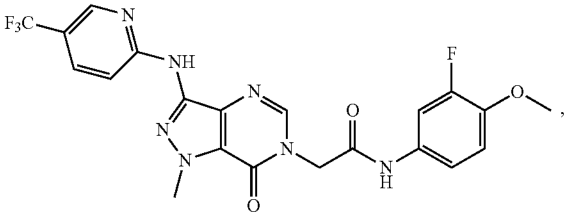
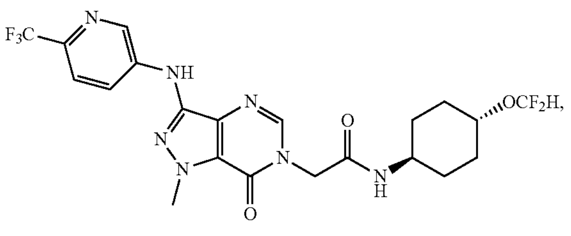

-continued

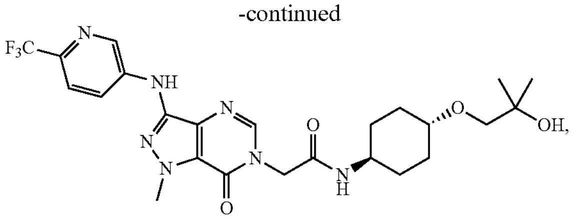

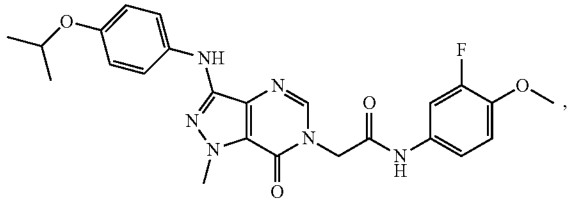

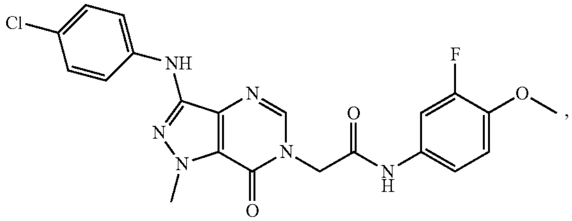

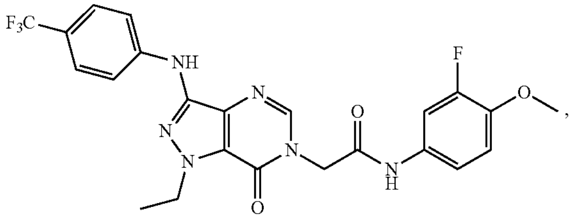

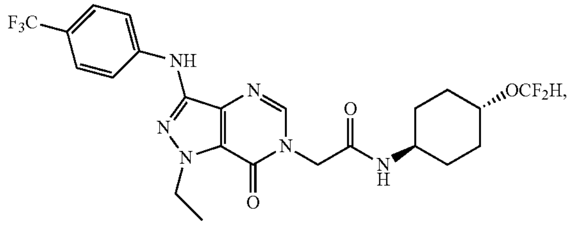

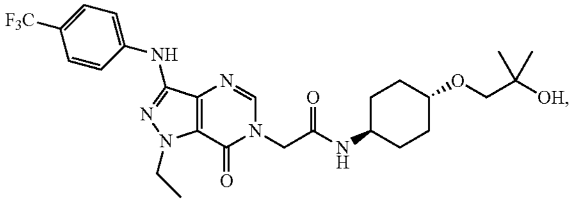

-continued

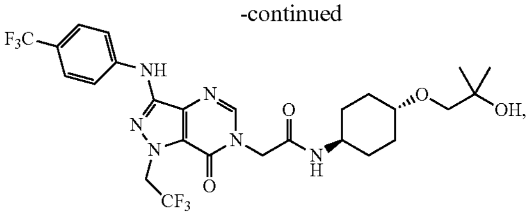

and

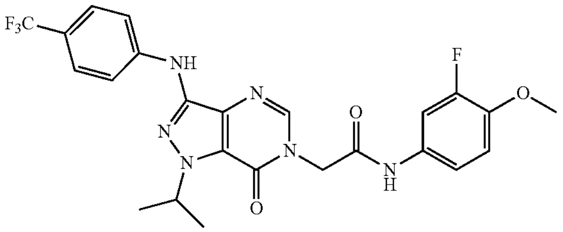

or a pharmaceutically acceptable salt or solvate thereof.

17. A pharmaceutical composition comprising a pharmaceutically acceptable diluent, excipient or binder, and a compound of claim 1; or a pharmaceutically acceptable salt or solvate thereof.

18. A method of treating cancer in a mammal, comprising administering to the mammal a compound of claim 1; or a pharmaceutically acceptable salt or solvate thereof, wherein the cancer is selected from adrenocortical carcinoma, ovarian cancer , head and neck cancer, edometrial cancer, hormone-dependent prostate cancer, non-small cell lung carcinoma (NSCLC), melanoma, pituitary gonadotroph adenomas, and sex cord stromal tumors.

19. The method of claim 18, wherein the cancer is adrenocortical carcinoma.

20. A method of treating an endocrine disease in a mammal, comprising administering to the mammal a compound of claim 1; or a pharmaceutically acceptable salt or solvate thereof, wherein the endocrine disease is selected from endogenous Cushing's syndrome,congenital adrenal hyperplasia, and polycystic ovary syndrome.

* * * * *